United States Patent
Re et al.

(10) Patent No.: US 8,470,037 B2
(45) Date of Patent: Jun. 25, 2013

(54) METHOD AND APPARATUS FOR RECONSTRUCTING A LIGAMENT

(75) Inventors: Paul Re, Boston, MA (US); Peter F. Marshall, Bolton, MA (US); Jesse Scott Drake, Clinton, MA (US)

(73) Assignee: Covidien LP, Mansfield, MA (US)

( * ) Notice: Subject to any disclaimer, the term of this patent is extended or adjusted under 35 U.S.C. 154(b) by 1652 days.

(21) Appl. No.: 11/206,892

(22) Filed: Aug. 18, 2005

(65) Prior Publication Data

US 2006/0052787 A1 Mar. 9, 2006

Related U.S. Application Data

(60) Provisional application No. 60/602,589, filed on Aug. 18, 2004, provisional application No. 60/688,588, filed on Jun. 8, 2005.

(51) Int. Cl.
*A61F 2/08* (2006.01)
*A61B 17/04* (2006.01)
*A61B 17/84* (2006.01)

(52) U.S. Cl.
USPC .................. 623/13.14; 606/323; 606/232

(58) Field of Classification Search
USPC ............... 623/13.11–13.14; 606/323, 232
See application file for complete search history.

(56) References Cited

U.S. PATENT DOCUMENTS

| | | |
|---|---|---|
| 3,579,831 A | 5/1971 | Stevens et al. |
| 4,669,473 A | 6/1987 | Richards et al. |
| 4,744,793 A | 5/1988 | Parr et al. |
| 5,026,373 A * | 6/1991 | Ray et al. ................. 606/86 A |
| 5,258,015 A | 11/1993 | Li et al. |
| 5,282,802 A | 2/1994 | Mahony, III |
| 5,507,812 A | 4/1996 | Moore |
| 5,632,748 A | 5/1997 | Beck, Jr. et al. |
| 5,702,397 A | 12/1997 | Goble et al. |
| 5,899,938 A | 5/1999 | Sklar et al. |
| 5,931,869 A | 8/1999 | Boucher et al. |
| 5,961,520 A | 10/1999 | Beck, Jr. et al. |
| 5,984,681 A * | 11/1999 | Huang ..................... 433/174 |
| 6,099,530 A | 8/2000 | Simonian et al. |
| 6,214,007 B1 | 4/2001 | Anderson |
| 6,355,066 B1 | 3/2002 | Kim |
| 6,379,361 B1 | 4/2002 | Beck, Jr. et al. |
| 6,387,129 B2 | 5/2002 | Rieser et al. |
| 6,464,706 B1 | 10/2002 | Winters |
| 6,533,816 B2 | 3/2003 | Sklar |
| 6,554,862 B2 * | 4/2003 | Hays et al. ................. 623/13.14 |
| 6,620,195 B2 | 9/2003 | Goble et al. |
| 6,632,245 B2 | 10/2003 | Kim |
| 6,824,384 B1 | 11/2004 | Bompard et al. |
| 7,083,647 B1 | 8/2006 | Sklar et al. |
| 7,144,413 B2 | 12/2006 | Wilford et al. |
| 2002/0042615 A1 | 4/2002 | Graf et al. |
| 2003/0171778 A1 | 9/2003 | Lizardi |
| 2003/0191530 A1 | 10/2003 | Sklar |
| 2004/0006349 A1 | 1/2004 | Goble et al. |
| 2004/0087953 A1 | 5/2004 | Singhatat et al. |
| 2006/0189991 A1* | 8/2006 | Bickley ..................... 606/72 |

* cited by examiner

*Primary Examiner* — Sameh Boles

(57) ABSTRACT

A system for reconstructing a ligament by fixing at least one graft ligament strand in a bone tunnel is provided. The system a retainer configured for disposition in the bone tunnel, the retainer including a crosshole for receiving a locking pin and a mounting shoulder formed about the crosshole, and a cap removably attached to the retainer for capturing the at least one graft ligament strand by compressing the at least one graft ligament strand between the cap and the retainer, wherein the cap includes at least one locking member configured to engage the mounting shoulder of the retainer to facilitate gripping of the at least one graft ligament strand between the cap and the retainer.

43 Claims, 95 Drawing Sheets

METHOD AND APPARATUS FOR RECONSTRUCTING A LIGAMENT

REFERENCE TO PENDING PRIOR PATENT APPLICATIONS

This patent application claims benefit of:

(1) pending prior U.S. Provisional Patent Application Ser. No. 60/602,589, filed Aug. 18, 2004 by Paul Re for METHOD AND APPARATUS FOR RECONSTRUCTING A LIGAMENT; and (2) pending prior U.S. Provisional Patent Application Ser. No. 60/688,588, filed Jun. 8, 2005 by Paul Re et al. for METHOD AND APPARATUS FOR RECONSTRUCTING A LIGAMENT.

The two above-identified patent applications are hereby incorporated herein by reference.

FIELD OF THE INVENTION

This invention relates to surgical methods and apparatus in general, and more particularly to methods and apparatus for reconstructing a ligament.

BACKGROUND OF THE INVENTION

A ligament is a piece of fibrous tissue which connects one bone to another.

Ligaments are frequently damaged (e.g., detached or torn or ruptured, etc.) as the result of injury and/or accident. A damaged ligament can impede proper motion of a joint and cause pain.

Various procedures have been developed to repair or replace a damaged ligament. The specific procedures used depend on the particular ligament which is to be restored and the nature and extent of the damage.

One ligament which is frequently damaged as the result of injury and/or accident is the anterior cruciate ligament (ACL) of the knee. Looking now at FIG. 1, an ACL 5 is shown extending across the interior of the knee joint, between the top of the tibia 10 and the bottom of the femur 15. A damaged ACL 5 can cause instability of the knee joint, further damage to other structures, and substantial pain and arthritis.

Numerous procedures have been developed to restore a badly damaged ACL through a graft ligament replacement. In general, these ACL replacement procedures involve drilling a bone tunnel 20 (FIG. 2) through tibia 10 and up into femur 15. Then a graft ligament 25, consisting of a harvested or artificial ligament or tendon, is passed through the tibial portion of bone tunnel 20 (i.e., the tibial tunnel 30), across the interior of the joint, and up into the femoral portion of bone tunnel 20 (i.e., the femoral tunnel 35). Then a distal portion of graft ligament 25 is secured in femoral tunnel 35 and a proximal portion of graft ligament 25 is secured in tibial tunnel 30.

There are currently a variety of ways to secure graft ligament 25 in a bone tunnel.

One way is to use an interference screw 40 (FIG. 3), such as the Arthrex interference screw (Arthrex, Inc. of Naples, Fla.), to "directly" wedge graft ligament 25 against the sidewall of the bone tunnel.

Another way is to use a bearing structure and expansion screw 45 (FIG. 4), such as the Mitek Intrafix system (Depuy Mitek Inc. of Norwood, Mass.), to "indirectly" wedge graft ligament 25 against the sidewall of the bone tunnel.

Still another way is to use a fastener device 50 (FIG. 5), such as the Innovasive/Mitek Lynx system (DePuy Mitek Inc. of Norwood, Mass.), to secure graft ligament 25 in the bone tunnel.

Yet another way is to use an anchor 55 (FIG. 6), such as the Mitek ligament anchor (DePuy Mitek Inc. of Norwood, Mass.), to suspend graft ligament 25 within the bone tunnel.

And another way is to use a suture suspension system 60 (FIG. 7), such as the Acufex/Smith & Nephew Endobutton system (Smith & Nephew, Inc. of Andover, Mass.), to suspend graft ligament 25 in a bone tunnel.

And still another way is to use a cross-pinning system 65 (FIG. 8), such as the Arthrex cross-pinning system (Arthrex, Inc. of Naples, Fla.), to suspend graft ligament 25 in the bone tunnel.

And yet another way is to pass graft ligament 25 completely through bone tunnel 20 and affix the graft ligament to the outside of the bone with a screw and washer arrangement 70 (FIGS. 3, 7 and 9) or a staple (not shown).

As noted above, the ACL reconstruction procedure generally involves securing a distal portion of graft ligament 25 in femoral tunnel 35, and securing a proximal portion of graft ligament 25 in tibial tunnel 30. Some of the aforementioned ligament reconstruction systems may be effectively and conveniently used in both femoral and tibial fixation, e.g., the Arthrex interference screw. Others of the aforementioned reconstruction systems are generally more appropriate for use in one or the other of the fixations, e.g., the Innovasive/Mitek Lynx system is generally more applicable for femoral fixation, and the screw and washer arrangement is generally more applicable for tibial fixation.

In addition to the foregoing, some of the aforementioned reconstruction systems utilize a graft ligament which is harvested so as to include a portion of bone block, e.g., a patellar tendon including a portion of the patella. Others of the aforementioned reconstruction systems utilize a graft ligament which is harvested so as to consist entirely of soft tissue, e.g., a harvested hamstring tendon.

In practice, it is generally preferable to harvest graft ligaments consisting entirely of soft tissue, e.g., a hamstring tendon, since this is less painful for the patient and involves less trauma to the donor site. However, graft ligaments consisting entirely of soft tissue are generally more difficult to secure to the host bone than those comprising a bone block, since the soft tissue is physically less rigid and more pliable (e.g., soft and relatively slippery) and the soft tissue tends to be biologically more fragile.

SUMMARY OF THE INVENTION

The present invention provides a new and improved method and apparatus for securing a graft ligament to a host bone. Significantly, the system may be used for both femoral and tibial fixation, and the system may be used where the graft ligament is formed entirely out of soft tissue (e.g., where the graft ligament comprises a harvested hamstring tendon).

More particularly, the present invention comprises the provision and use of a novel retainer which is slidably advanced to a desired fixation position within a bone tunnel, fixed in position within the bone tunnel (preferably by wedging and/or pinning) while applying a lateral force against the graft ligament so as to compressively hold the graft ligament against the sidewall of the bone tunnel, and which then, optionally, has the graft ligament secured thereto with a cap, whereby to secure the graft ligament to the retainer and hence additionally to the host bone.

The present invention also comprises the provision and use of a novel retainer which is slidably advanced to a desired fixation position within a bone tunnel so as to apply a lateral force against the graft ligament so as to compressively hold the graft ligament against the sidewall of the bone tunnel, and which is then locked to the host bone as the graft ligament is simultaneously secured to the retainer, whereby to secure the graft ligament to the retainer and hence additionally to the host bone.

In one preferred form of the invention, there is provided a system for reconstructing a ligament by fixing at least one graft ligament strand in a bone tunnel, comprising:

a retainer for disposition in the bone tunnel, wherein the retainer comprises at least one longitudinally-extending groove formed in the outside surface of the retainer, wherein the groove is configured to seat a graft ligament strand therein, and further wherein the at least one longitudinally-extending groove has a floor which is ramped radially outwardly as the floor extends distally-to-proximally, such that non-rotational advancement of the retainer into the bone tunnel will apply a compressive force to hold the graft ligament strand against the sidewall of the bone tunnel, and wherein the retainer comprises a transverse bore extending therethrough; and a locking pin sized to pass through the transverse bore and into the sidewall of the bone tunnel so as to fix the retainer in place within the bone tunnel.

In another preferred form of the invention, there is provided a method for reconstructing a ligament by fixing at least one graft ligament strand in a bone tunnel, comprising:

positioning the at least one graft ligament strand in the bone tunnel;

providing a retainer in the bone tunnel, wherein the retainer comprises at least one longitudinally-extending groove formed in the outside surface of the retainer, wherein the groove is configured to seat a graft ligament strand therein, and further wherein the at least one longitudinally-extending groove has a floor which is ramped radially outwardly as the floor extends distally-to-proximally, such that non-rotational advancement of the retainer into the bone tunnel will apply a compressive force to hold the graft ligament strand against the sidewall of the bone tunnel, and wherein the retainer comprises a transverse bore extending therethrough;

positioning the retainer in the bone tunnel so that the at least one graft ligament strand resides in a longitudinally-extending groove so that the retainer is wedged into place; and passing a locking pin through the transverse bore and into the sidewall of the bone tunnel so as to pin the retainer to the host bone.

In another preferred form of the invention, there is provided a system for reconstructing a ligament by fixing at least one graft ligament strand in a bone tunnel, comprising:

a retainer for disposition in the bone tunnel; and a cap removably attached to the retainer for capturing the at least one graft ligament strand to the retainer by compressing the at least one graft ligament strand between the cap and the retainer.

In another preferred form of the invention, there is provided an inserter for inserting a retainer into a bone tunnel, the inserter comprising:

a shaft;

an element on the distal end of the shaft for engaging a counterpart element on the retainer, whereby to releasably hold the retainer to the shaft; and an opening formed in the shaft, wherein the opening extends transverse to the longitudinal axis of the shaft, with the opening being aligned with a transverse opening formed in the retainer when the retainer is releasably held to the shaft.

In another preferred form of the invention, there is provided a dilator for simultaneously (i) dilating a graft ligament strand extending through a bone tunnel and (ii) dilating the sidewall of the bone tunnel, the dilator comprising:

a shaft sized to dilate the sidewall of the bone tunnel when the dilator is inserted into the bone tunnel; and at least one longitudinally-extending groove formed in the side wall of the dilator, wherein the at least one longitudinally-extending groove is configured to seat a graft ligament strand therein, and further wherein the at least one longitudinally-extending groove is sized to dilate the graft ligament strand when the graft ligament strand is seated in the at least one longitudinally-extending groove and the dilator is inserted into the bone tunnel.

In another preferred form of the invention, there is provided a method for reconstructing a ligament by fixing at least one graft ligament strand in a bone tunnel, comprising:

positioning a retainer in the bone tunnel; and attaching a cap to the retainer so as to capture the at least one graft ligament strand to the retainer by compressing the at least one graft ligament strand between the cap and the retainer.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
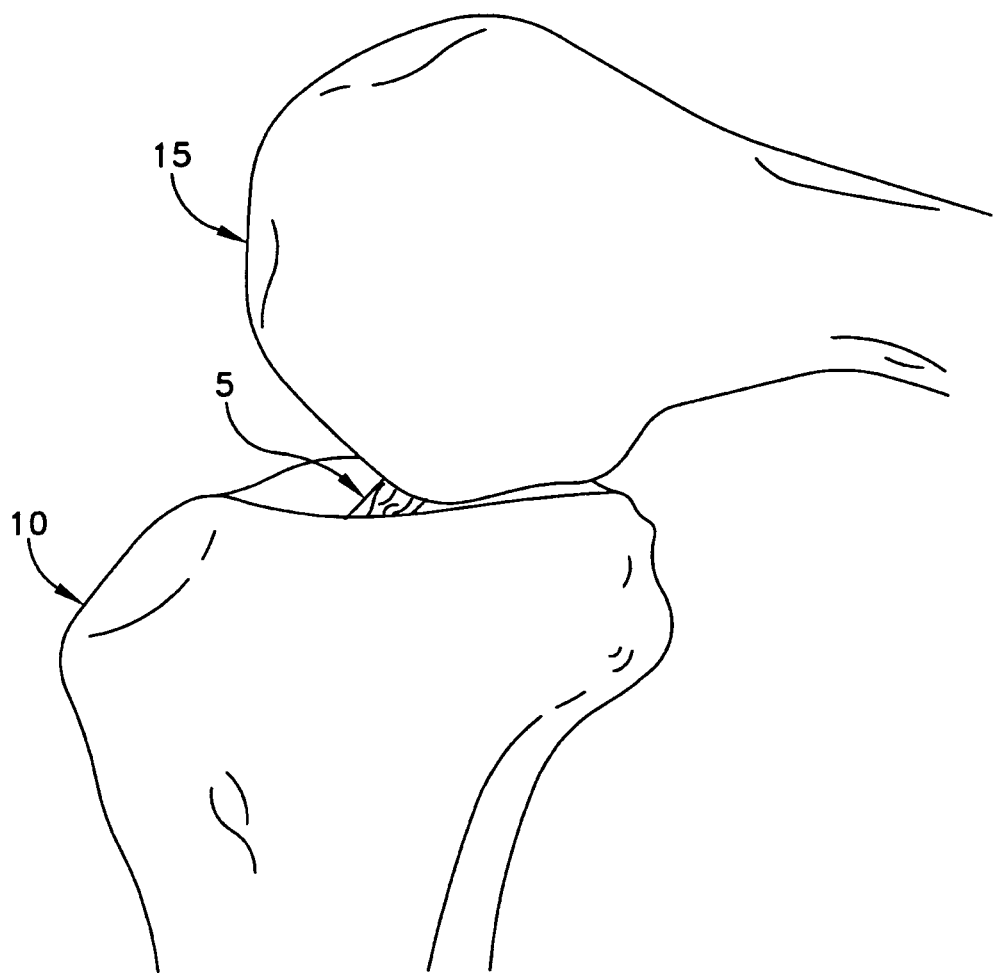
FIG. 1 is a schematic side elevational view of a knee joint showing an ACL extending between the tibia and the femur.
Figure 2:
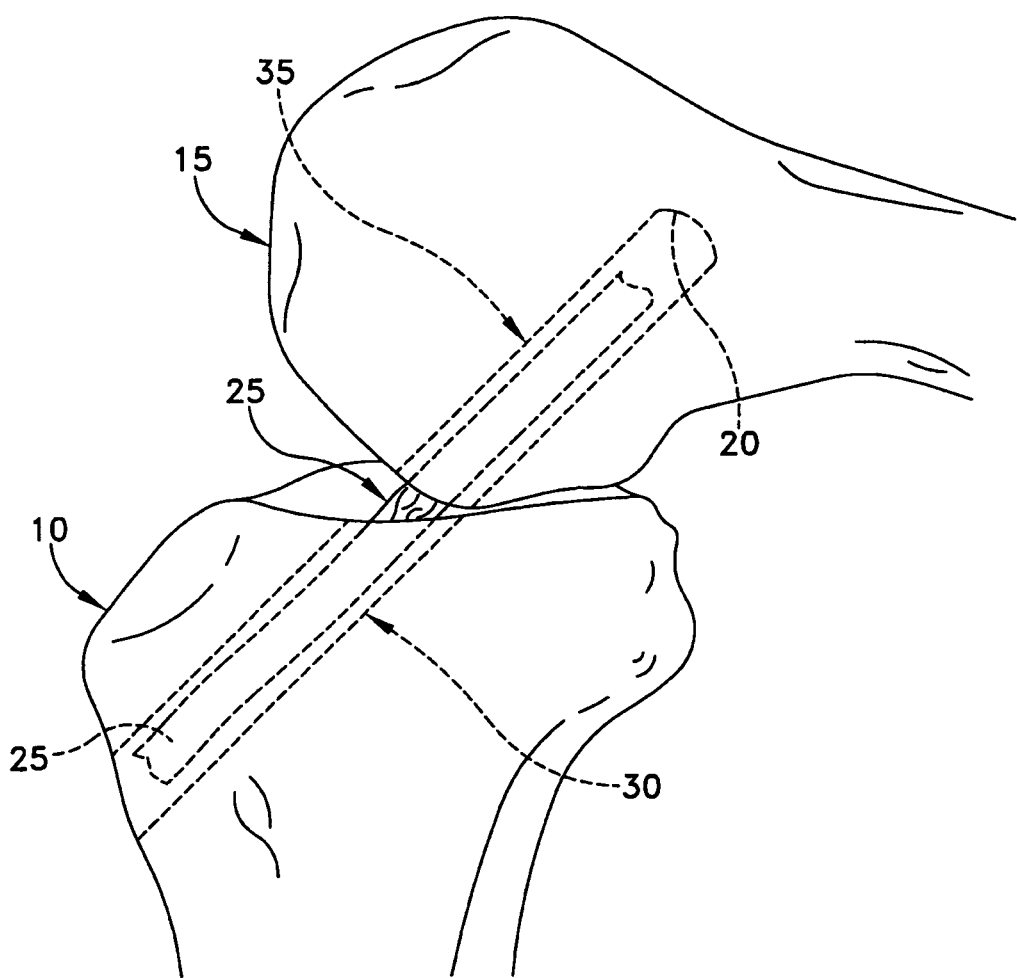
FIG. 2 is a schematic side elevational view of a knee joint showing a graft ligament extending between the tibia and the femur.
Figure 3:
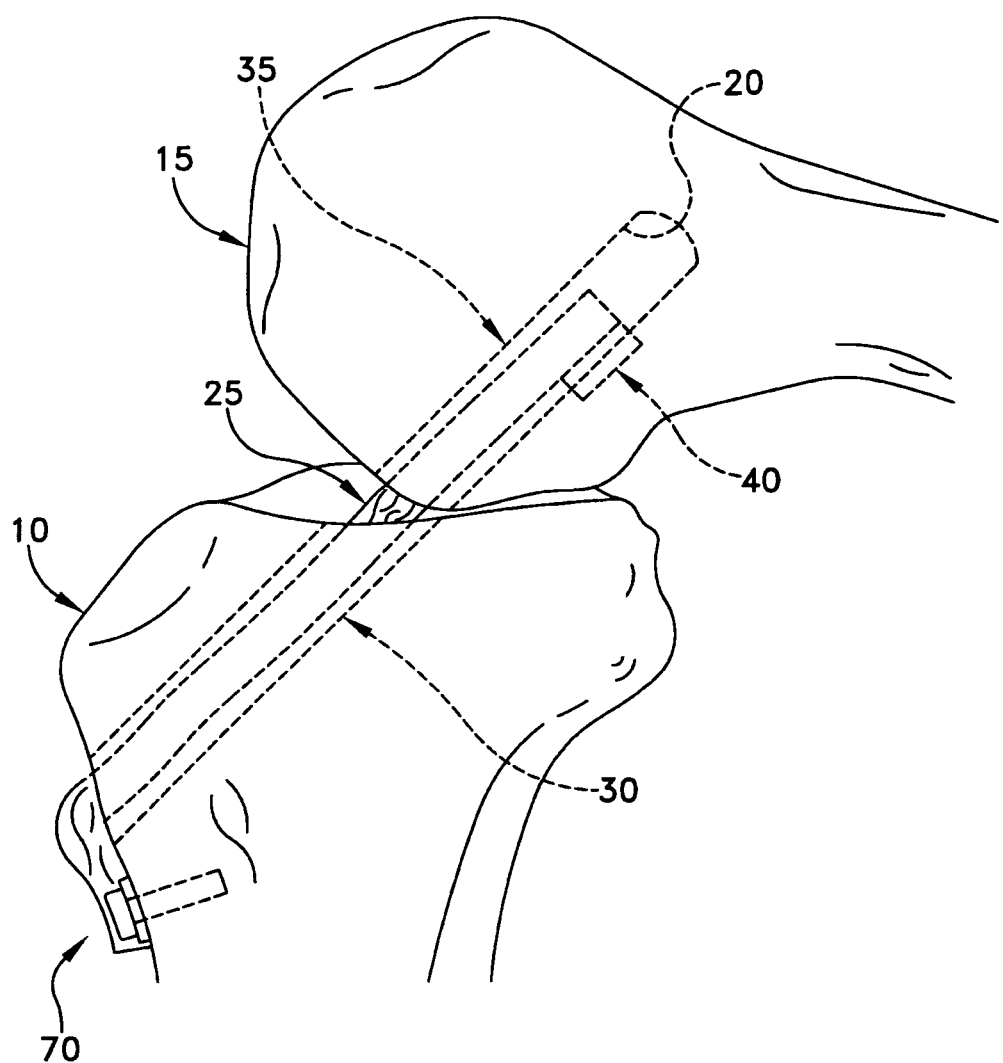
FIG. 3 is a schematic side elevational view showing a graft ligament secured in a bone tunnel by an interference screw.
Figure 4:
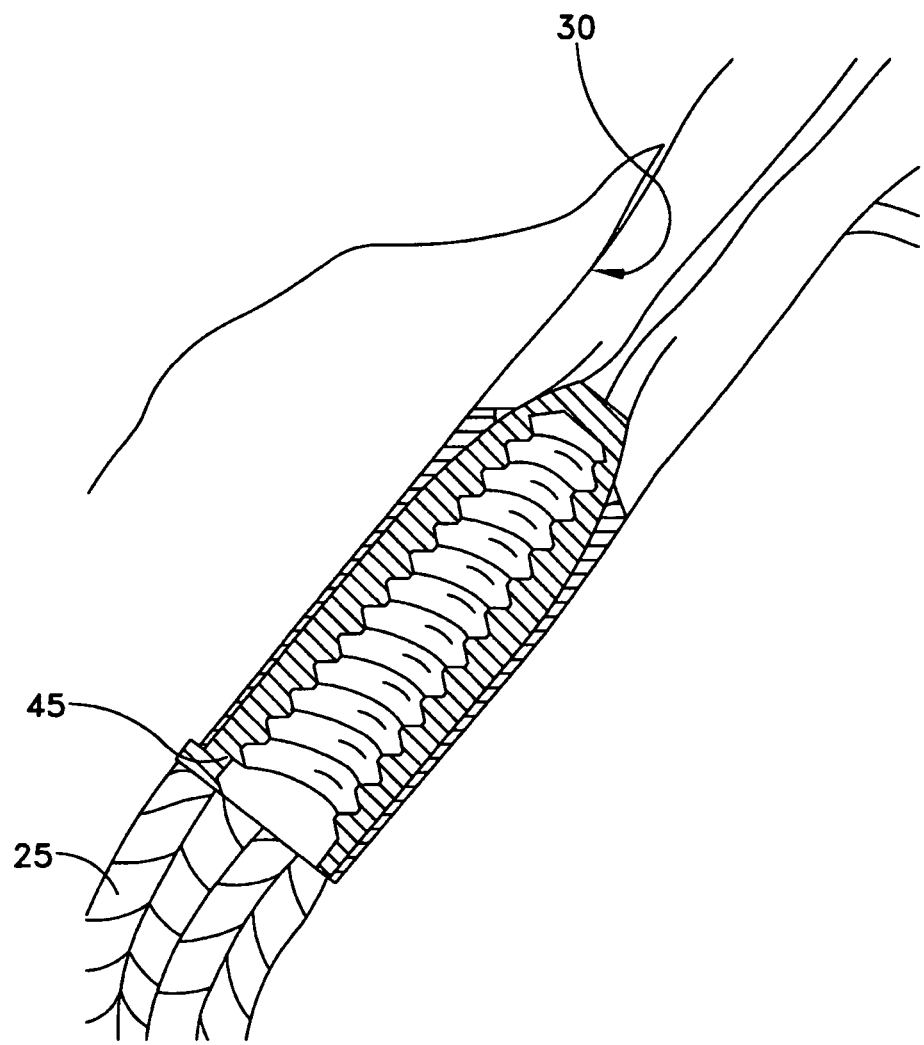
FIG. 4 is a schematic side elevational view showing a graft ligament secured in a bone tunnel by a bearing structure and expansion screw.
Figure 5:
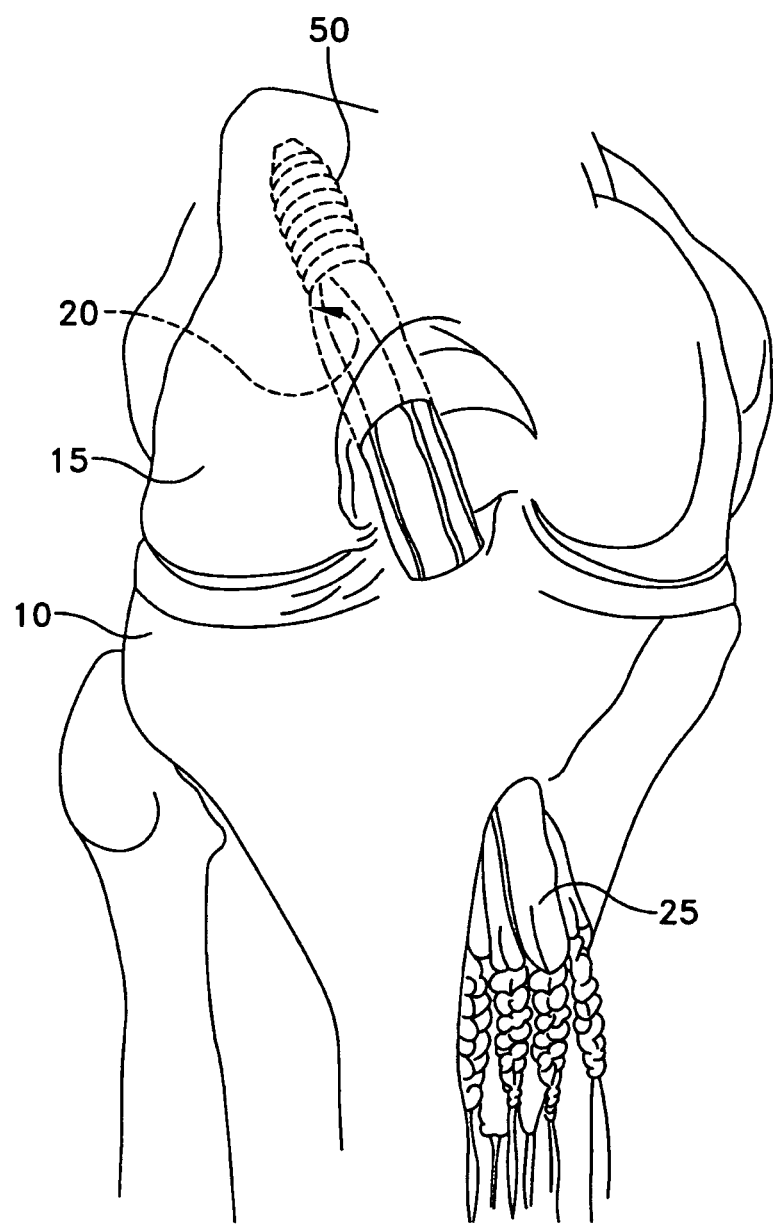
FIG. 5 is a schematic side elevational view showing a graft ligament secured in a bone tunnel by a fastener device.
Figure 6:
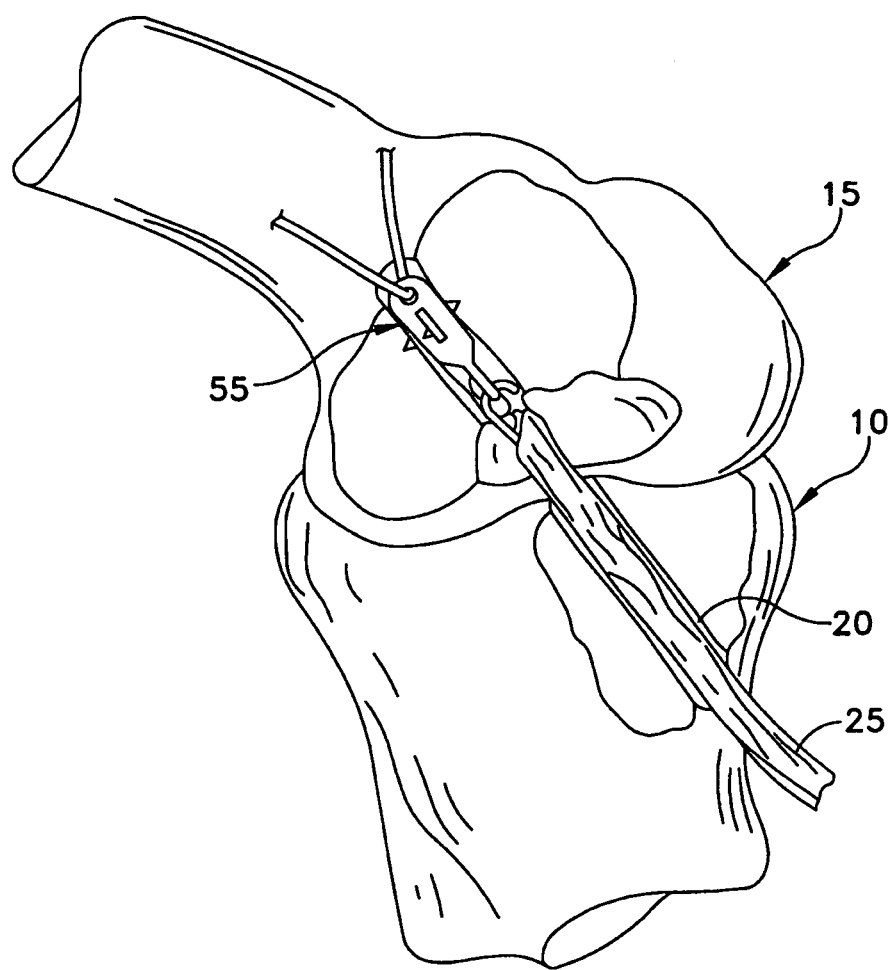
FIG. 6 is a schematic side elevational view showing a graft ligament secured in a bone tunnel by an anchor.
Figure 7:
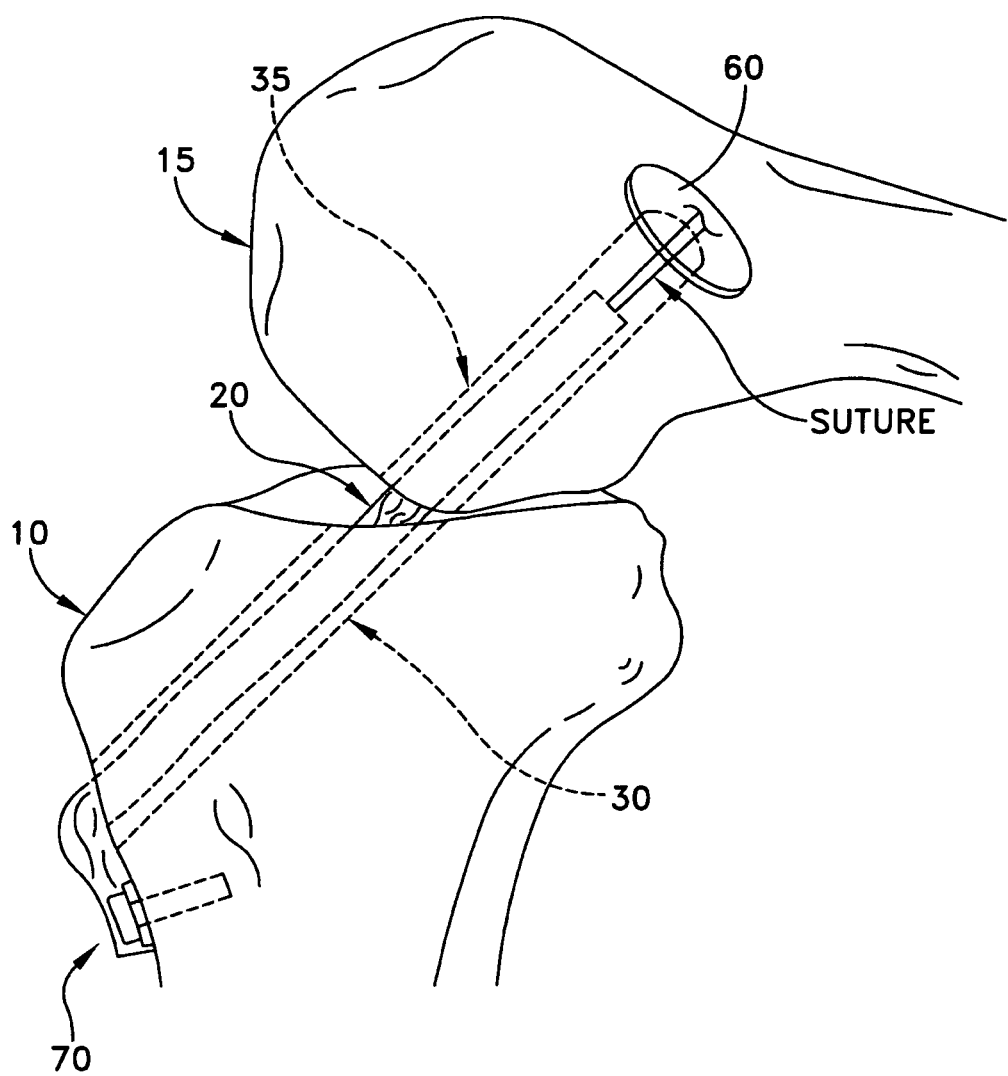
FIG. 7 is a schematic side elevational view showing a graft ligament secured in a bone tunnel by a suture suspension system.
Figure 8:
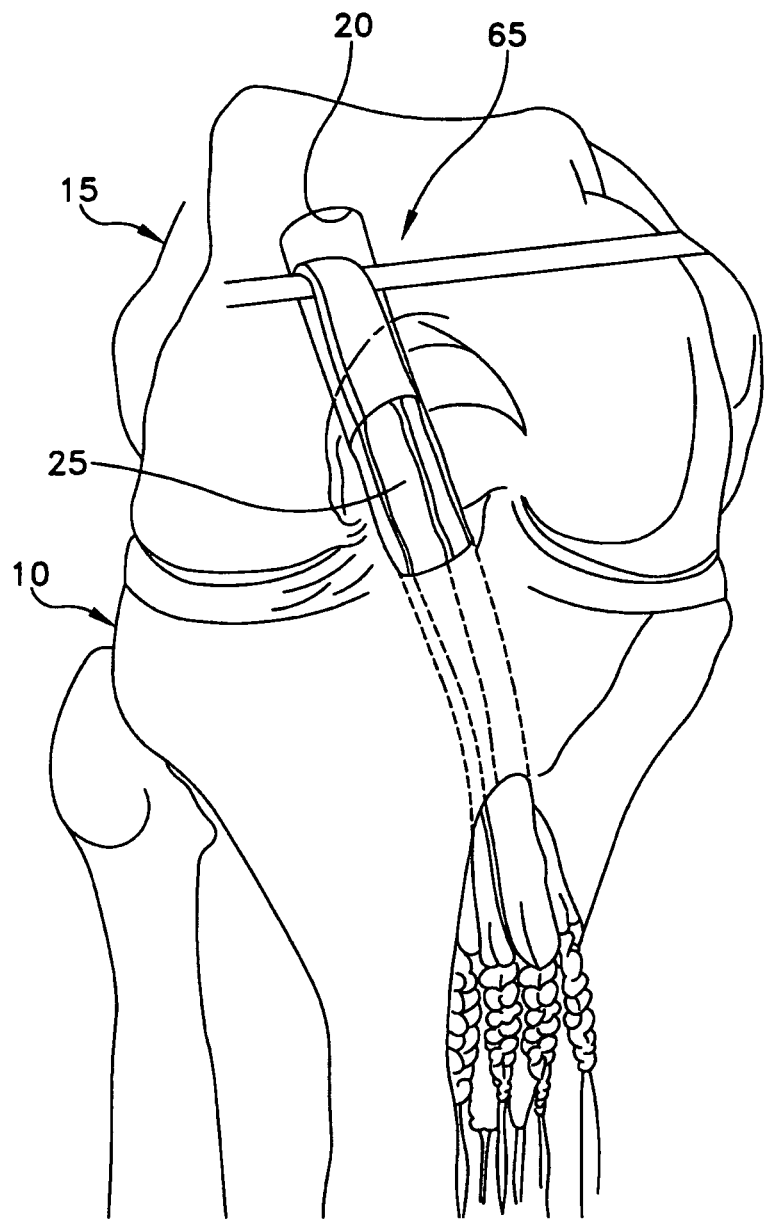
FIG. 8 is schematic side elevational view showing a graft ligament secured in a bone tunnel by a cross-pinning system.
Figure 9:
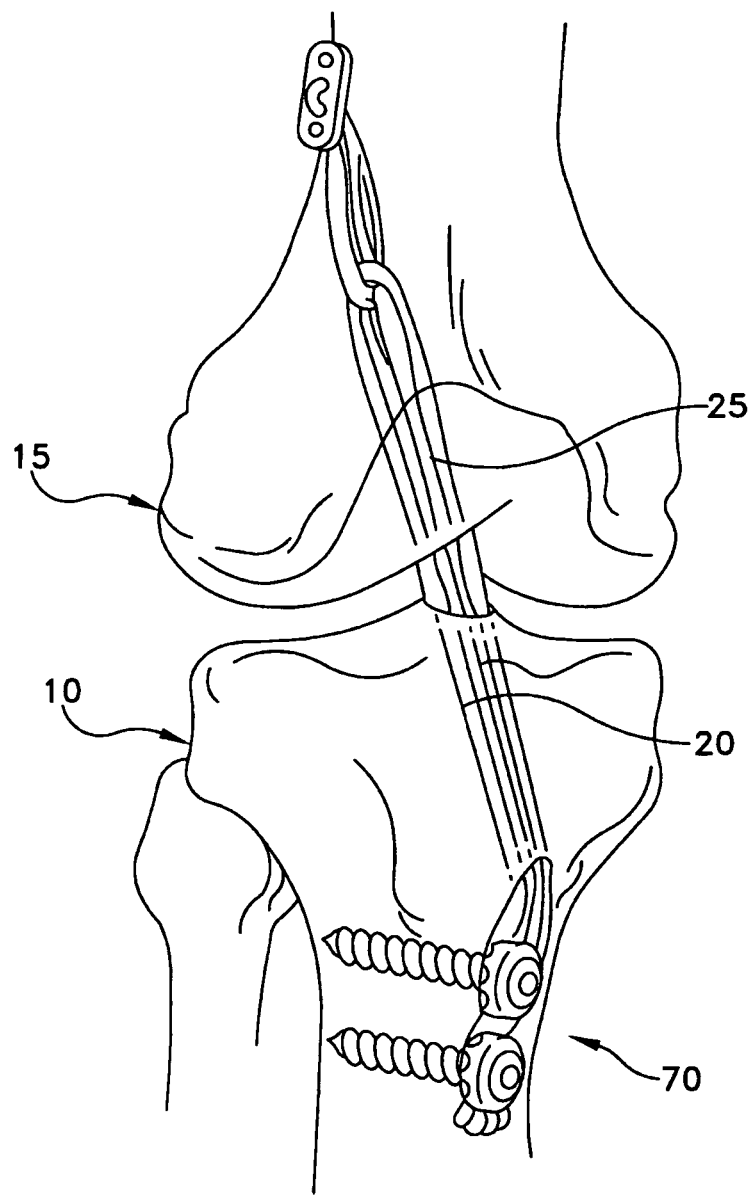
FIG. 9 is a schematic side elevational view showing a graft ligament secured in a bone tunnel by a screw and washer arrangement.
Figure 10:
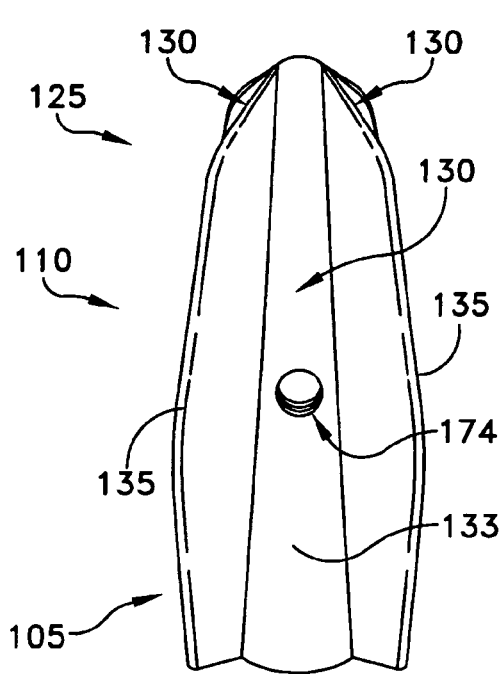
FIGS. 10 and 11 are schematic views showing a novel retainer for use in securing a graft ligament in a bone tunnel.
Figure 11:
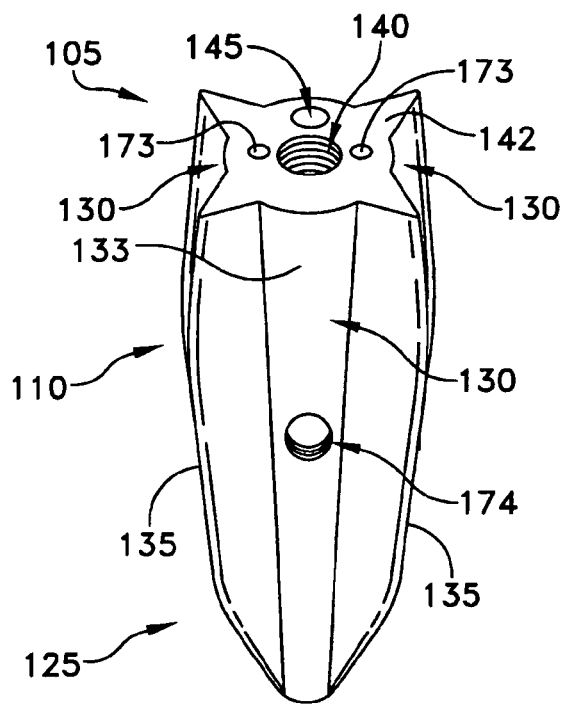
Figure 12:
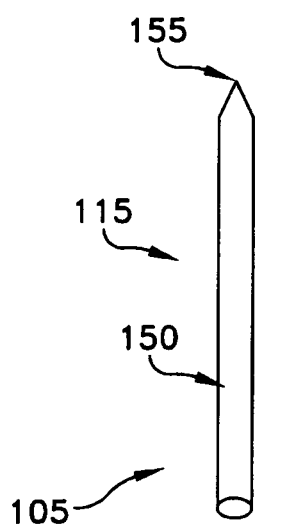
FIGS. 12 and 13 are schematic views showing locking pins for securing the retainer of FIGS. 10 and 11 in a bone tunnel.
Figure 13:
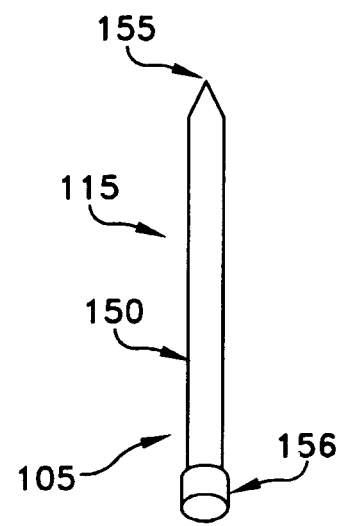

The present invention provides a new method and apparatus for graft ligament reconstruction. For convenience, the present invention will hereinafter be discussed in the context of its use for ACL tibial fixation; however, it should also be appreciated that the present invention may also be used for femoral fixation, or for fixation of other graft ligaments to other bones.

First Ligament Fixation System

Looking now at FIGS. 10-15, there is shown a ligament fixation system 105. Ligament fixation system 105 generally comprises a retainer 110, a locking pin 115 and, optionally, a locking cap 120.

In this form of the invention, as will hereinafter be discussed in further detail, retainer 110 is disposed in tibial tunnel 30, with graft ligament strands 25 running alongside retainer 110, whereby the graft ligament strands are compressively secured to the sidewall of tibial tunnel 30. The locking pin 115 may then be used to pin retainer 110 to the host bone. The locking cap 120 may be secured to retainer 110, in the process capturing graft ligament strands 25 to retainer 110, and hence additionally to the host bone.

Retainer 110, locking pin 115 and locking cap 120 are all formed out of one or more biocompatible materials. These biocompatible materials may be non-absorbable (e.g., stainless steel or plastic) or absorbable, or osteoconductive or inductive such as ceramic, allograft or coral. It should be appreciated that it is not necessary for all of the components to be formed out of the same material. In fact, each component is preferably formed out of the material or materials most advantageous for that particular component. Thus, different components may be formed out of different materials, different portions of a single component may be formed out of different materials, etc.

Retainer 110 is preferably rigid, or substantially rigid, although it may be to some extent compressive or collapsible so long as it is capable of ultimately maintaining a shape which is consistent with its intended function in the present invention. Thus, while retainer 110 is preferably rigid, or substantially rigid, retainer 110 can have any degree of rigidity which is consistent with the present invention.

In one preferred form of the invention, retainer 110 is preferably formed out of an acetyl polymer (e.g., Delrin) or PLA (polylactic acid).

In one preferred construction, retainer 110 (FIGS. 10, 11, 14 and 15) has a generally elongated configuration preferably characterized by a narrowing front end 125, which gives the retainer 110 a generally wedge-shaped configuration. This preferred wedge-shaped configuration assists in introducing retainer 110 into a bone tunnel and advancing it therein and, in one preferred form of the invention, the wedge-shaped configuration assists in locking retainer 110 within the bone tunnel by wedging it in place, as will hereinafter be discussed in further detail.

In addition to the wedge-shaped configuration, retainer 110 also has a plurality of longitudinally extending grooves 130 that extend along retainer 110. The floors 133 of grooves 130 preferably generally follow the taper of retainer 110, i.e., the floors 133 of the grooves ramp outward as they extend distal to proximal, so that the groove floors are further from the center axis of the retainer at the proximal ends of the grooves than they are at the distal ends of the grooves. Grooves 130 are sized and shaped to receive strands of graft ligament 25 therein, as will hereinafter be discussed. Preferably four grooves 130 are provided, to accommodate four ligament strands, one in each groove. Grooves 130 are preferably separated from one another by flared fins (or ribs or thickened walls) 135.

In one preferred construction, flared fins 135 define the outer perimeter of retainer 110 along substantially its entire length; in this construction, the outer edges of flared fins 135 define the tapered configuration of retainer 110.

Ribs and/or other protrusions may be formed on the floors 133 of grooves 130, and/or on flared fins 135, so as to inhibit longitudinal movement of graft ligament strands 25 relative to retainer 110 when the graft ligament strands are disposed in the retainer's grooves.

Retainer 110 also preferably comprises a threaded recess 140 to facilitate use of the optional locking cap 120 with the retainer. Threaded recess 140 extends distally from the proximal end surface 142 of the retainer 110. Threaded recess 140 permits the optional locking cap 120 to be releasably secured to retainer 110, as will also hereinafter be discussed (see FIGS. 14, 15, 22 and 23). Alternatively, recess 140 can also be configured to accept a ribbed or barbed locking mechanism for securing the optional locking cap 120 to retainer 110.

Figure 18:
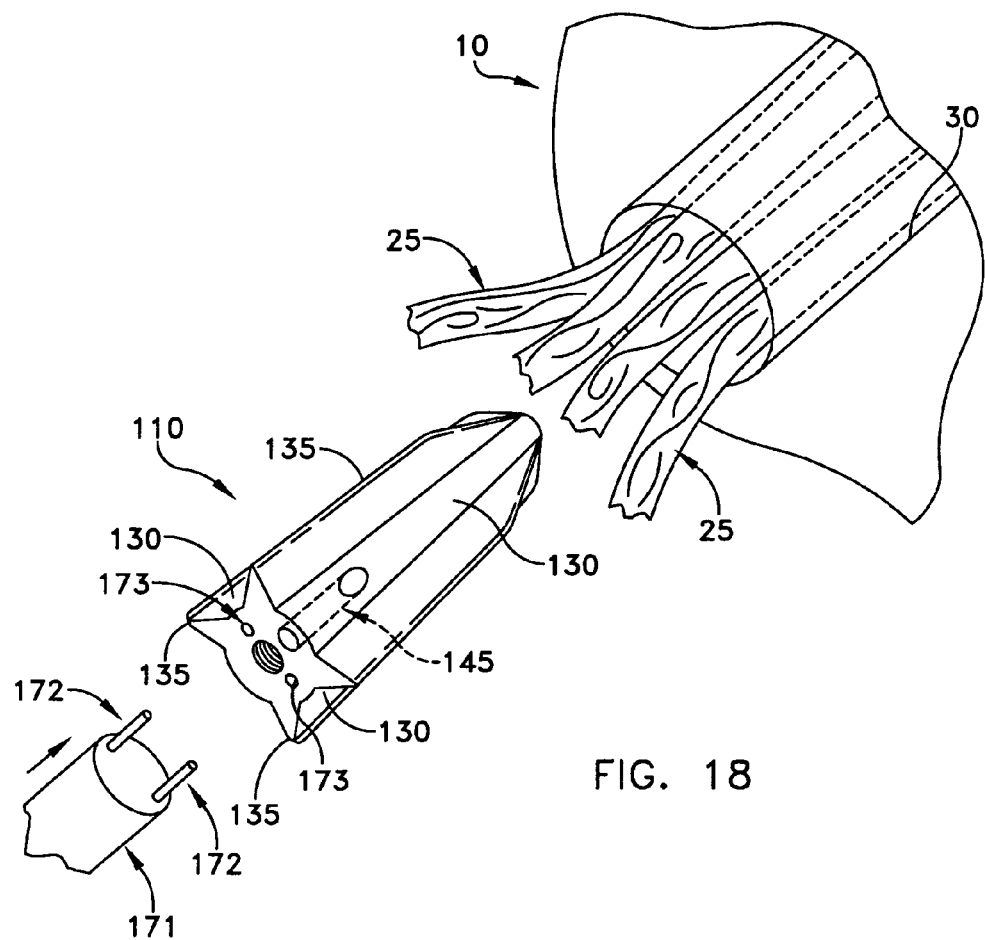

In one preferred construction, retainer 110 also comprises one or more transverse or oblique bores 145 (FIGS. 11, 14, 15 and 18) that extend through the proximal end of retainer 110, with one end of bores 145 opening on the proximal end surface 142 of retainer 110 and the other end of bores 145 opening on the floor 133 of a groove 130 (FIG. 18). In another preferred construction, one end of bores 145 open on the proximal end surface 142 of retainer 110 and the other end of bores 145 open on a flared fin 135. In still another preferred construction, one end of bores 145 open on the proximal end surface 142 of retainer 110 and the other end of bores 145 open on the floor 133 of a groove 130 and/or on a flared fin 135.

Locking pins 115 (FIGS. 12 and 13) of ligament fixation system 105 comprise a shaft 150 terminating in a pointed distal tip 155. If desired, an enlarged head 156 can be provided on the proximal end of shaft 150. Locking pins 115 are used to secure retainer 110 to the host bone, as will hereinafter be discussed. Furthermore, to the extent that locking pins 115 pass through the graft ligament 25, the locking pins 115 also serve to secure the graft ligament directly to the bone.

Figure 14:
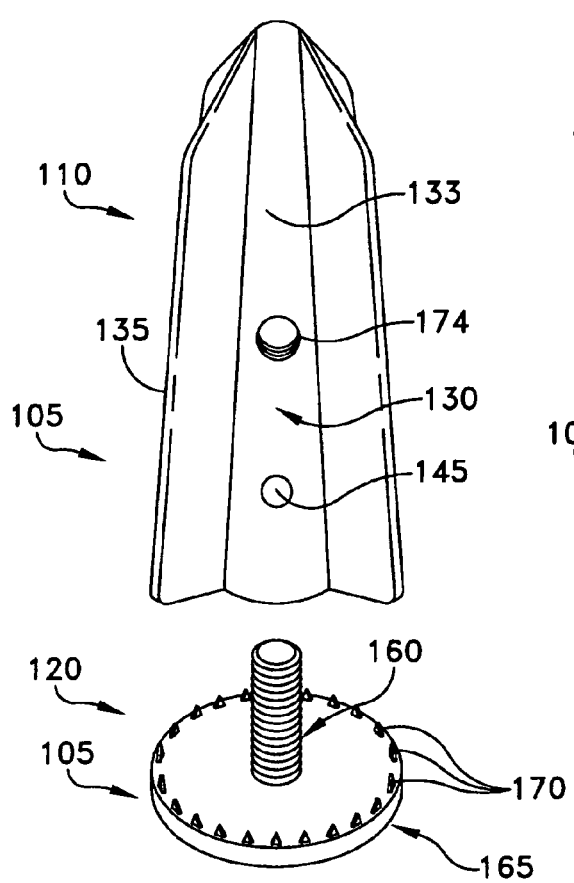
FIGS. 14 and 15 are schematic views showing the retainer of FIGS. 10 and 11 with optional locking caps for securing a graft ligament to the retainer of FIGS. 10 and 11.
Figure 15:
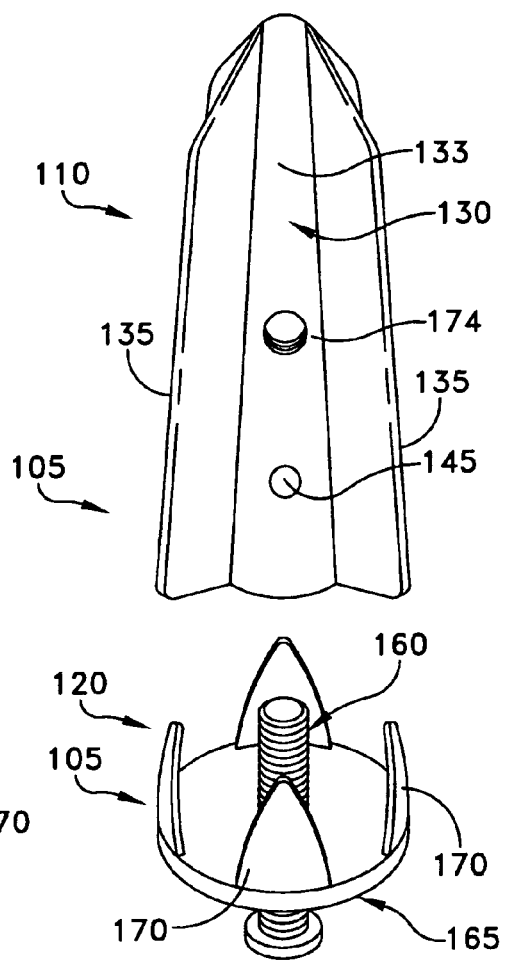

As noted above, ligament fixation system 105 may, optionally, also comprise locking cap 120. In one preferred form of the invention, locking cap 120 (FIGS. 14 and 15) comprises a threaded stem 160 (preferably in the form of a screw) and an enlarged cap 165. Threaded stem 160 is sized to be threadably received in threaded recess 140 of retainer 110, whereby to releasably secure the locking cap 120 to retainer 110. Alternatively, threaded stem 160 can also be ribbed or barbed to create an alternative locking mechanism, in which case the retainer's recess 140 is correspondingly configured. Enlarged cap 165 is preferably sized to have a diameter substantially the same as the proximal end surface 142 of retainer 110 and serves to secure the strands of graft ligament 25 to retainer 110, as will hereinafter be discussed. If desired, locking cap 165 can include a plurality of distally-projecting fingers 170. Fingers 170 can be distributed throughout the entire distal surface of enlarged cap 165 or about only the periphery of the distal surface (e.g., such as is shown in FIGS. 14 and 15). Fingers 170 may be of various sizes (see FIGS. 14 and 15) and, if desired, they may be aligned with grooves 130 in retainer 110 (FIG. 15), so as to form a complementary coupling.

Ligament fixation system 105 is preferably used as follows.

Figure 16:
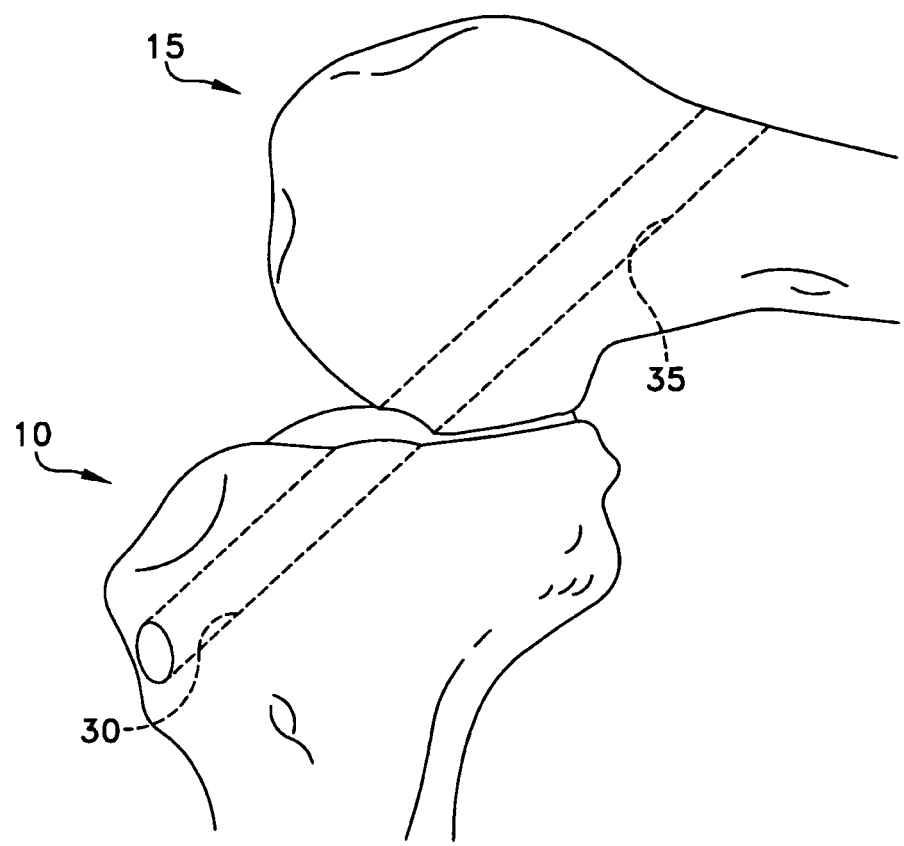
FIGS. 16-24 show a graft ligament being secured in a bone tunnel using the system of FIGS. 10-15.
Figure 16A:
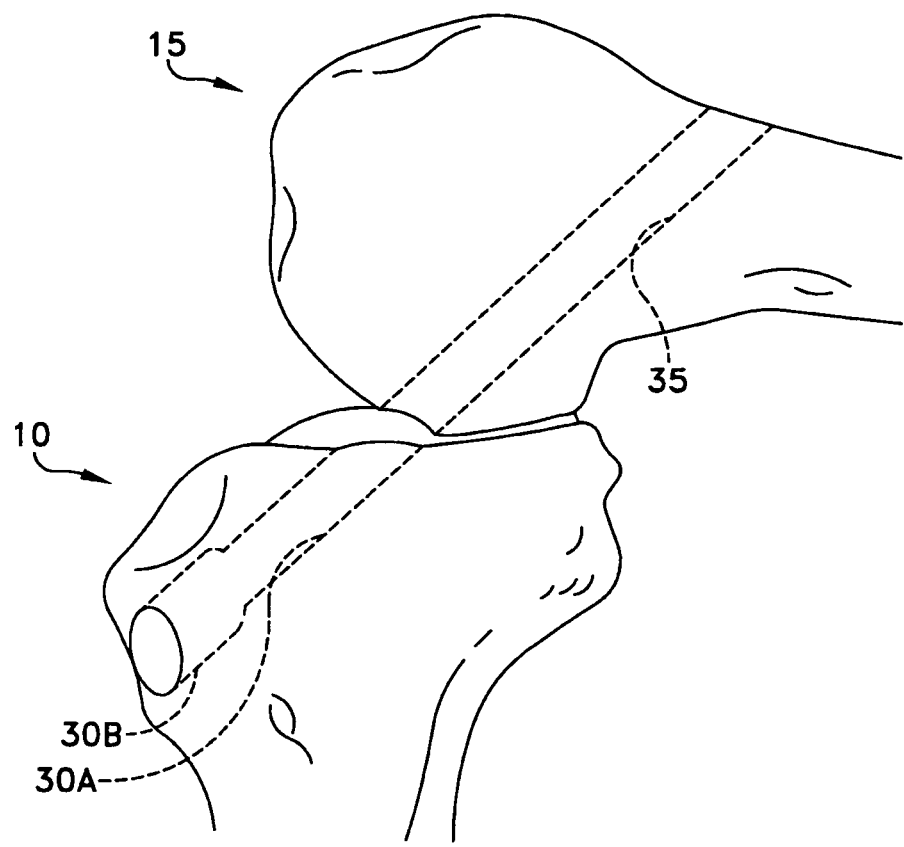
Figure 16B:
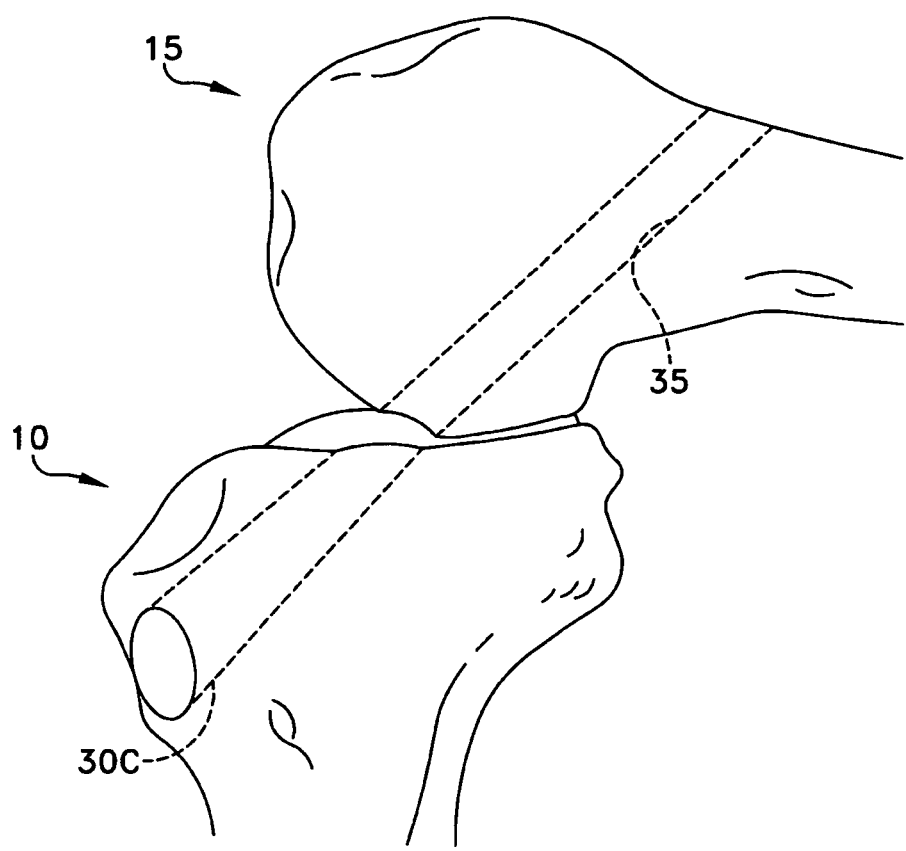

First, tibial bone tunnel 30 and femoral bone tunnel 35 are formed (FIG. 16). In one preferred form of the invention, tibial tunnel 30 is formed with a stepped construction (e.g., such as a bore 30A and a counterbore 30B, as shown in FIG. 16A), or tibial tunnel 30 is formed with a tapered construction (e.g., such as the bore 30C shown in FIG. 16B), so that the wedge-shaped retainer 110 will advance only a portion of the way down bone tunnel 30 before wedging itself into a locked position within the bone tunnel. The techniques and apparatus for forming such stepped or narrowed bone tunnels are well known in the art. By way of example but not limitation, a stepped bone tunnel may be formed by drilling a bore/counterbore configuration in the bone, and a narrowed bone tunnel may be formed by drilling a smaller tunnel in the bone and then selectively widening that tunnel with a tapered bone dilator instrument.

Figure 17:
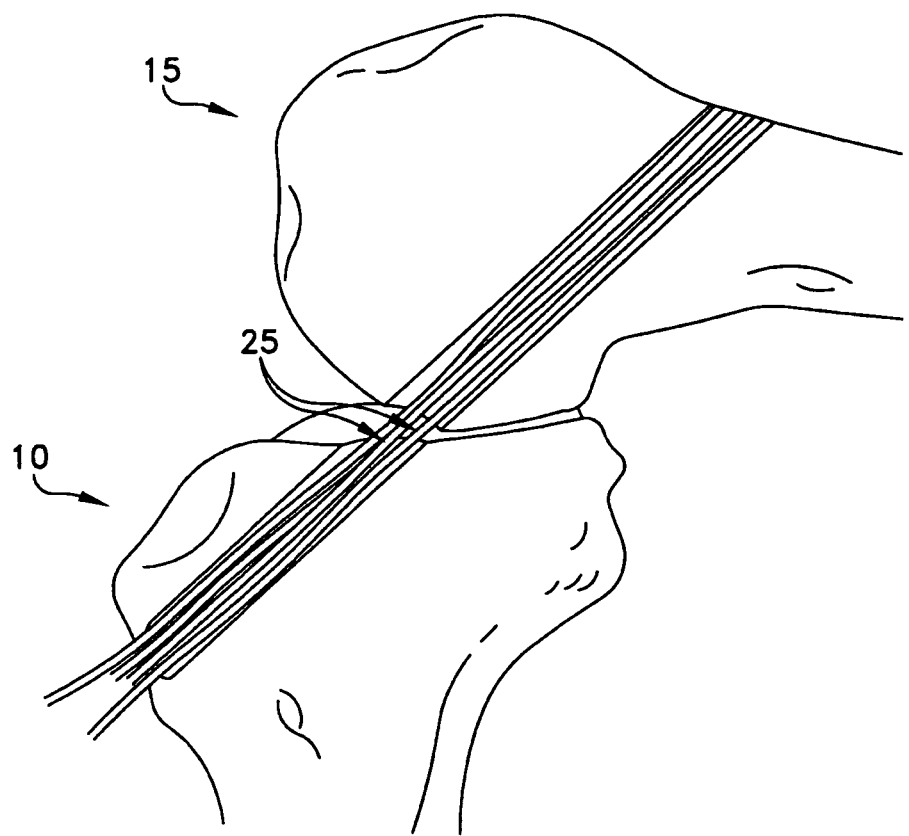

Next, graft ligament strands 25 are fixed to femur 15 in ways well known in the art, with the graft ligament strands 25 extending back through tibia 10 (FIG. 17).

Figure 19:
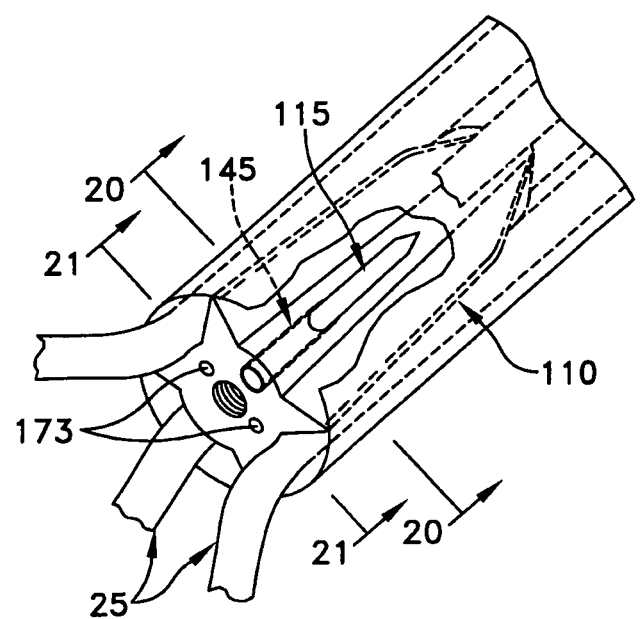
Figure 20:
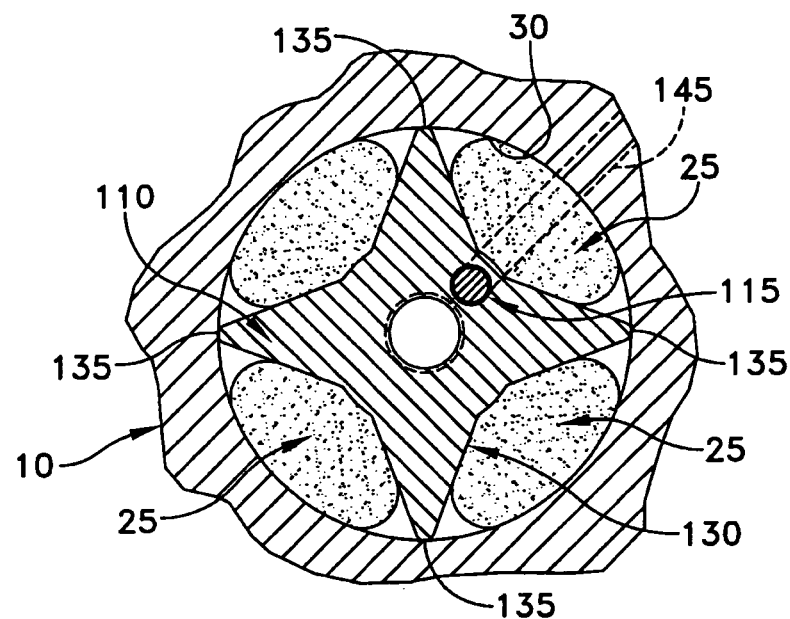
Figure 21:
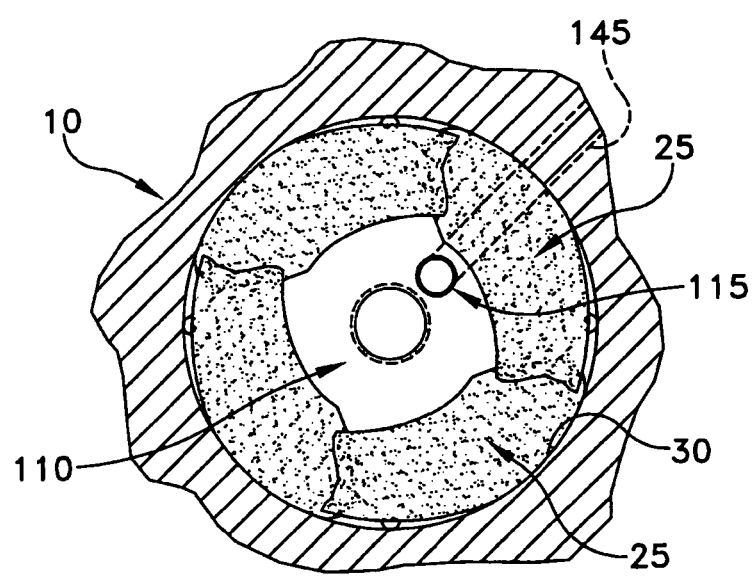

Then, with graft ligament strands 25 being tensioned by pulling on the free ends of the strands which extend out the proximal end of tibial tunnel 30, retainer 110 is advanced into tibial bone tunnel 30, with graft ligament strands 25 being received in the retainer's grooves 130 (FIGS. 18 and 19). Retainer 110 may be advanced into tibial tunnel 30 using a variety of techniques, e.g., pushing or pulling. By way of example but not limitation, retainer 110 may be pushed up tibial tunnel 30 using an inserter 171 (FIG. 18) having a pair of fingers 172 for engaging a corresponding pair of holes 173 formed in the proximal end of retainer 110. As retainer 110 is advanced into tibial tunnel 30, the ramped floors 133 of grooves 130 progressively force the ligament strands into firm yet atraumatic contact with the sidewall of the bone tunnel (see FIGS. 19-21).

As retainer 110 is advanced further and further into tibial tunnel 30, it will eventually become wedged into position by virtue of the retainer's geometry (i.e., the ramped floors of grooves 130 and the tapered shape of flared fins 135), the stepped or tapered geometry of the tibial tunnel 30, and the presence of graft ligament strands 25 between retainer 110 and the sidewall of the bone tunnel. In this respect it will also be appreciated that this progressive wedging action is also generally influenced by the typically resilient nature of graft ligament strands 25, and by the typically softer cancellous bone which forms the sidewall of the intermediate portions of tibial tunnel 30 (and which permits some compression as wedging occurs). This wedging action will effectively lock the graft ligament strands 25 to the sidewall of tibial tunnel 30, whereby to secure the graft ligament strands to the host bone.

When retainer 110 has been advanced a sufficient distance within tibial tunnel 30 (and is preferably wedged into place on account of its tapered shape, including but not limited to the engagement of the flared fins 135 with the sidewall of the stepped or tapered bone tunnel 30), a locking pin 115 can be inserted through the transverse or oblique bore 145 (FIGS. 19-21) and into the sidewall of the bone tunnel, whereby to lock retainer 110 to the host bone. By forming transverse bore 145 so that it opens on the proximal end surface 142 of retainer 110 and extends at an oblique angle relative to the longitudinal axis of retainer 110, locking pin 115 can be introduced to transverse bore 145 from the mouth of tibial tunnel 30 and essentially form a "toe-in" fastening of retainer 110 to the host bone. Furthermore, to the extent that locking pin 115 passes through the graft ligament 25, the locking pin also serves to secure the graft ligament directly to the bone.

Alternatively, and/or additionally, center hole 174 (FIGS. 10 and 11) may be used for a crosspin or cross-screw fixation of retainer 110 to tibia 10. However, such an arrangement is generally somewhat less convenient, since center hole 174 is concealed within the interior of tibia 10 and systems must be provided to ensure accurate "blind" crosspinning or cross-screwing through the concealed center hole 174.

Thus, in a preferred configuration of the present invention, retainer 110 is prevented from advancing beyond its deployment site by virtue of (1) its wedged engagement with the narrowing wall of tibial tunnel 30, and (2) locking pin 115. As noted above, the narrowing of bone tunnel 30 may be formed with a stepped configuration or a narrowing configuration. In some cases the stepped configuration may be preferred, since the stepped tunnel configuration forms a more tortuous path of graft travel, thereby increasing friction and locking of the graft/tunnel/device interface. In general, the stepped tunnel design has a smaller diameter as it approaches the interior of the joint, so as to limit advancement of retainer 110 toward the interior of the joint.

At this point the graft ligament fixation may be considered completed, since retainer 110 is compressively securing the graft ligament strands to the sidewall of tibial tunnel 30 and, hence, to the host bone. Furthermore, to the extent that the locking pin 115 passes through the graft ligament, the locking pin also serves to secure the graft ligament directly to the bone.

Optionally, and more preferably, however, the locking cap 120 may be used to secure graft ligament strands 25 to retainer 110.

Figure 22:
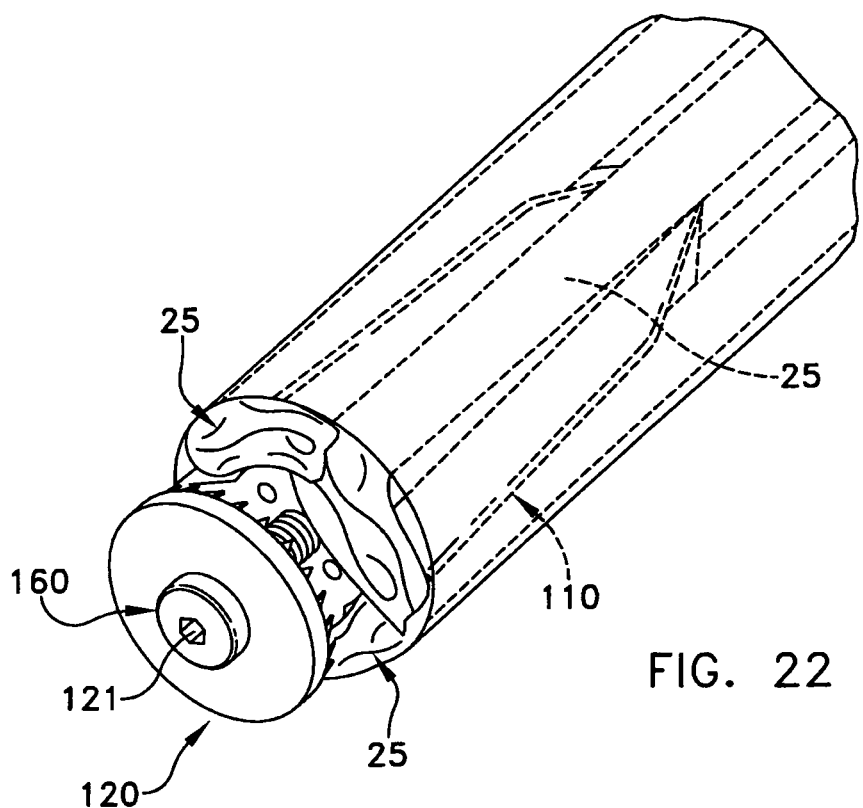
Figure 23:
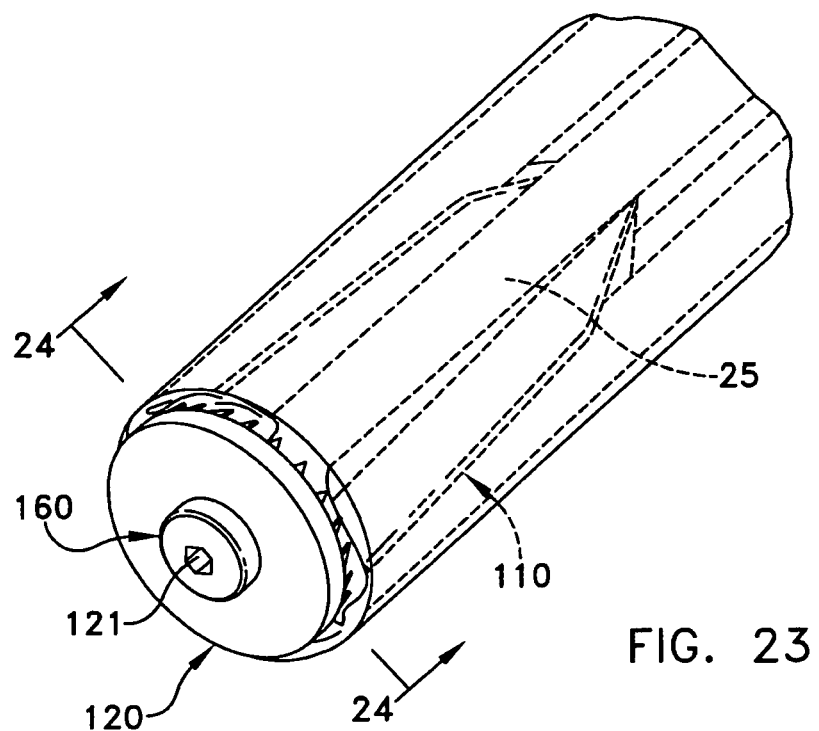
Figure 24:
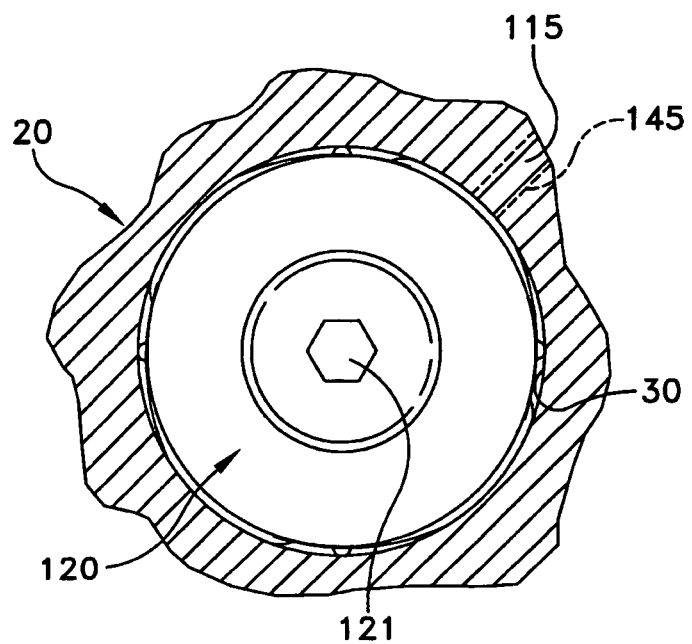

More particularly, after retainer 110 is positioned in tibial tunnel 30, graft ligament strands 25 are folded over the proximal end surface 142 of retainer 110 (FIGS. 22 and 23). Then locking cap 120 is secured to retainer 110 (FIGS. 22-24), e.g., with a hex driver (not shown) engaging a driver recess 121 (FIGS. 22-24), with the locking cap 120 securing graft ligament strands 25 to retainer 110, whereby to lock graft ligament strands 25 to retainer 110 and hence to the host bone.

Thus, with the use of optional locking cap 120, graft ligament strands 25 are captured to the host bone by (i) lateral compression created along the length of retainer 110, as the retainer forces the graft ligament strands outboard against the sidewall of the bone tunnel, and (ii) axial compression created between the underside of locking cap 120 and the proximal end surface 142 of retainer 110 (which is in turn wedged into position in tibial tunnel 30 and pinned into place with locking pin 115). Furthermore, to the extent that the locking pin 115 passes through the graft ligament 25, the locking pin also serves to secure the graft ligament directing to the bone.

It should also be appreciated that, inasmuch as graft ligament strands 25 tend to be slightly elastic, and inasmuch as graft ligament strands 25 are secured under tension, upon retainer deployment, graft ligament strands 25 will tend to urge retainer 110 further into the bone tunnel, thereby enhancing the wedging lock to the bone.

Thereafter, over time, graft ligament strands 25 and the host bone integrate so as to provide a biologic union.

Alternatively, the mouth of the tibial tunnel can be countersunk (at the tibial cortex) to a larger diameter for a short distance. With this arrangement, a larger diameter locking cap can be used to secure graft ligament 25 to the retainer as well as to the annular rim formed at the base of the countersunk hole. This further increases the tortuous path followed by the graft strands and increases the holding strength of the system.

Figure 25:
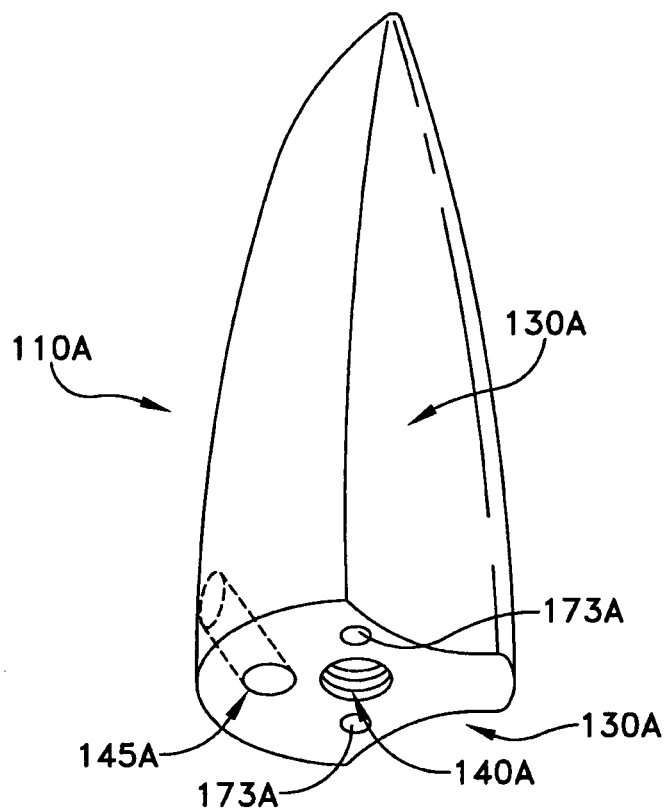
FIGS. 25 and 26 are schematic views showing a second novel retainer for use in securing a graft ligament in a bone tunnel.
Figure 26:
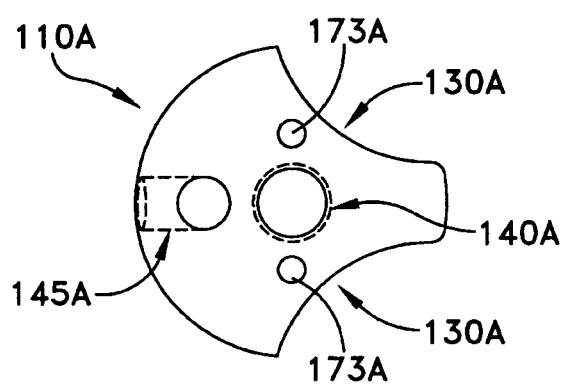
Figure 27:
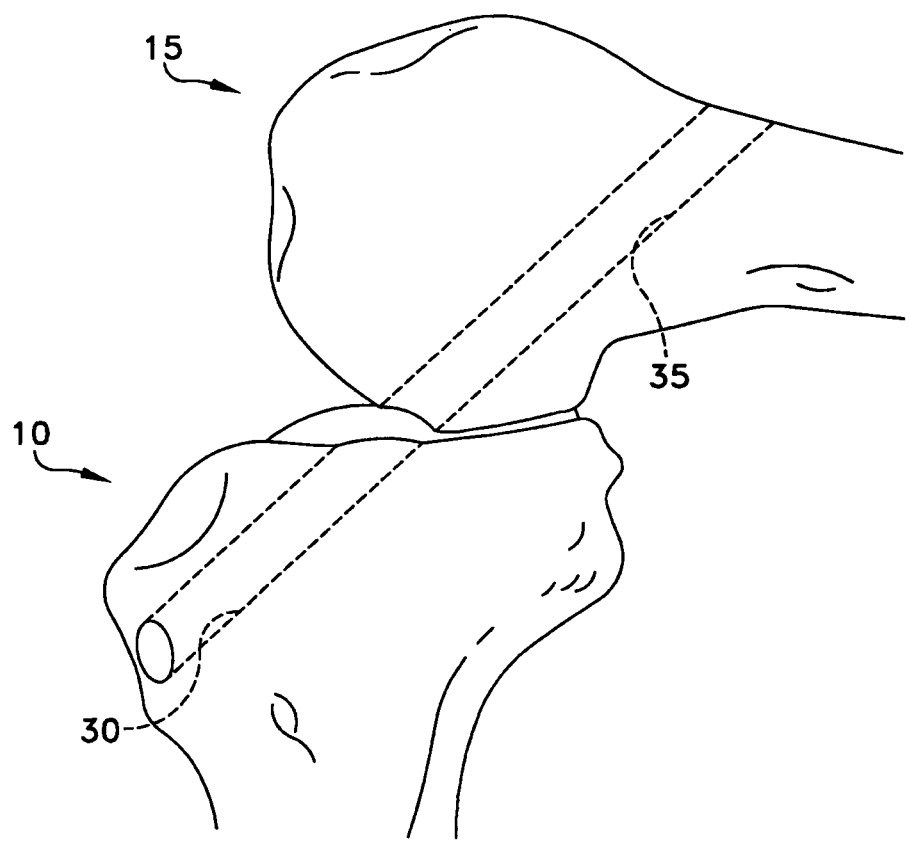
FIGS. 27-31 show a graft ligament being secured in a bone tunnel using the retainer of FIGS. 25 and 26.
Figure 28:
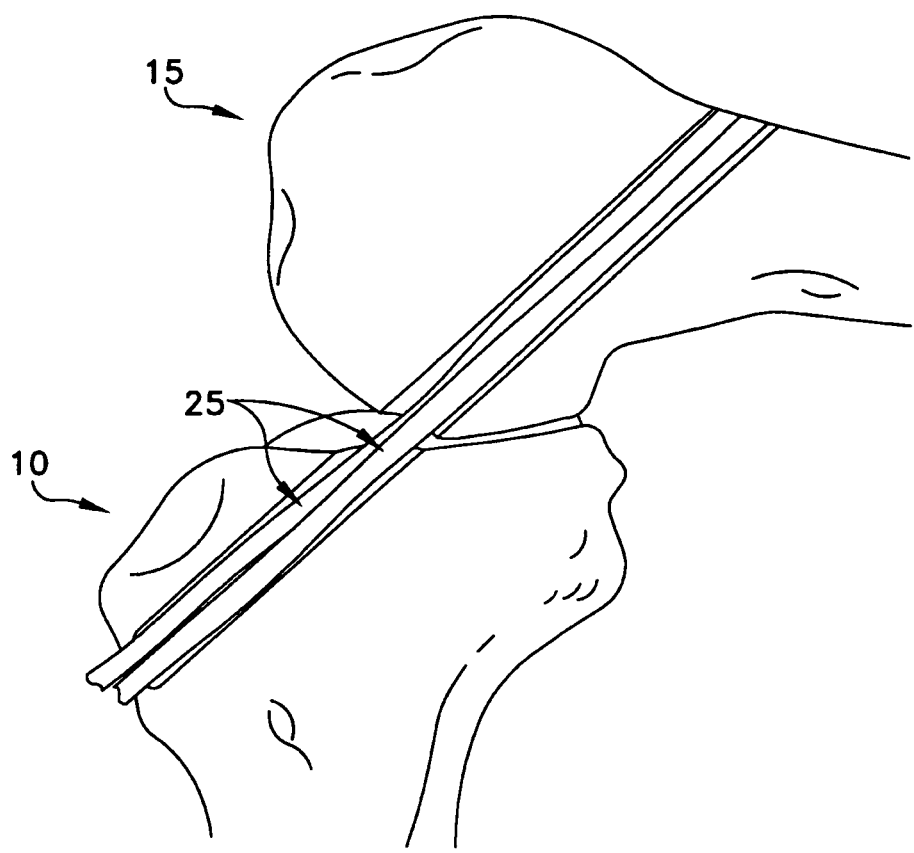
Figure 29:
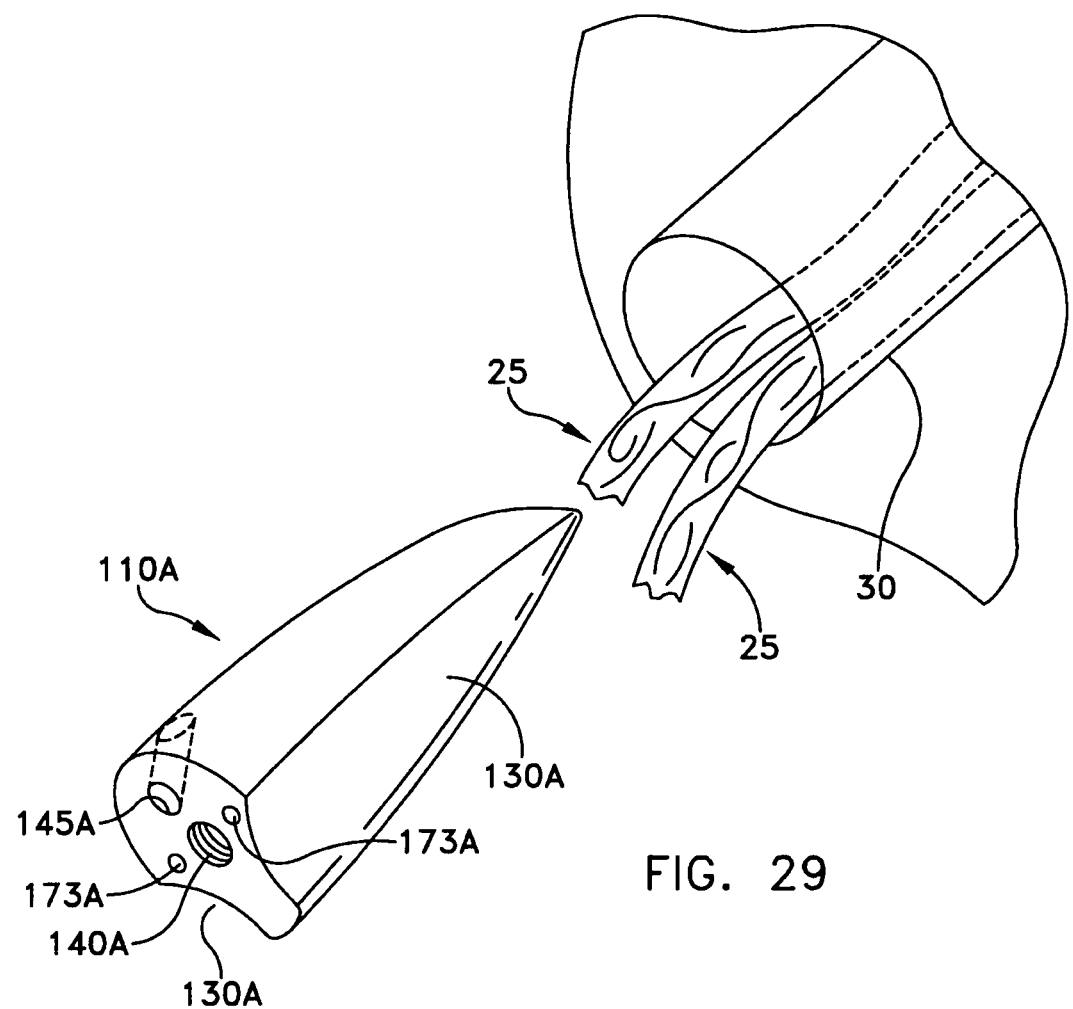
Figure 30:
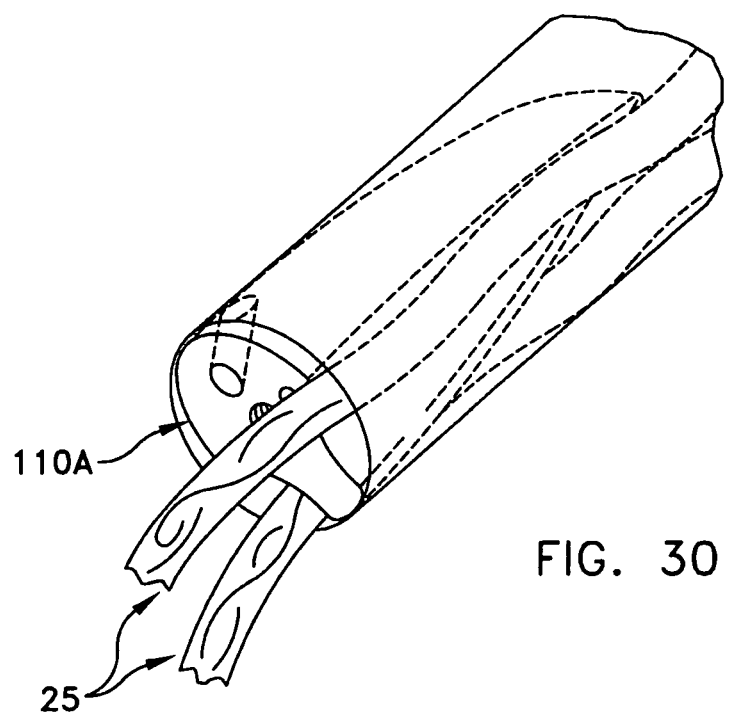
Figure 31:
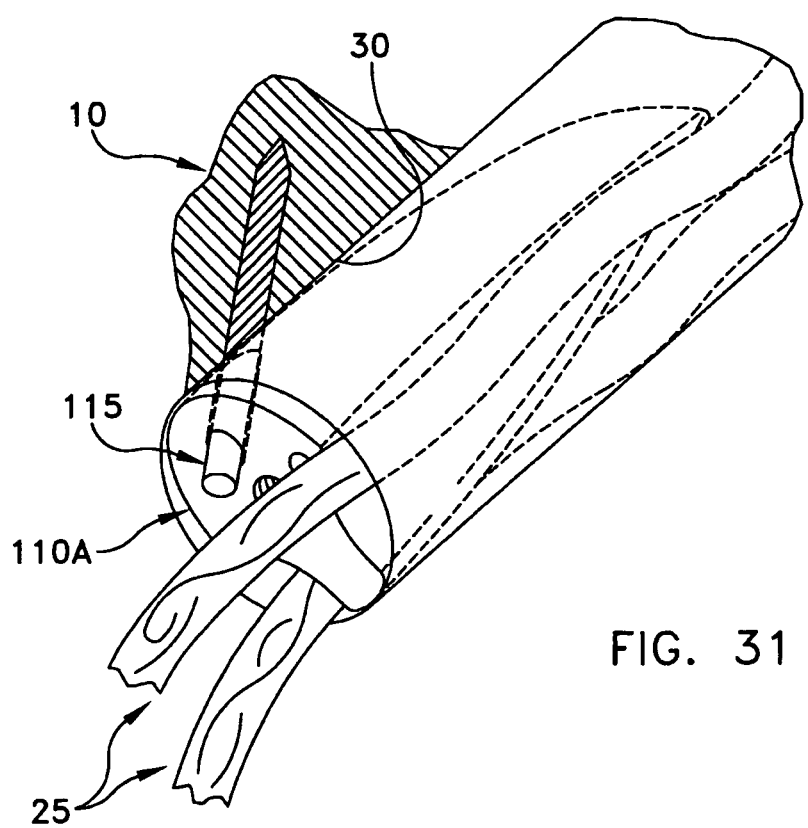

Retainer 110 can be formed with various geometries. Thus, for example, FIGS. 25 and 26 show an alternative retainer 110A which can be used where only two ligament strands are to be fixed in a bone tunnel. In this arrangement, only two grooves 130A are provided, with the remainder of retainer 110A having an arcuate peripheral surface. FIGS. 27-31 illustrate selected steps in using retainer 110A to secure graft ligament strands in a bone tunnel. While not shown in FIG. 27-31, it will be appreciated that locking cap 120 may, optionally, be used in conjunction with retainer 110A.

Figure 32:
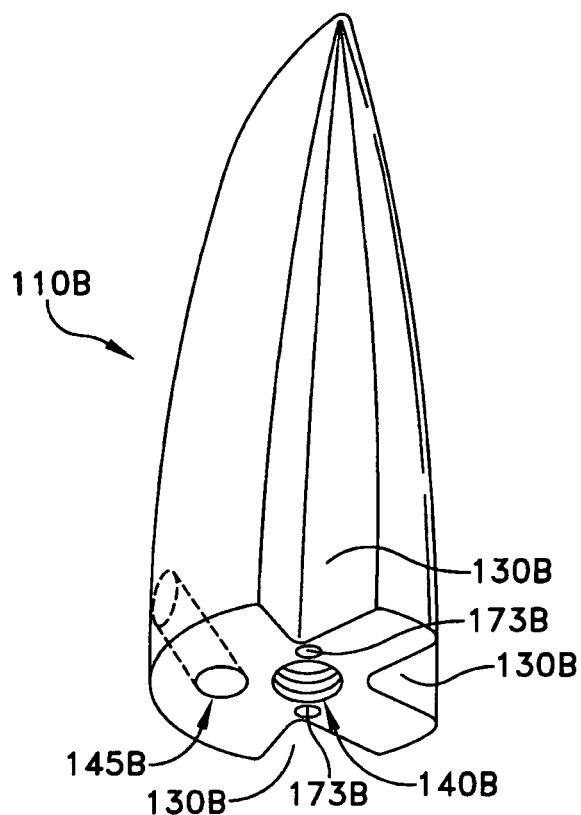
FIGS. 32 and 33 are schematic views showing a third novel retainer for use in securing a graft ligament in a bone tunnel.
Figure 33:
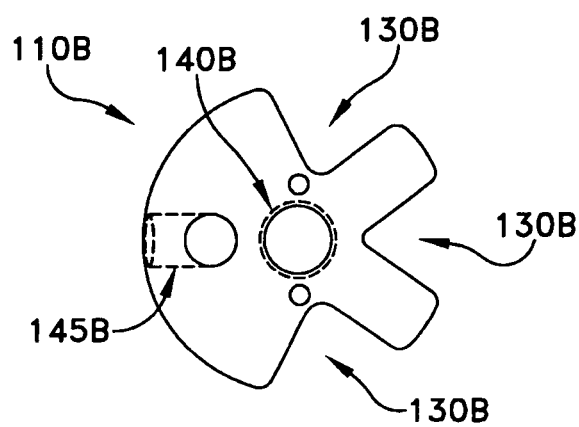

FIGS. 32 and 33 illustrate another retainer 110B. In this case, three grooves 130B are provided, to accommodate up to three ligament strands. Again, it will be appreciated that, while not shown in FIGS. 32 and 33, retainer 110B is intended to be used with locking pin 115 and, optionally, locking cap 120.

Figure 34:
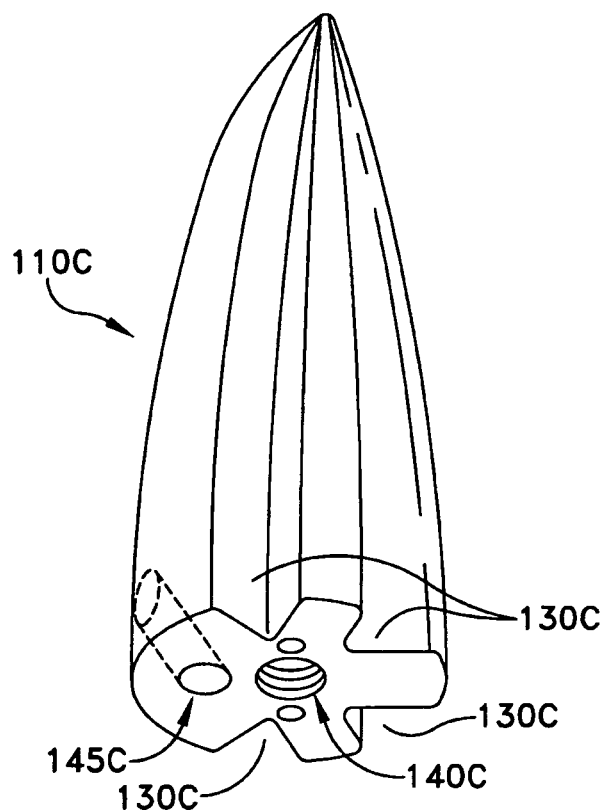
FIGS. 34 and 35 are schematic views showing a fourth novel retainer for use in securing a graft ligament in a bone tunnel.
Figure 35:
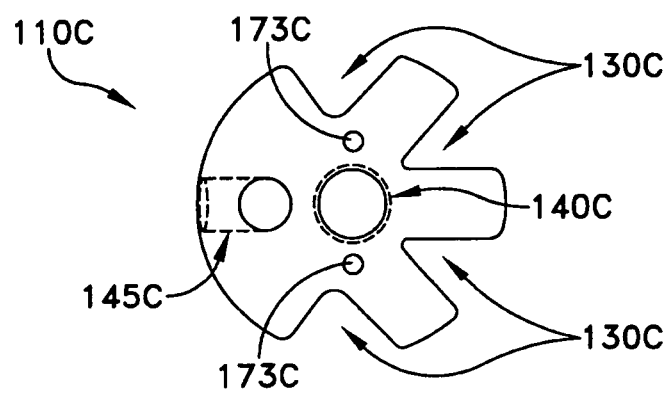

FIGS. 34 and 35 illustrate another retainer 110C. In this configuration, four grooves 130C are provided, but they are arranged in retainer 110C so that bore 145C opens on a relatively large arcuate surface. Again, it will be appreciated that, while not shown in FIGS. 34 and 35, retainer 110C is intended to be used with locking pin 115 and, optionally, locking cap 120.

Figure 36:
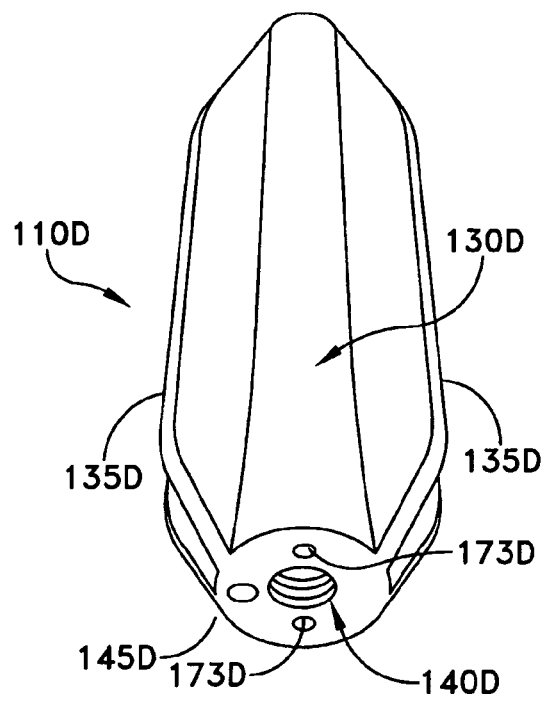
FIGS. 36-38 are schematic views showing a fifth novel retainer for use in securing a graft ligament in a bone tunnel.
Figure 37:
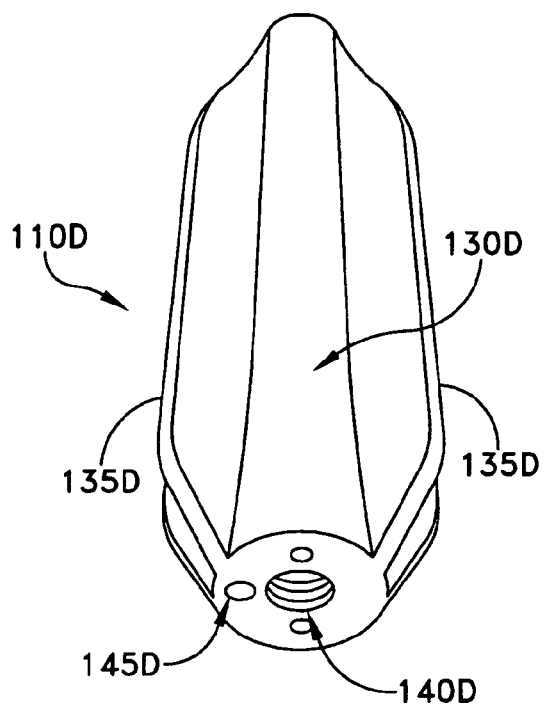
Figure 38:
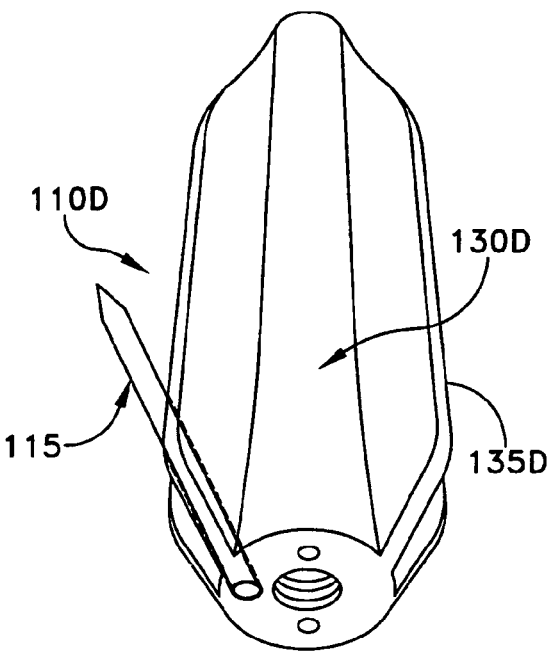

FIGS. 36-38 illustrate another retainer 110D which has a tapered proximal end as well as a tapered distal end. The tapered proximal end can permit better seating of a locking cap to the retainer. FIGS. 36 and 37 also illustrate how the height of flared fins 135D (which extend between grooves 130D) can be varied as desired. Again, it will be appreciated that, while not shown in FIGS. 36-38, retainer 110D is intended to be used, optionally, with locking cap 120.

Figure 39:
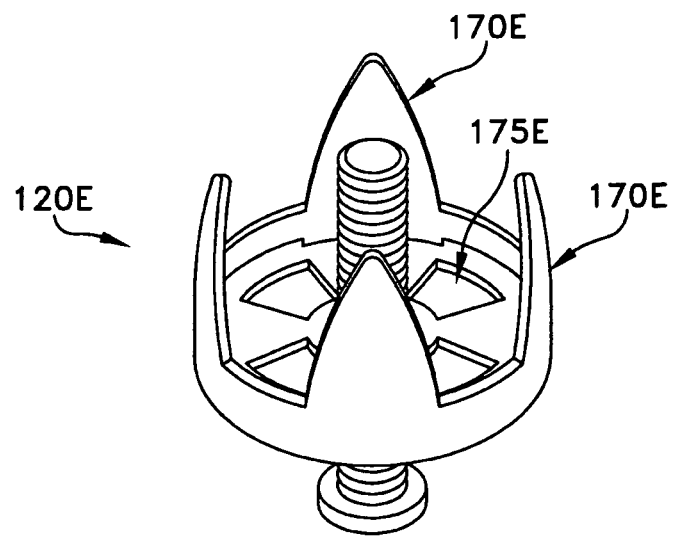
FIGS. 39 and 40 are schematic views showing additional optional locking caps for use in securing a graft ligament in a bone tunnel.
Figure 40:
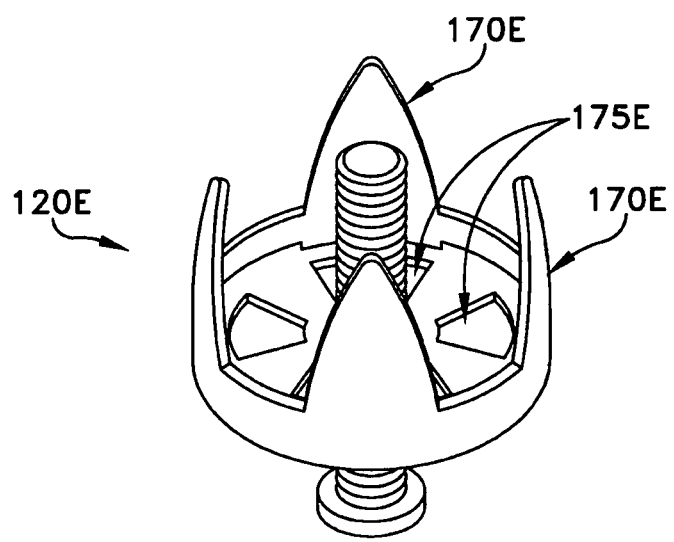

FIGS. 39 and 40 illustrate alternative locking caps 120E, where openings 175E are formed in the locking caps. Openings 175E permit graft ligament strands 25 to be folded over the proximal end surface 142 of the retainer 110 and then passed through openings 175E, thereby providing a more tortuous path for the ligament strands so as to help hold graft ligament strands 25 to retainer 110. Openings 175E can be positioned between fingers 170E (FIG. 39), or in alignment with fingers 170E (FIG. 40), and/or both.

Second Ligament Fixation System

Figure 41:
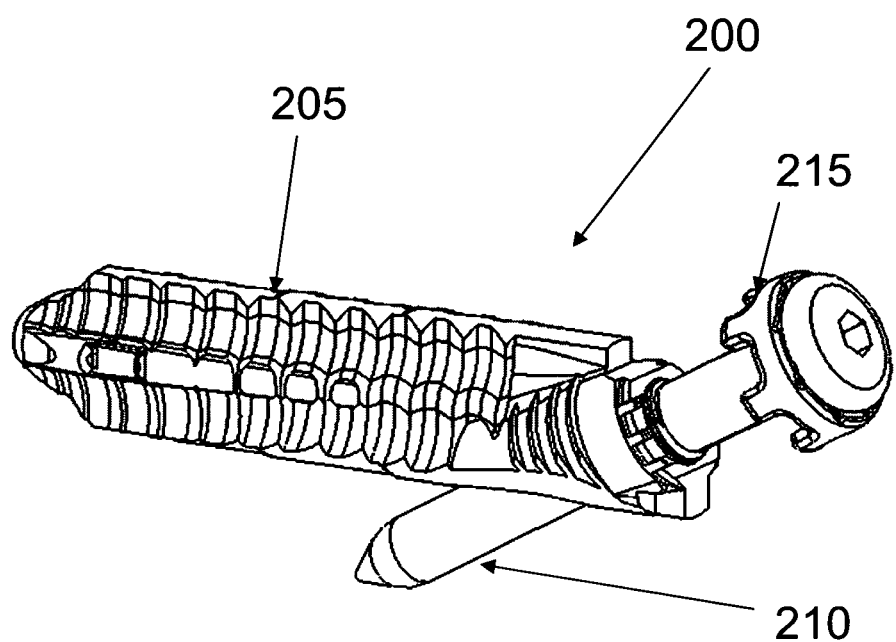
FIG. 41 is a schematic view showing another ligament fixation system formed in accordance with the present invention, wherein the ligament fixation system comprises a retainer, a locking pin and a locking cap.
Figure 41A:
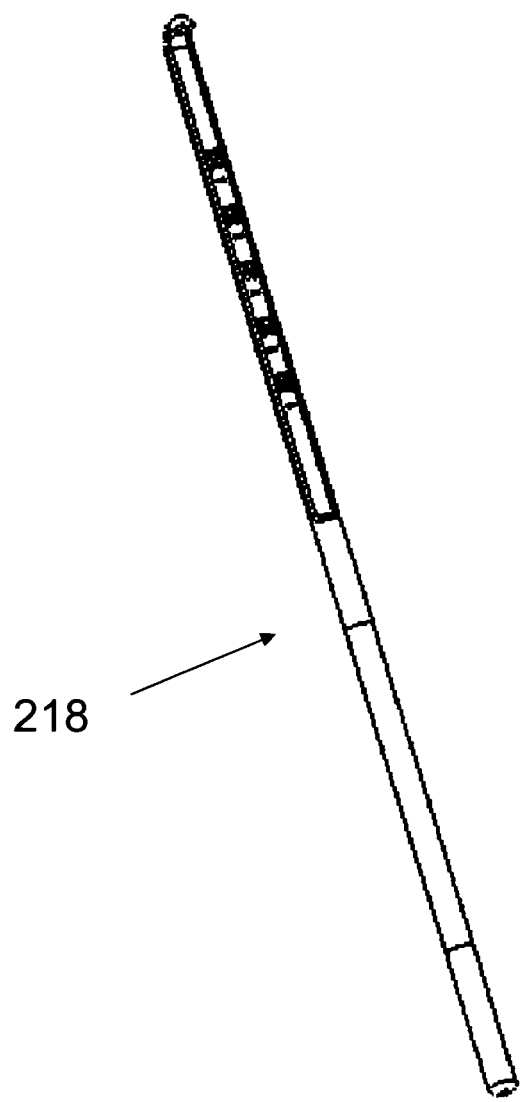
FIG. 41A is a schematic view showing a sizing wire.
Figure 42:
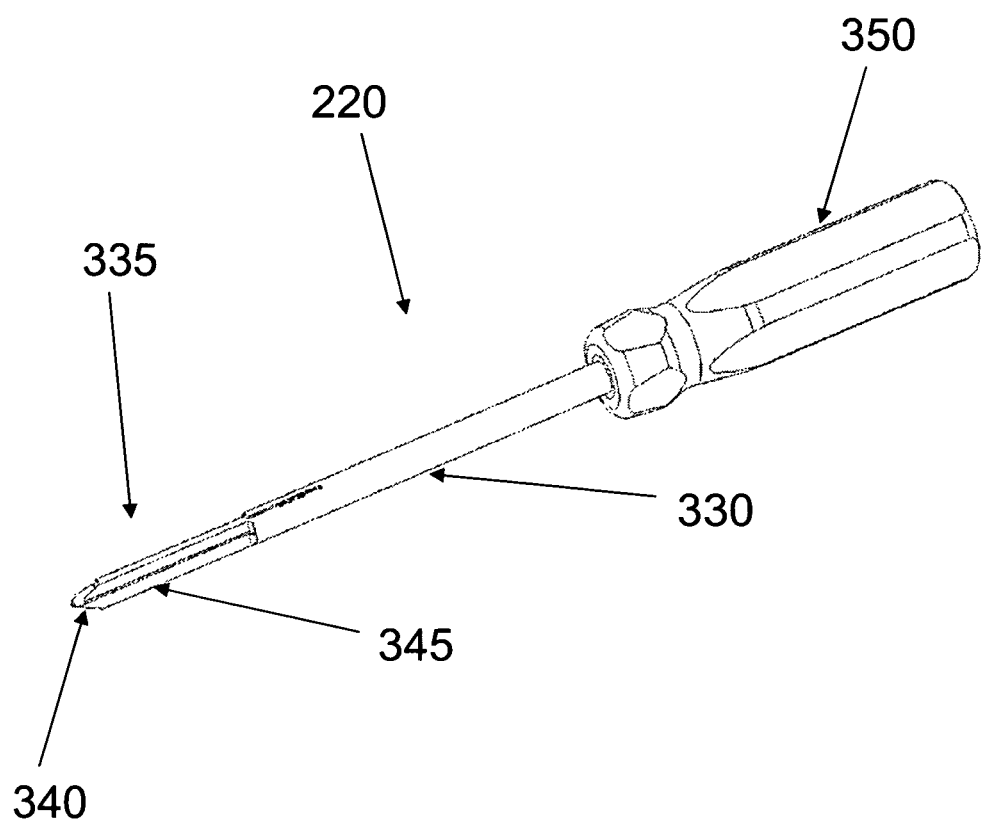
FIGS. 42 and 43 are schematic views showing a dilator formed in accordance with the present invention.
Figure 43:
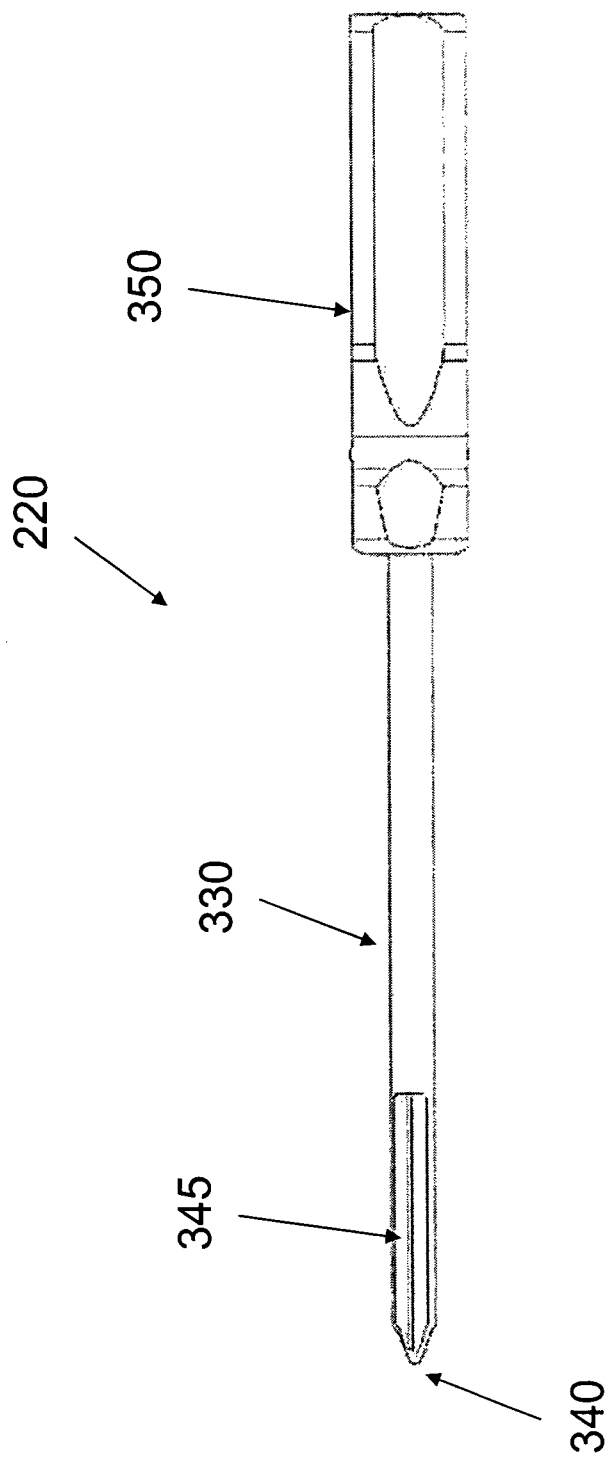

Looking next at FIG. 41, there is shown a ligament fixation system 200. Ligament fixation system 200 generally comprises a retainer 205, a locking pin 210 and a locking cap 215.

In this form of the invention, and as will hereinafter be discussed in further detail, retainer 205 is disposed in tibial tunnel 30, with graft ligament strands 25 running alongside retainer 205, whereby the graft ligament strands are compressively secured to the sidewall of tibial tunnel 30. Then locking pin 210 simultaneously pins retainer 205 to the host bone and secures locking cap 215 to retainer 205, in the process capturing graft ligament strands 25 to retainer 205 and hence additionally to the host bone.

Retainer 205, locking pin 210 and locking cap 215 are all formed out of one or more biocompatible materials. These biocompatible materials may be non-absorbable (e.g., stainless steel or plastic) or absorbable, or osteoconductive or inductive such as ceramic, allograft or coral. It should be appreciated that it is not necessary for all of the components to be formed out of the same material. In fact, each component is preferably formed out of the material or materials most advantageous for that particular component. Thus, different components may be formed out of different materials, different portions of a single component may be formed out of different materials, etc.

Retainer 205 is preferably rigid, or substantially rigid, although it may be to some extent compressive or collapsible so long as it is capable of ultimately maintaining a shape which is consistent with its intended function in the present invention. Thus, while retainer 205 is preferably rigid, or substantially rigid, retainer 205 can have any degree of rigidity which is consistent with the present invention.

In one preferred form of the invention, retainer 205 is preferably formed out of an acetyl polymer (e.g., Delrin) or PLA (polylactic acid).

Figure 44:
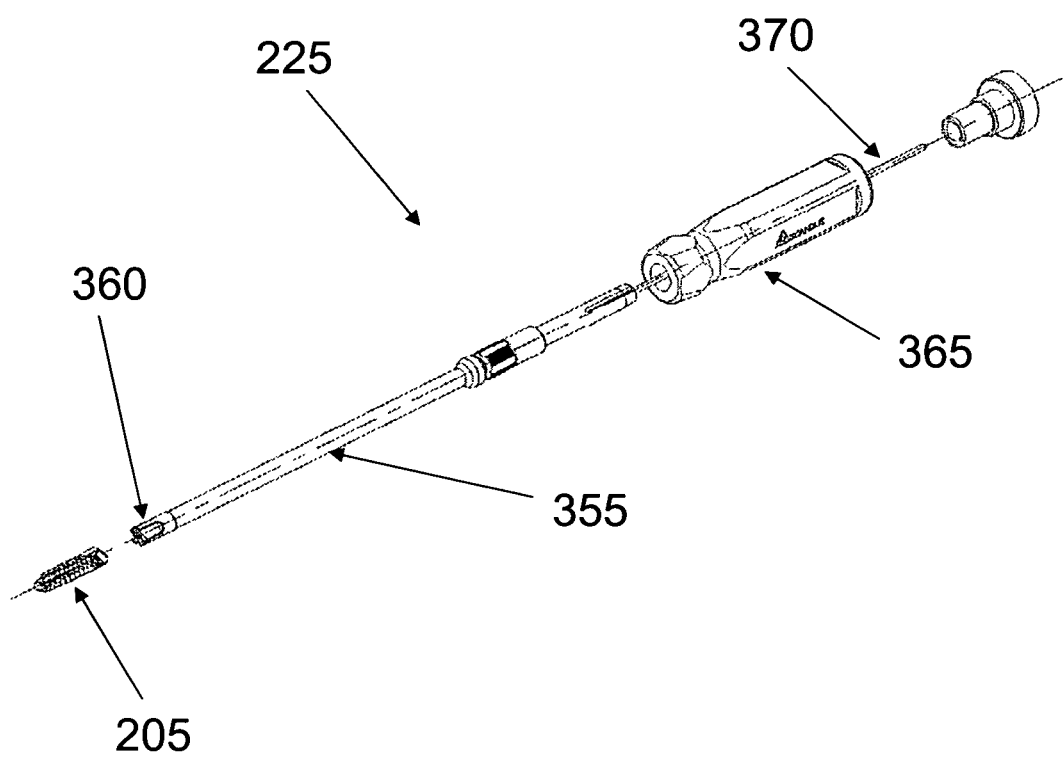
FIG. 44 is a schematic view showing an inserter formed in accordance with the present invention.

As will hereinafter also be discussed in further detail, and looking next at FIGS. 68 and 41A-44, ligament fixation system 200 also preferably comprises a sizing wire 218 (FIG. 41A), a dilator 220 (FIGS. 42 and 43) and an inserter 225 (FIG. 44). Sizing wire 218 is preferably used to measure the patient's anatomy and determine the proper size (i.e., length) of retainer 205 to be used in the ligament reconstruction procedure, as will hereinafter be discussed in further detail. Dilator 220 is preferably used to prepare bone tunnel 30 and graft ligament strands 25 prior to deploying retainer 205 in the bone tunnel, as will also hereinafter be discussed. Inserter 225 is preferably used to deploy retainer 205 within bone tunnel 30, as will also hereinafter be discussed.

Figure 45:
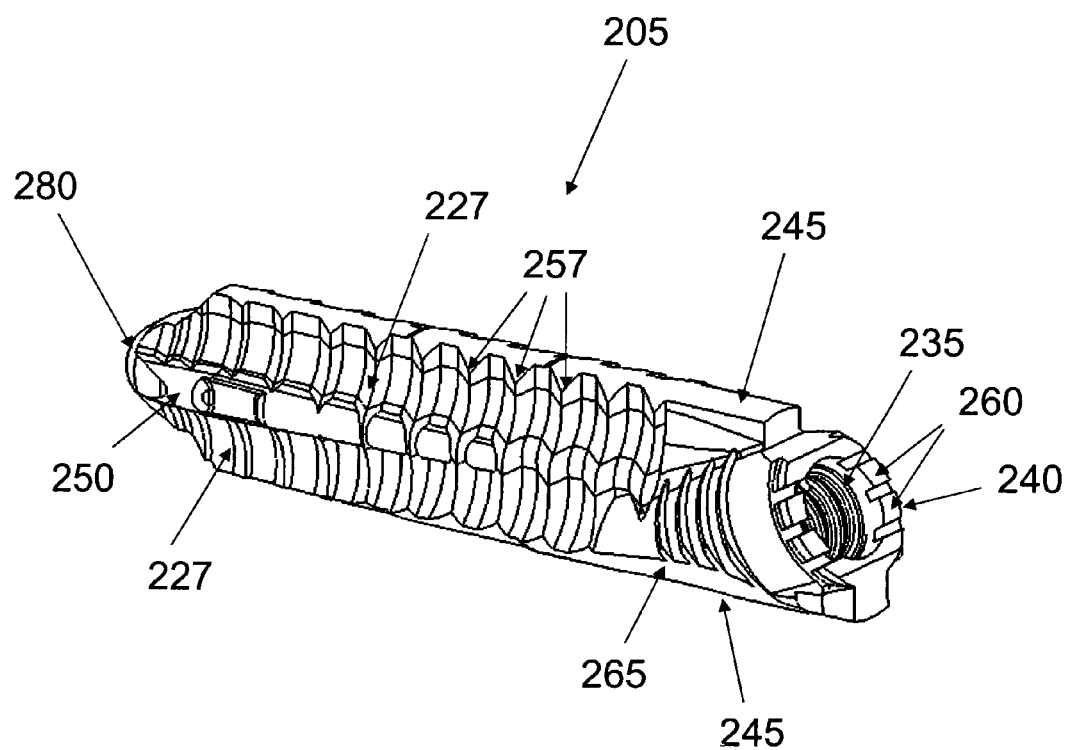
FIGS. 45-52 and 52A-52E are schematic views showing further details of the retainer of the ligament fixation system shown in FIG. 41.
Figure 46:
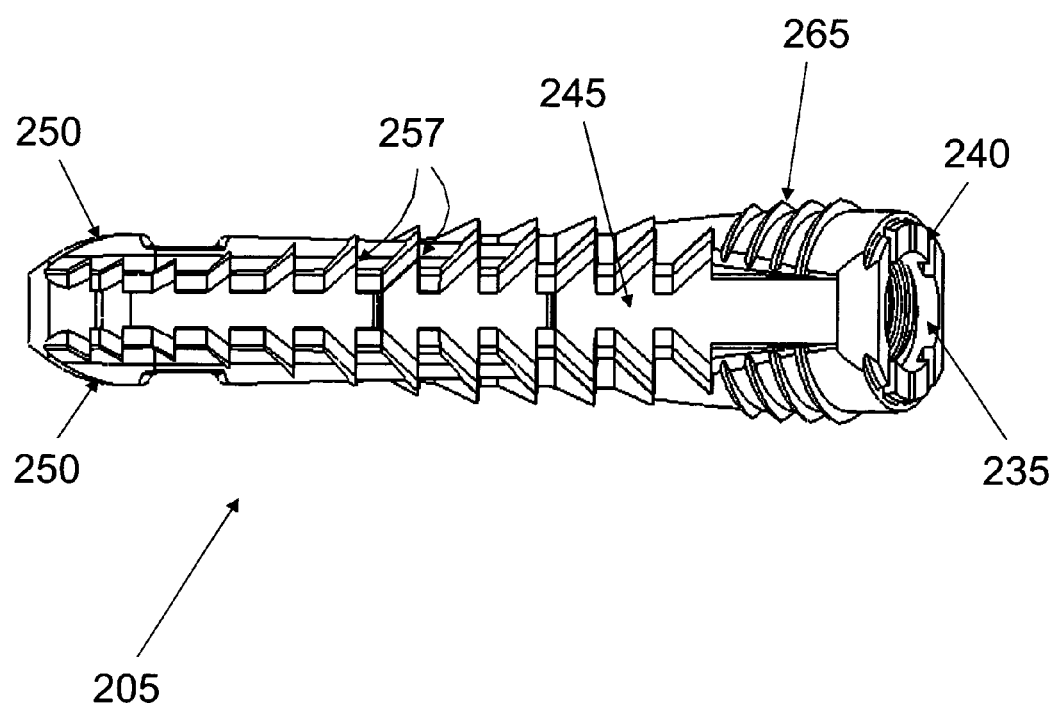
Figure 47:
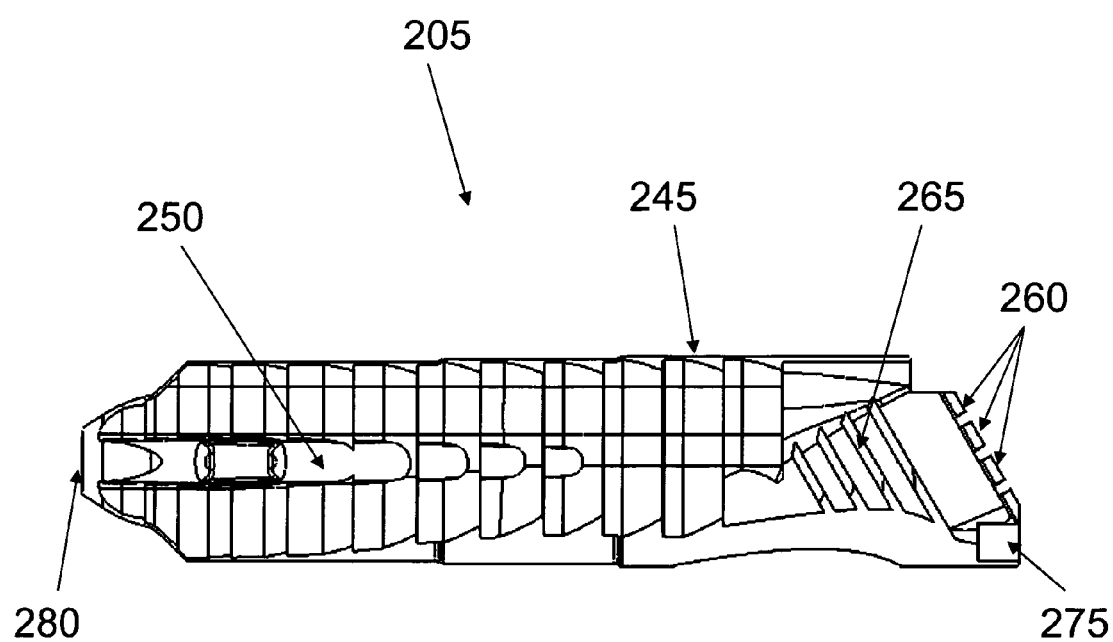
Figure 48:
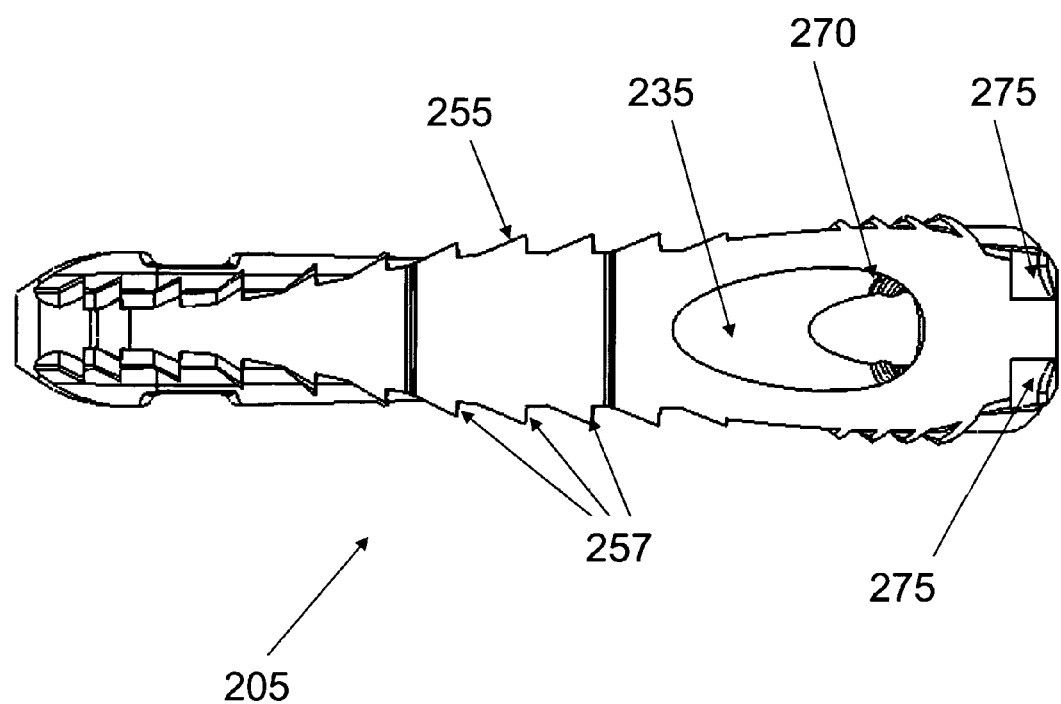
Figure 49:
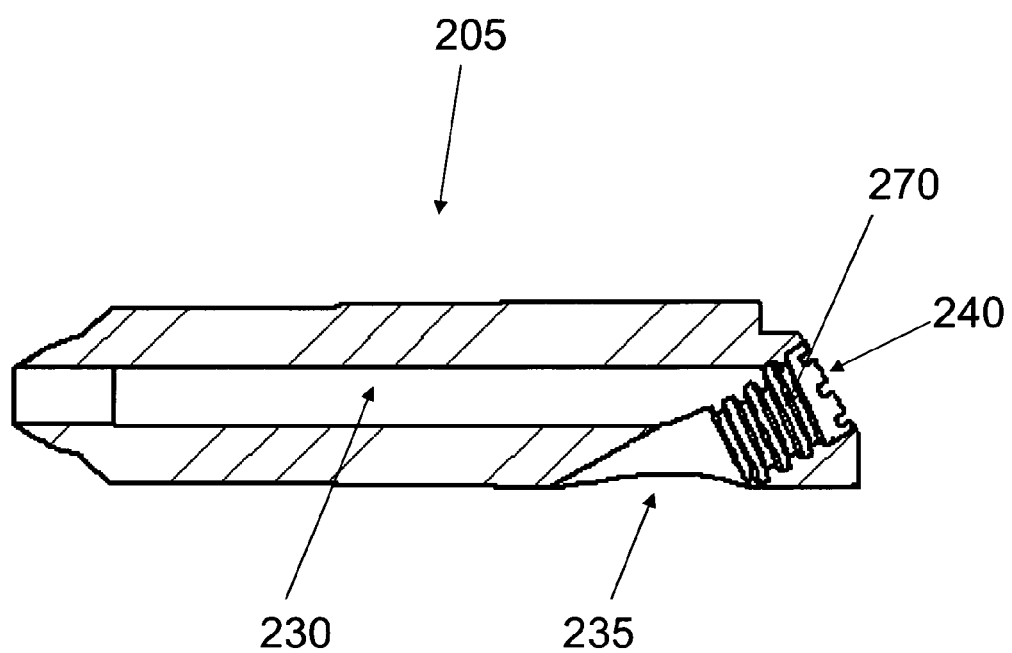
Figure 50:
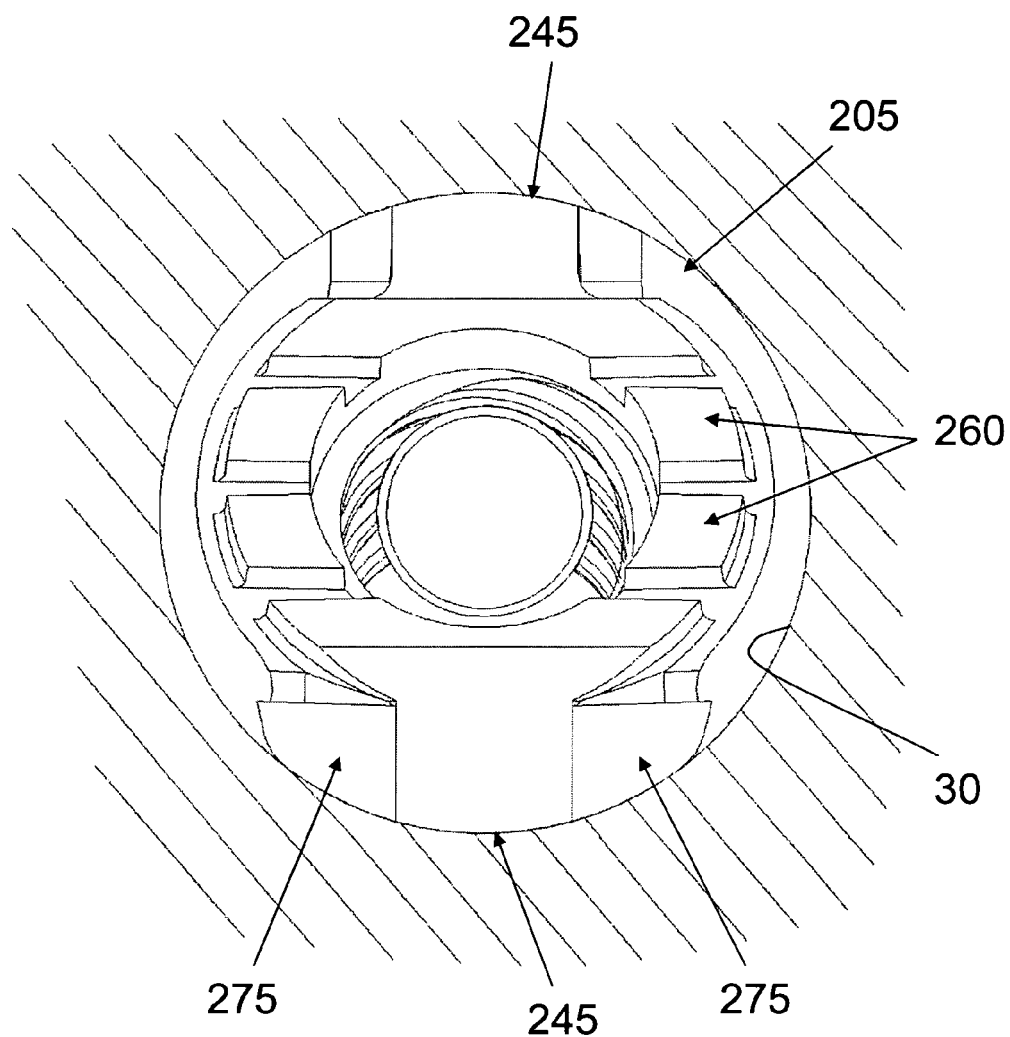
Figure 51:
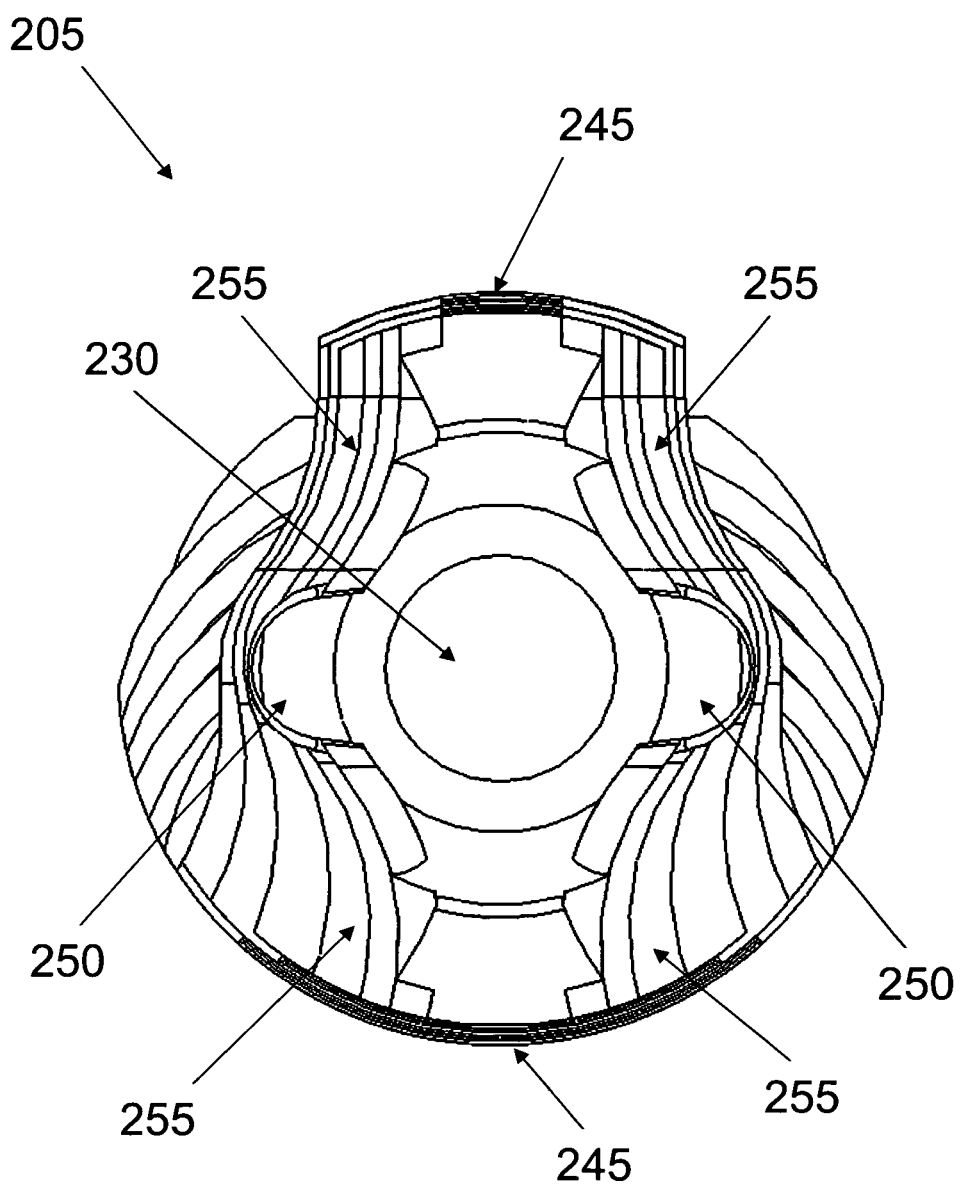
Figure 52:
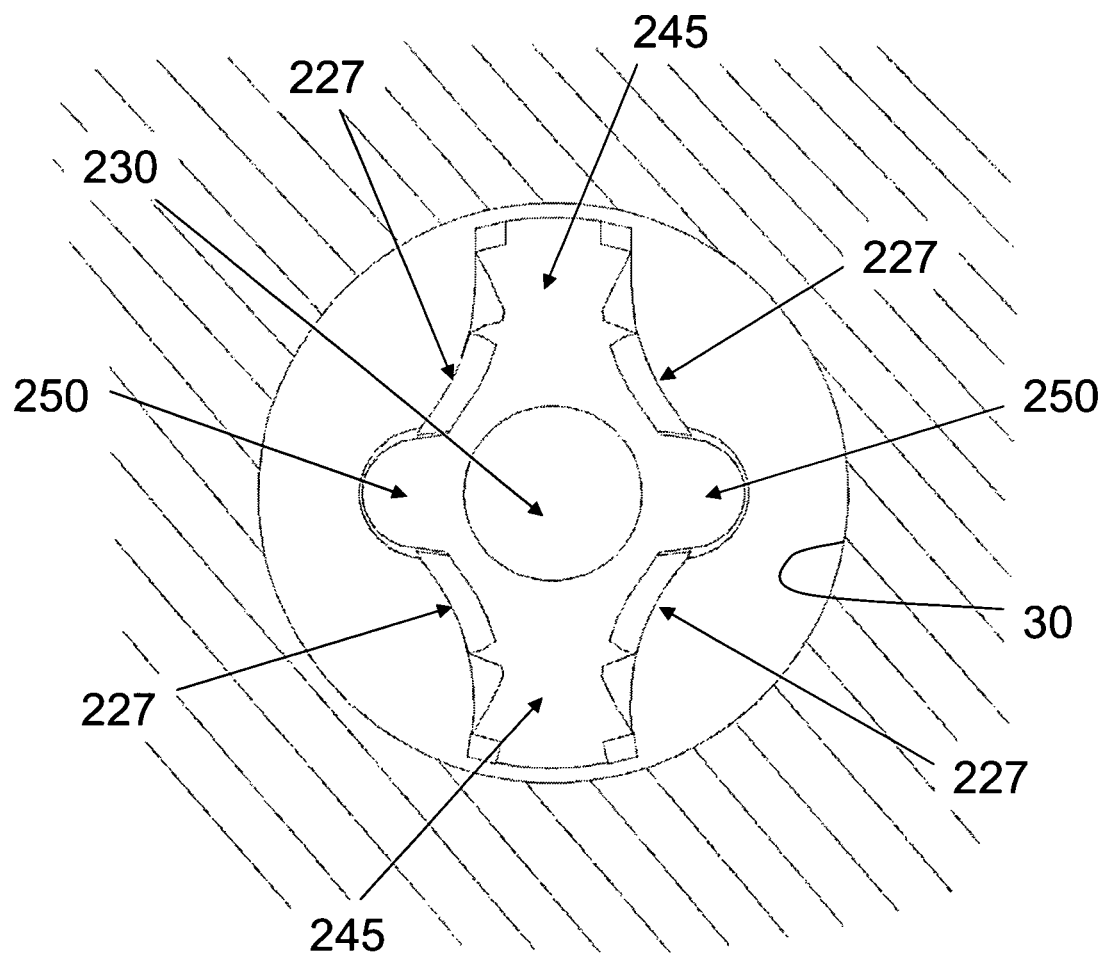
Figure 52A:
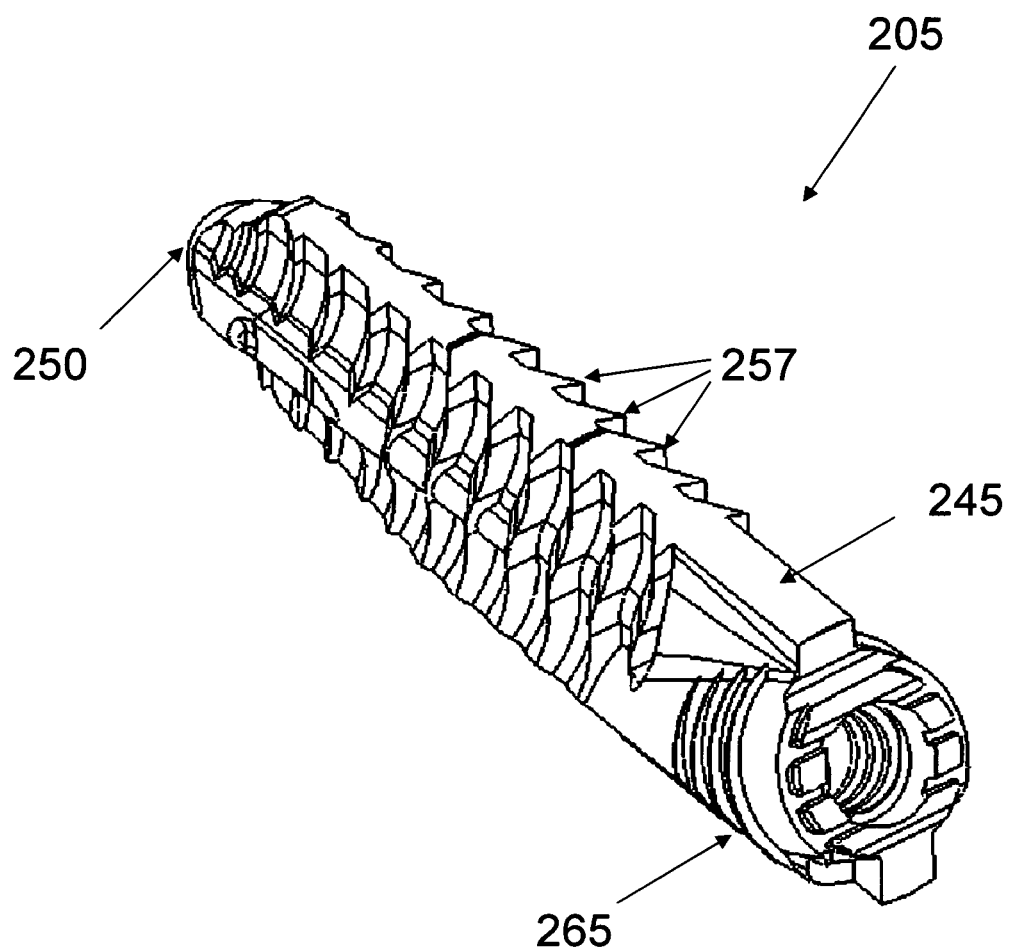
Figure 52B:
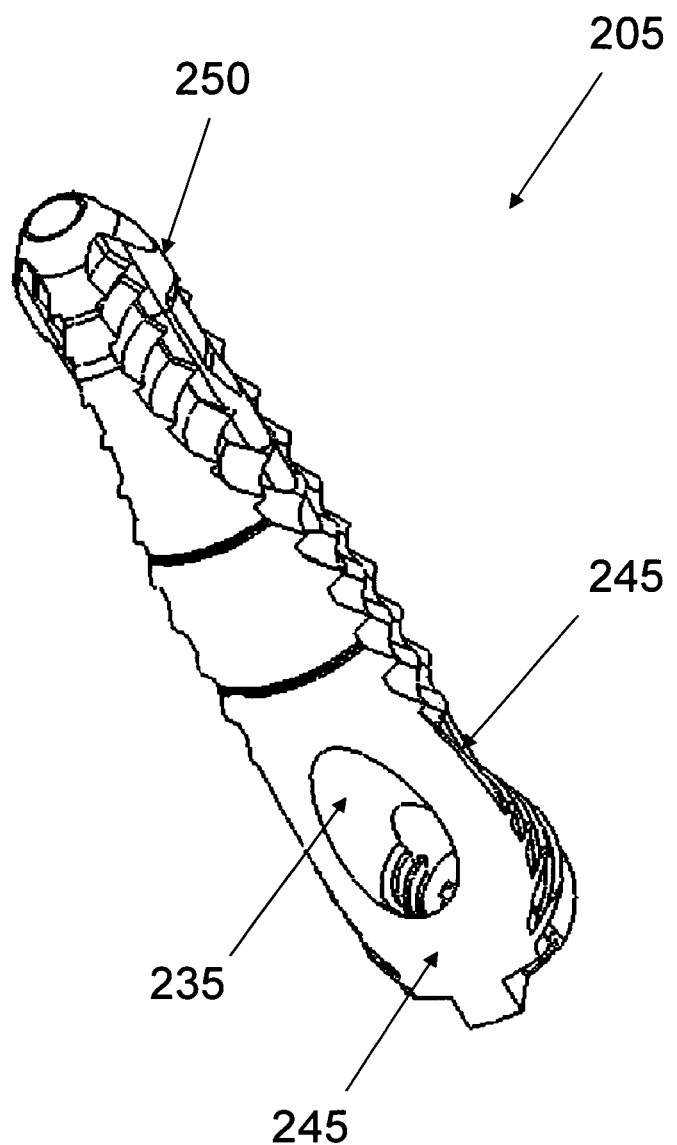
Figure 52C:
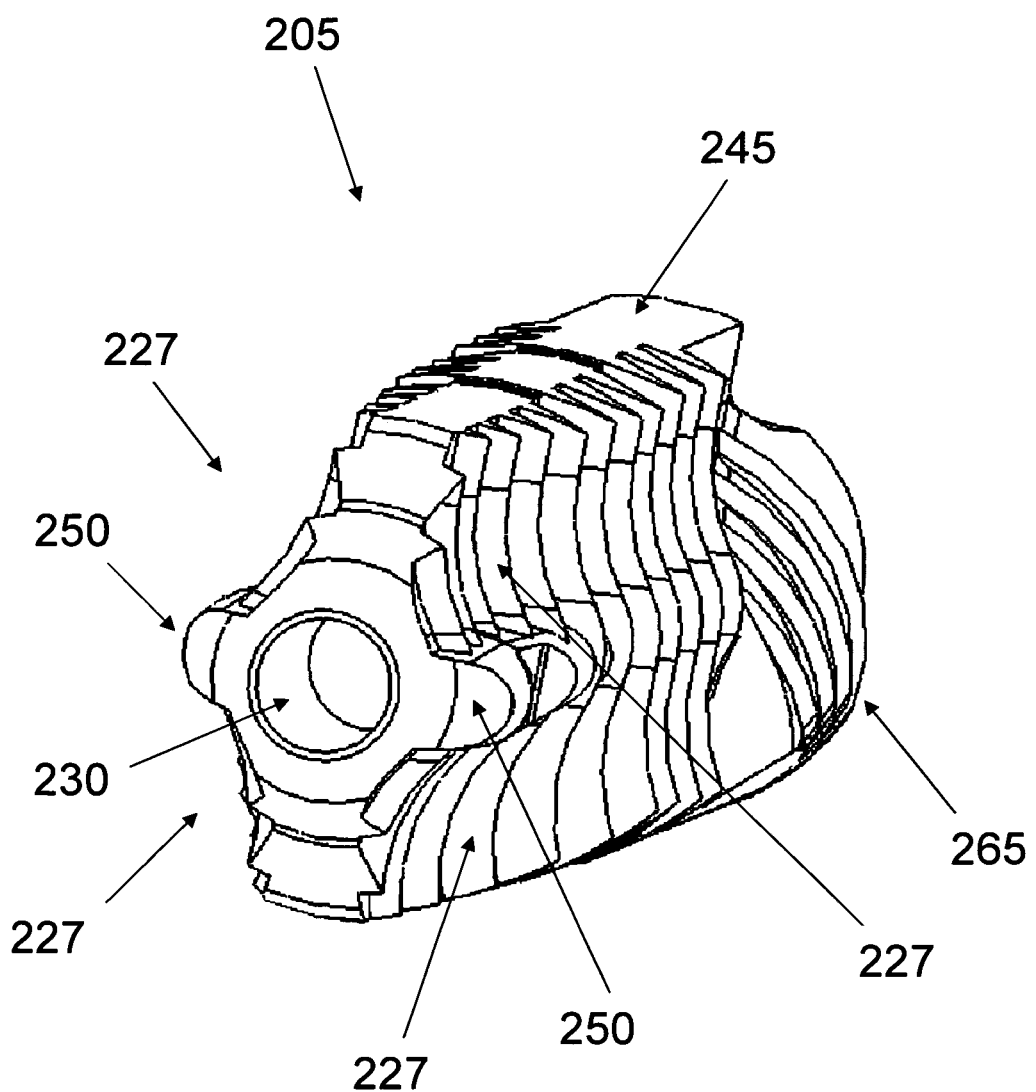
Figure 52D:
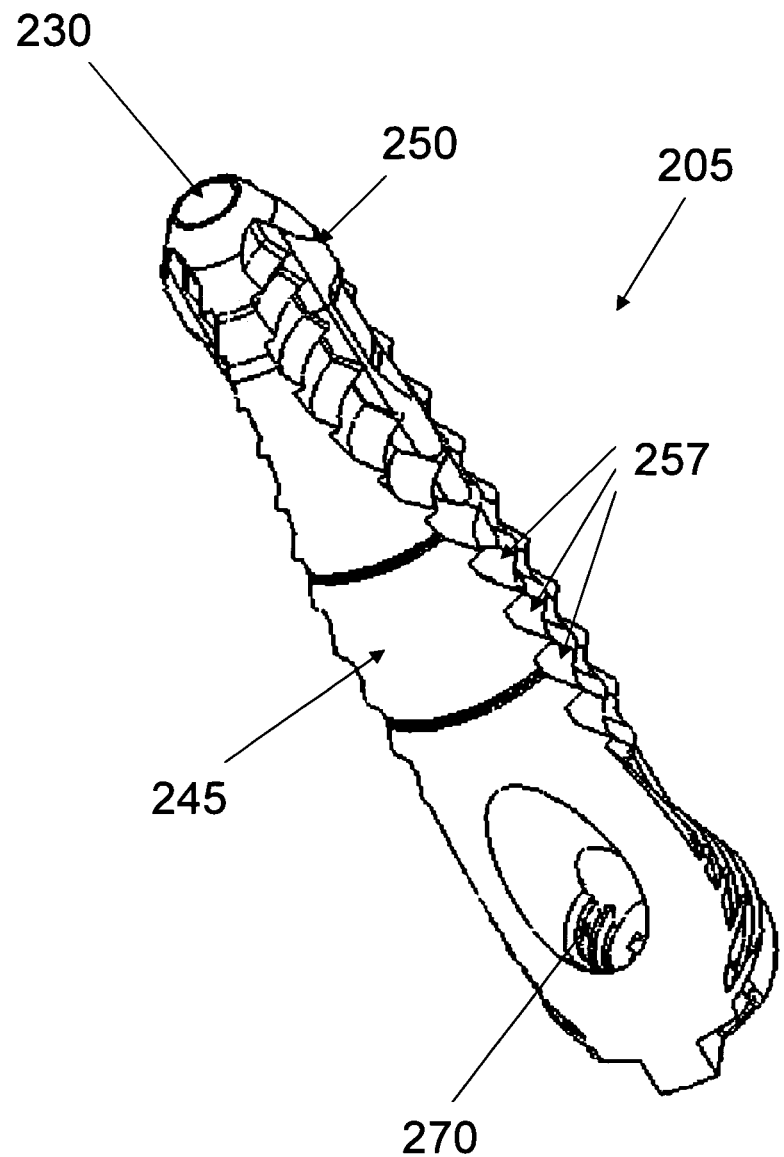
Figure 52E:
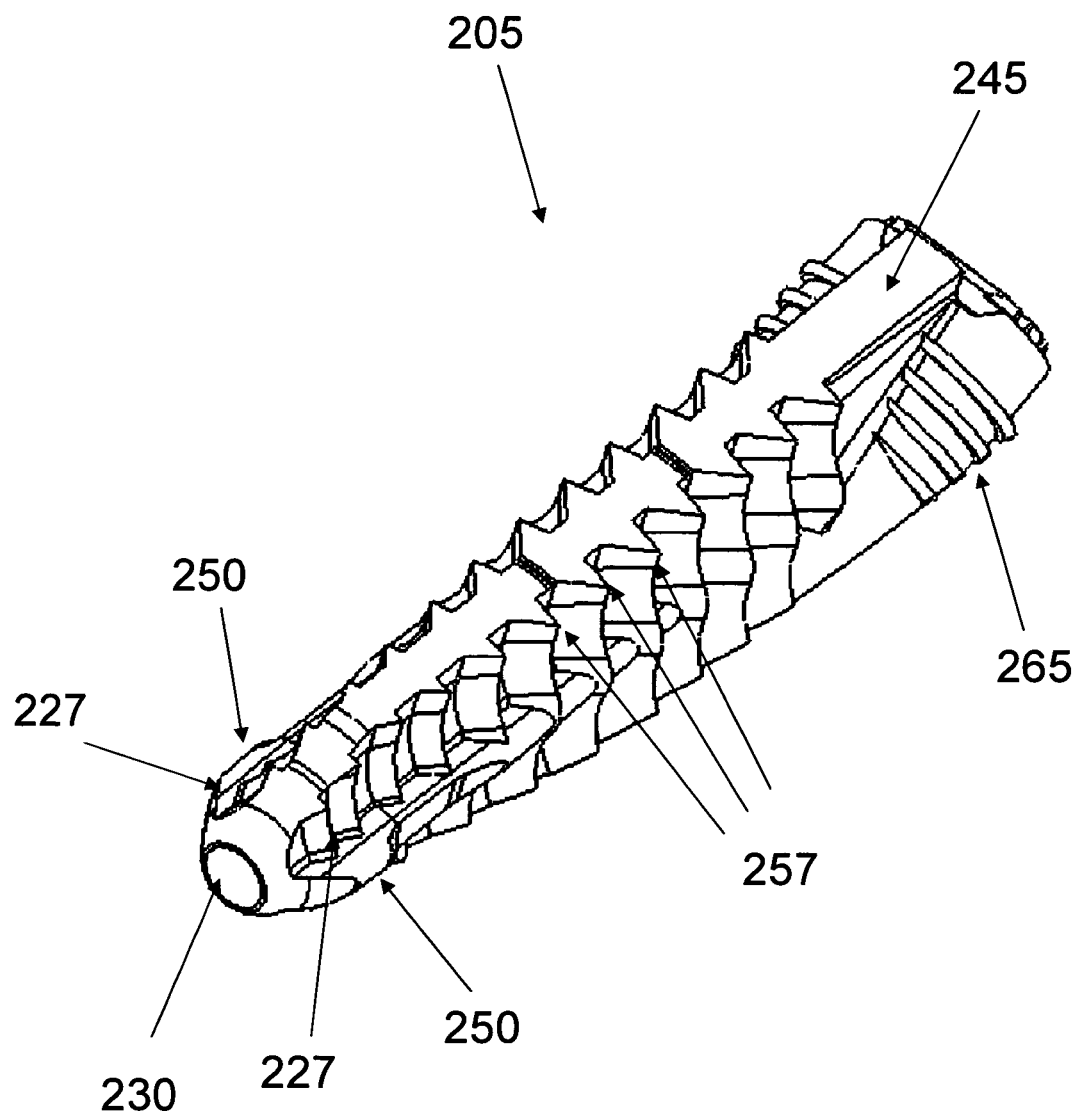

Retainer 205 of ligament fixation system 200 is shown in further detail in FIGS. 45-52 and 52A-52E. Retainer 205 generally comprises four longitudinally-extending grooves 227 (FIGS. 45 and 52) for receiving graft ligament strands 25, a central lumen 230 (FIG. 49) for receiving a portion of inserter 225 as will hereinafter be discussed, a crosshole 235 for receiving locking pin 210, and a mounting shoulder 240 for seating graft ligament strands 25 and locking cap 215.

In addition to the foregoing, retainer 205 preferably also comprises two main ribs or spines 245 (FIGS. 45, 50 and 52), two lateral fins 250 (FIGS. 45, 47, 51 and 52), a lofted profile 255 to the floors of grooves 227 (FIGS. 48 and 51), a plurality of ribs 257 (FIGS. 45, 46 and 48) formed on the floors of the longitudinally-extending grooves 227, locking profiles 260 formed on the face of mounting shoulder 240 (FIGS. 45, 47 and 50), side ribs 265 (FIGS. 45 and 47), internal screw threads 270 formed on the interior of crosshole 235 (FIGS. 48 and 49), recesses 275 formed on the rear end of retainer 205 (FIGS. 47, 48 and 50) for engagement by inserter 225, and stepped pointed tip 280 (FIGS. 45 and 47), each of which are discussed in greater detail below.

Main ribs or spines 245 (FIGS. 45, 50 and 52) extend down the length of retainer 205 and, when retainer 205 is deployed in the bone tunnel along with a plurality of graft ligament strands, spines 245: (i) securely seat on the sidewall of the bone tunnel, and (ii) help keep the ligament strands aligned with the longitudinal axis of retainer 205.

Lateral fins 250 (FIGS. 45, 47, 51 and 52) help, in conjunction with spines 245, separate graft ligament strands 25 into separately manageable lengths and position those graft ligament strands in the four longitudinally-extending grooves 227 when retainer 205 is introduced into the bone tunnel. To the extent that the graft ligament comprises just two strands rather than four strands (e.g., a tibialis tendon graft), the two lateral fins lie against the two graft ligament strands and apply an additional lateral compressive force. In this respect it should be appreciated that where the system 200 is used with just two ligament strands, dilator 220 prepares those two strands by forming impressions in the strands to receive the lateral fins.

Lofted profile 255 (FIGS. 48 and 51) provides a pressure gradient for the graft ligament strands 25 extending alongside the length of retainer 205. More particularly, lofted profile 255 provides progressively greater compression (in a distal-to-proximal direction) of graft ligament strands 25 against the sidewall of the bone tunnel and, in turn, develops gentle ligament-to-bone contact near the distal end of retainer 205 and more aggressive ligament-to-bone contact near the proximal end of retainer 205. The increased compression (from the distal end to the proximal end) provides good circumferential ligament coverage around the perimeter of bone tunnel 30 and generates excellent fixation strength. The lofted profile 255, which provides retainer 205 with a generally tapered configuration, also facilitates insertion of retainer 205 into bone tunnel 30.

Ribs 257 (FIGS. 45, 46 and 48) are formed on the floors of the longitudinally-extending grooves 227, and serve to inhibit longitudinal movement of graft ligament strands 25 relative to retainer 205 when the graft ligament strands are seated in the longitudinally-extending grooves, as will hereinafter be discussed.

Locking profiles 260 (FIGS. 45, 47 and 50) interact with complementary profiles formed on locking cap 215 (hereinafter discussed) so as to facilitate gripping of graft ligament strands 25 between mounting shoulder 240 (FIG. 45) and the underside of locking cap 215, as will hereinafter be discussed.

Side ribs 265 (FIGS. 45 and 47) provide extra grip for graft ligament strands on the proximal (i.e., non-joint) end of retainer 205.

Figure 53:
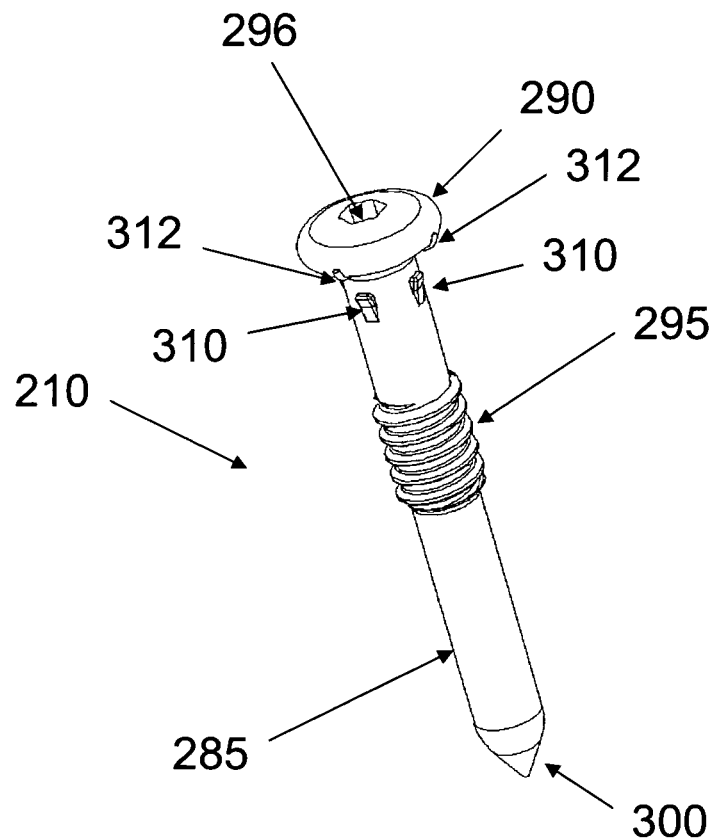
FIGS. 53-56 are schematic views showing further details of the locking pin of the ligament fixation system shown in FIG. 41.
Figure 54:
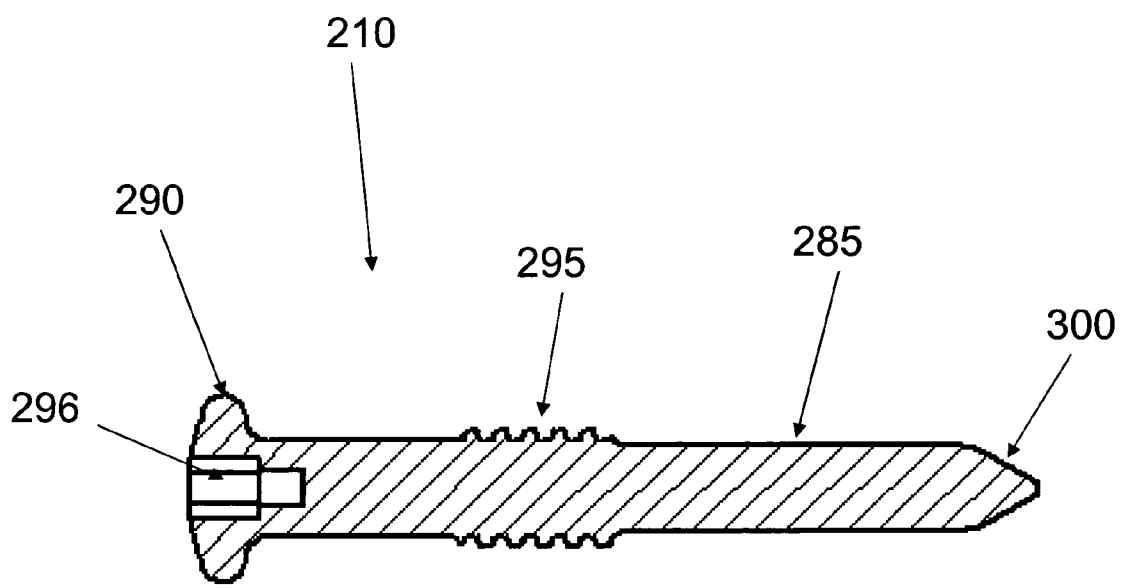
Figure 55:
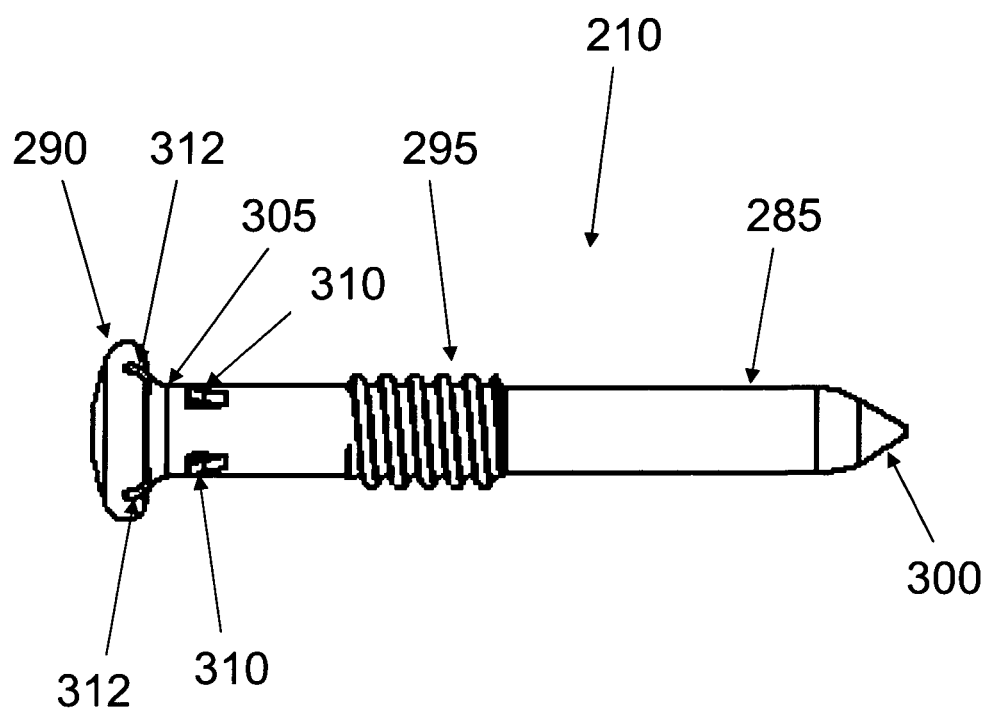
Figure 56:
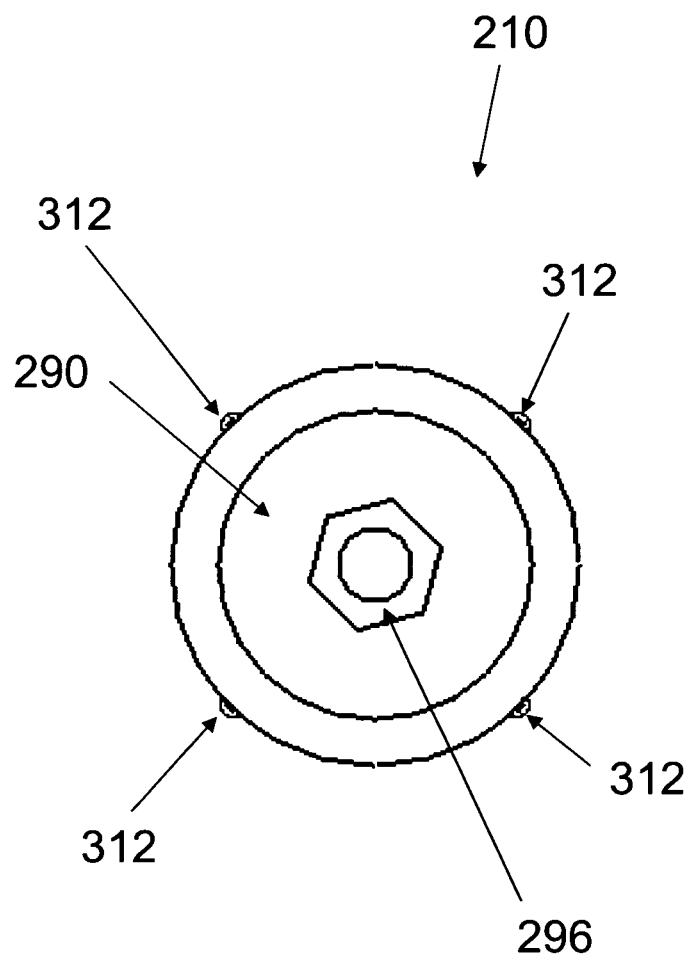
Figure 57:
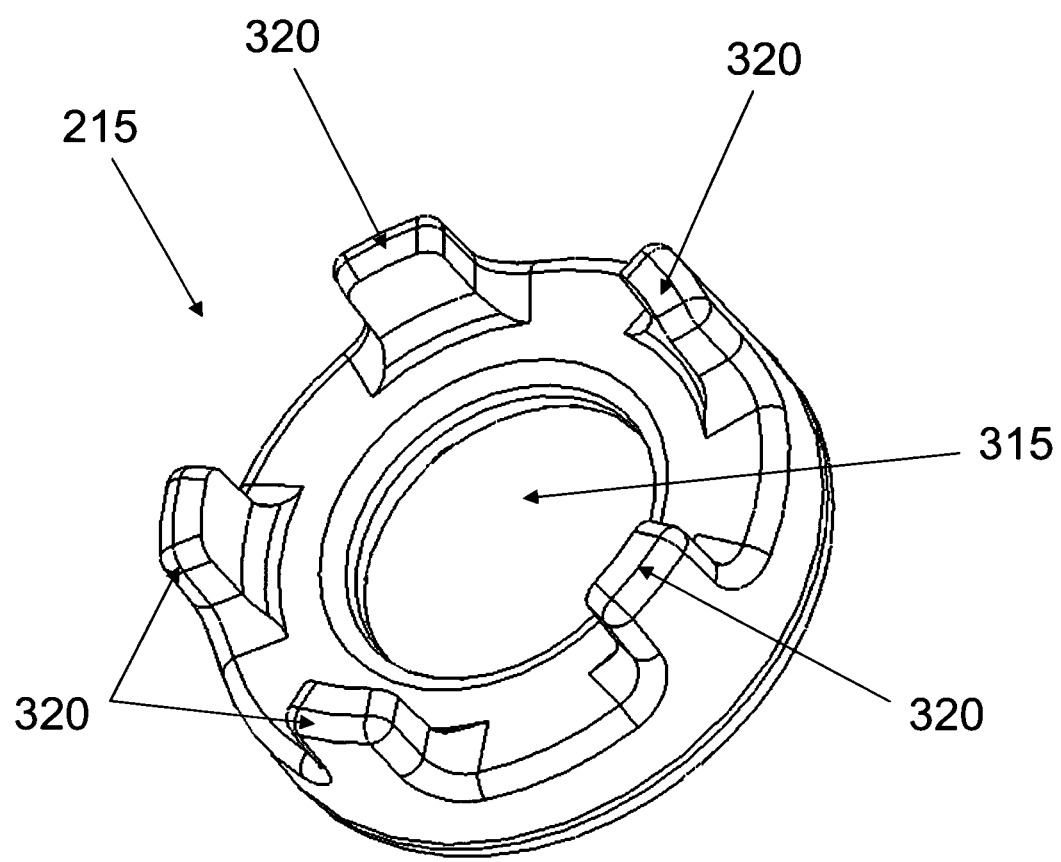
FIGS. 57-61 are schematic views showing further details of the locking cap of the ligament fixation system shown in FIG. 41.
Figure 58:
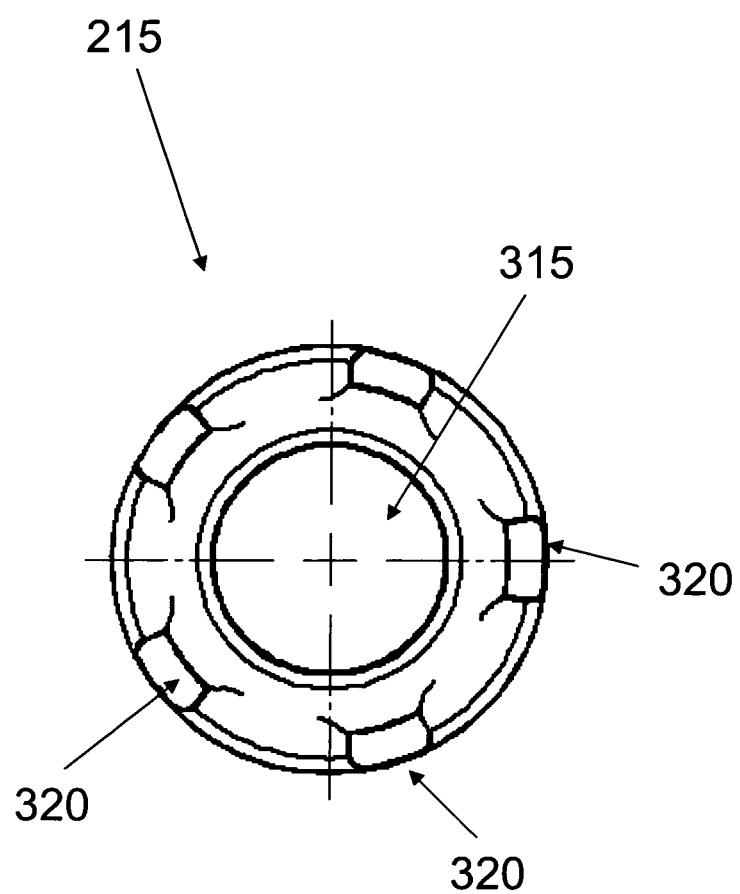

Internal screw threads 270 (FIGS. 48 and 49) mate with counterpart threads 295 (FIG. 53) formed on locking pin 210, whereby to facilitate controlled advancement of locking pin 210 through crosshole 235, as will hereinafter be discussed.

Recesses 275 (FIGS. 47, 48 and 50) mate with counterpart elements on inserter 225, as will hereinafter be discussed, whereby to help hold retainer 205 to the inserter.

Stepped pointed tip 280 (FIGS. 45 and 47) provides a tortuous path for graft ligament strands 25 as they pass by retainer 205, so as to help secure graft ligament strands 25 within the bone tunnel. The profile of stepped pointed tip 280 creates additional wedging between retainer 205 and the sidewall of the tapered bone tunnel (i.e., along spines 245) in the event that retainer 205 tries to move beyond its intended depth.

It should be appreciated that the dimensions of retainer 205 are chosen so that when retainer 205 is disposed in bone tunnel 30 (i.e., after bone tunnel 30 and graft ligament strands 25 are prepared by the dilator 220), retainer 205 will wedge firmly into position in bone tunnel 30 against both graft ligament strands 25 and the sidewall of bone tunnel 30.

Locking pin 210 is shown in further detail in FIGS. 53-56. Locking pin 210 generally comprises a shaft 285 for insertion through locking cap 215, retainer 205 and into the host bone, a head 290 for securing locking cap 215 against retainer 205 so as to capture the graft ligament strands 25 to the retainer, and threads 295 for engagement with counterpart internal screw threads 270 on retainer 205 the controlled advancement of locking pin 210 relative to retainer 205, as will hereinafter be discussed in further detail. Head 290 also preferably comprises a non-circular (e.g., hexagonal, Torx, Phillips, star, etc.) recess 296 for selective mating with a driver (not shown), whereby to facilitate turning of locking pin 210.

Locking pin 210 also preferably comprises a tapered distal tip 300, one or more shaft enlargements 310, and a locking cap seat 305 (FIG. 55) located between head 290 and the one or more shaft enlargements 310, each of which is discussed in greater detail below.

Threads 295 are located on shaft 285 and mate with counterpart threads 270 on retainer 205 for controlled advancement of locking pin 210 through crosshole 235 of retainer 205. In one preferred embodiment, threads 295 on locking pin 210, and counterpart threads 270 on retainer 205, are sized so as to protect the user from overtightening locking pin 210 relative to retainer 205.

Tip 300, at the distal end of shaft 285, is preferably pointed and smooth so as to facilitate passage of locking pin 210 through crosshole 235 in retainer 205 and into the host bone.

Locking cap seat 305 (FIG. 55) is located between head 290 and the one or more shaft enlargements 310, whereby to permit locking cap 215 (FIG. 41) to slip proximally over the one or more shaft enlargements 310 and then be loosely held to shaft 285 prior to secure tightening of locking pin 210 vis-à-vis retainer 205, whereby to secure locking cap 215 against the retainer's mounting shoulder 240.

In one preferred form of the invention, locking pin 210 also includes a plurality of projections 312 (FIGS. 53, 55 and 56) for engaging corresponding elements on locking cap 215 whereby to provide an anti-backout feature, as will hereinafter be discussed in further detail.

Locking cap 215 is shown in further detail in FIGS. 57-61. Locking cap 215 generally comprises a central lumen 315 for receiving shaft 285 of locking pin 210, locking profiles 320 for interacting with complementary locking profiles 260

Figure 59:
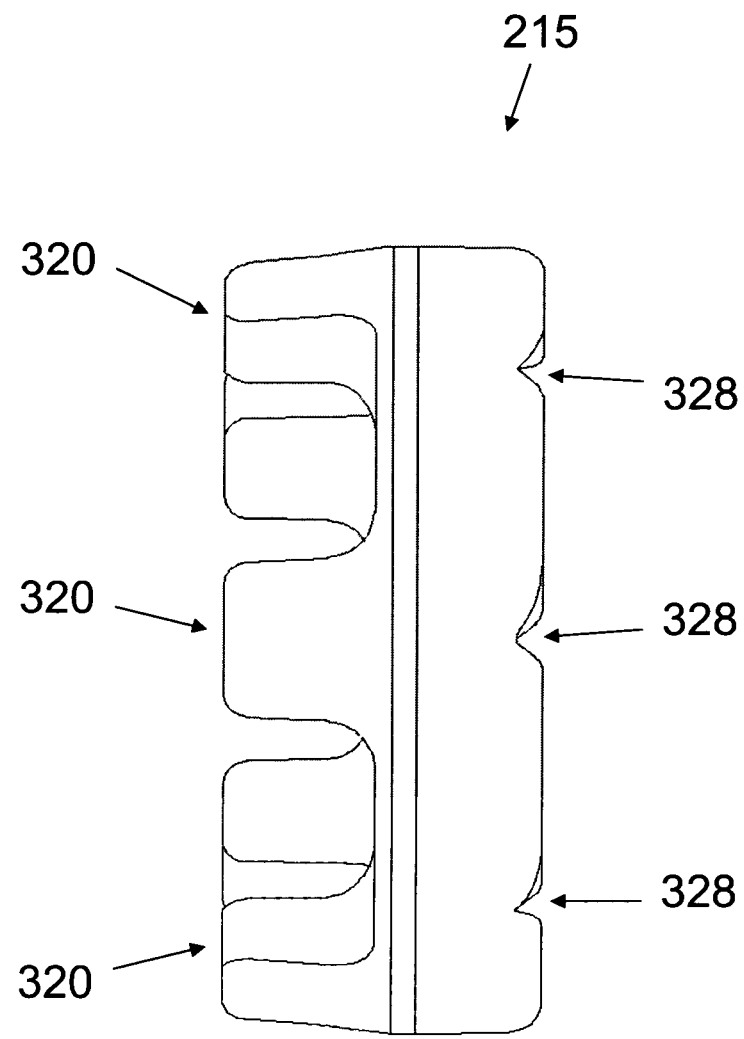
Figure 60:
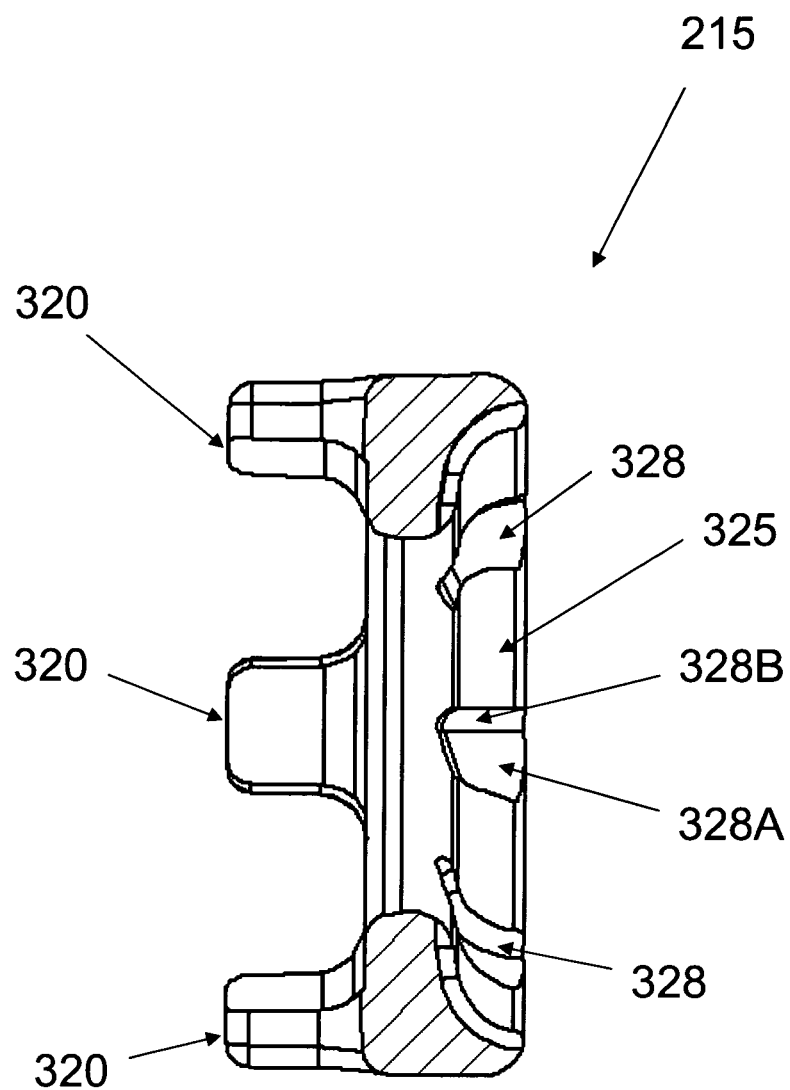
Figure 61:
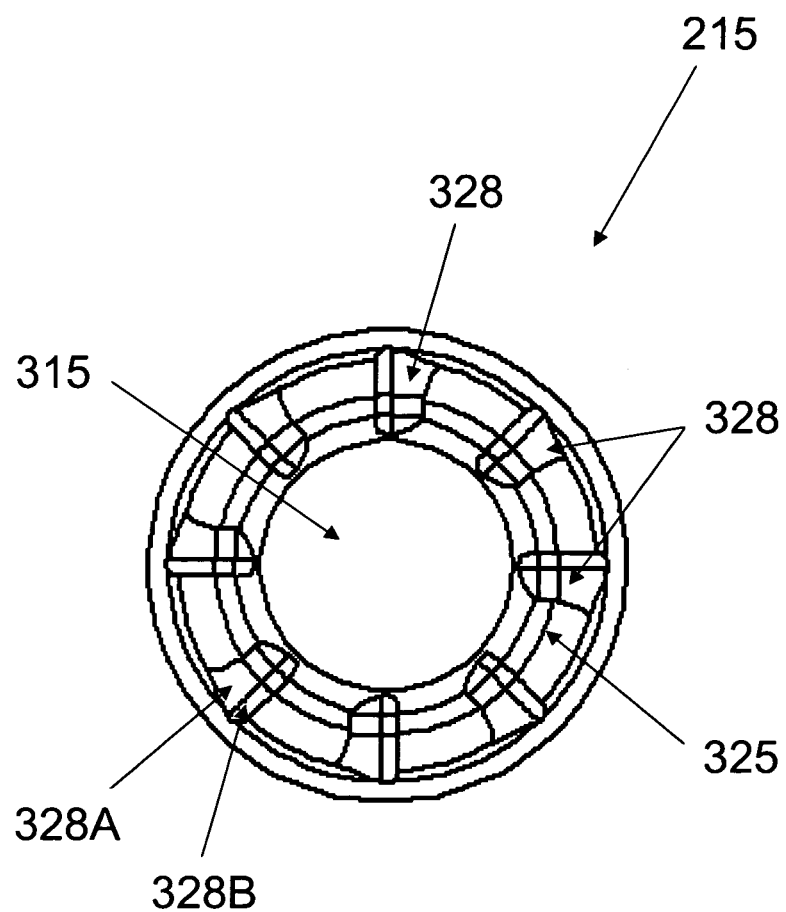

(FIG. 45) on retainer 205, whereby to facilitate gripping graft ligament strands 25 between locking cap 215 and retainer mounting shoulder 240, and a proximal recess 325 (FIG. 60) for seating head 290 of locking pin 210. Preferably one or more radial grooves 328 (FIGS. 60 and 61) are provided in recess 325. Radial grooves 328 comprise a relatively gentle slope 328A (encountered as moving clockwise in FIG. 61) and a relatively steep slope 328B (encountered as moving counterclockwise in FIG. 61). Radial grooves 328 interact with projections 312 formed on the locking pin 210 so as to prevent backout of locking pin 210. In addition, the interaction of projections 312 with radial grooves 328 provide tactile and audible feedback as proper compression is achieved on the graft ligament strands 25. As seen in FIGS. 59-61, the profile of radial grooves 328 allow for positive rotation (i.e., clockwise rotation in FIG. 61) during compressive tightening but prevent backout rotation (i.e., counterclockwise rotation in FIG. 61) of the pin 210.

As noted above, the diameter of central lumen 315 of locking cap 215 is coordinated with locking cap seat 305 (FIG. 55) formed on locking pin 210 so that, prior to locking down locking cap 215 against the retainer's mounting shoulder 240, locking cap 215 can freely rotate on shaft 285 while still preventing locking cap 215 from slipping down shaft 285. As a result, locking cap 215 can be loosely mounted on locking pin 210 and the two members easily manipulated as a unit prior to introducing locking pin 210 into retainer crosshole 235.

Dilator 220 (FIGS. 42 and 43) is preferably used to prepare tibial tunnel 30 and graft ligament strands 25 prior to deploying retainer 205 in the bone tunnel. Dilator 220 essentially (i) compacts the sidewall of the bone tunnel so as to provide a more integral surface for graft ligament engagement, and (ii) compresses the relatively elastic graft ligament strands so as to temporarily reduce their size. Additionally, by dilating the bone tunnel with the graft ligament strands in place, dilator 220 can help mechanically integrate the graft ligament strands with the sidewall of the bone tunnel. Dilator 220 generally comprises a shaft 330 having a distal end 335. Distal end 335 comprises an atraumatic tip 340 and a plurality of longitudally-extending grooves 345 (matching the number of longitudinal grooves 227 in the retainer 205) for receiving graft ligament strands 25, as will hereinafter be discussed. A handle 350 is formed on the proximal end of shaft 330.

Figure 62:
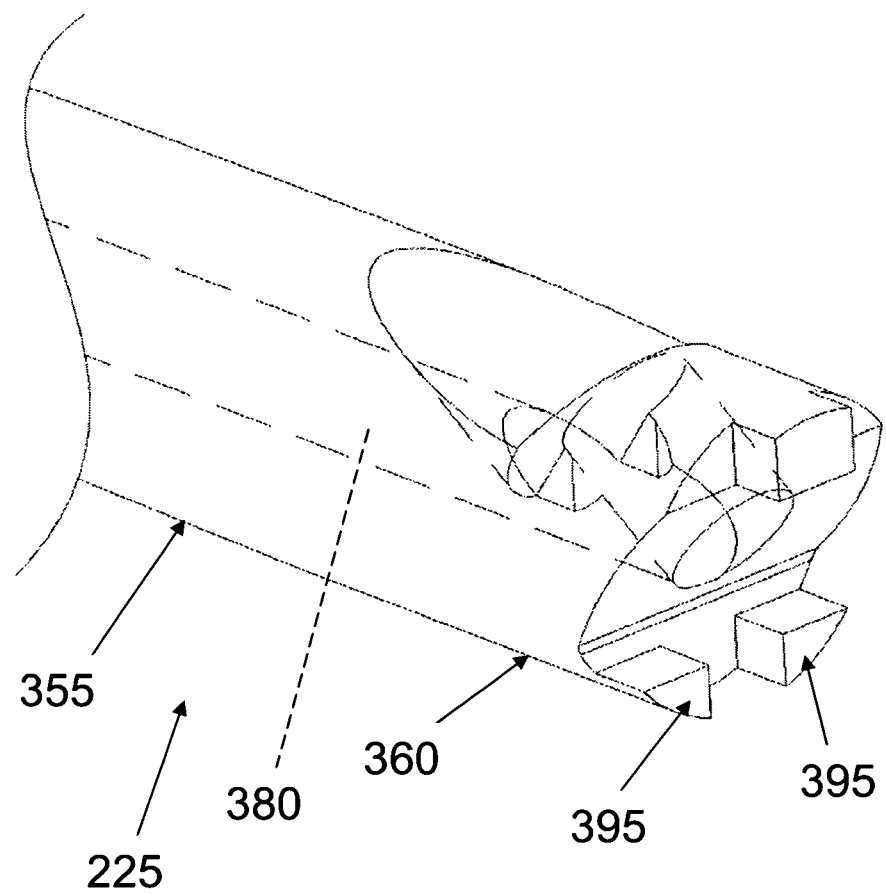
FIGS. 62-65 are schematic views showing further details of the inserter shown in FIG. 44.
Figure 63:
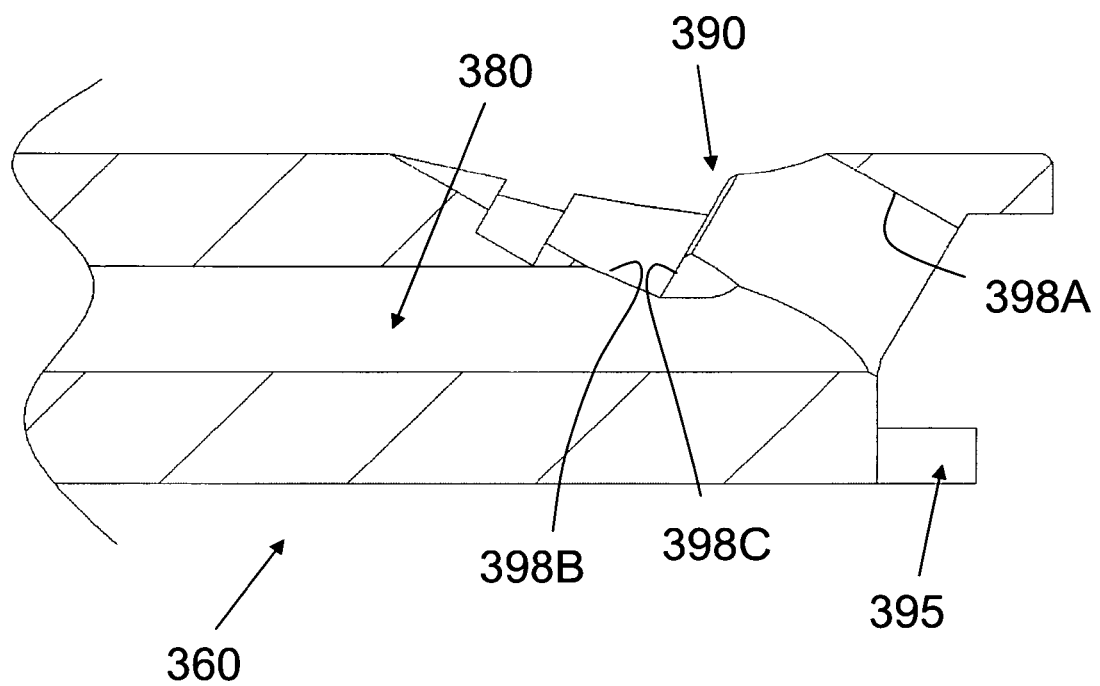
Figure 64:
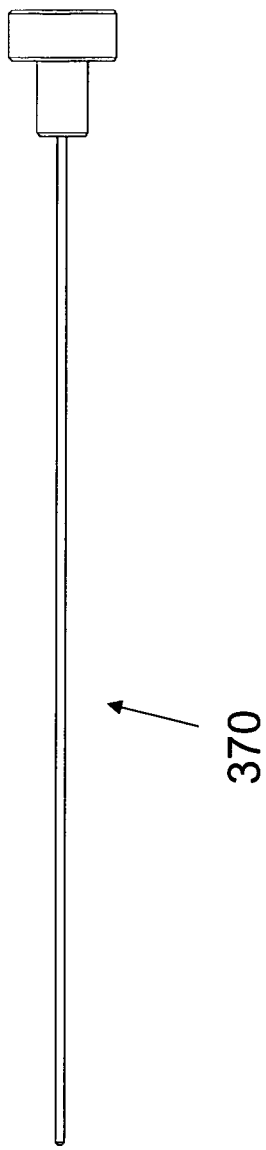
Figure 65:
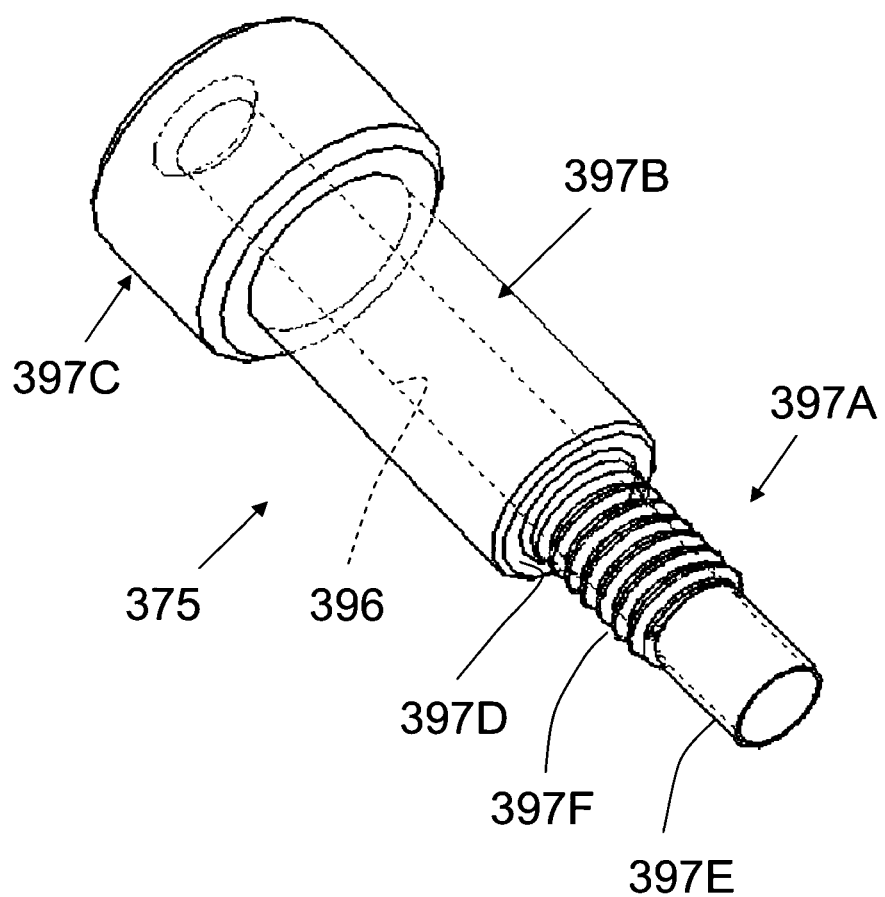

Inserter 225 (FIGS. 44 and 62-65) is preferably used to deploy retainer 205 in tibial tunnel 30. Inserter 225 generally comprises a shaft 355 (FIGS. 44 and 62) having a distal tip 360 (FIGS. 44, 62 and 63) formed at the distal end of shaft 355 and configured to engage the proximal end of retainer 205, a handle 365 (FIG. 44) mounted to the proximal end of shaft 355, and a stylus 370 (FIGS. 44 and 64) for selective insertion through shaft 355 and tip 360 and, when a retainer 205 is mounted to the end of the inserter, through the retainer 205. Stylus 370 provides additional stability to retainer 205 as retainer 205 is deployed in the host bone with inserter 225, as will hereinafter be discussed.

Inserter 225 also preferably comprises a drill bushing 375 (FIG. 65) for selective attachment to tip 360, a lumen 380 (FIG. 62) extending through handle 365, shaft 355 and tip 360 (FIGS. 44, 62 and 63), a drill bushing seat 390 (FIG. 63), and fingers 395 (FIG. 63), each of which is discussed in greater detail below.

Drill bushing 375 (FIG. 65) comprises a central lumen 396 and a stepped outer profile including a leading nose 397A, a following shaft 397B, and a tailing grip 397C. An annular shoulder 397D is formed at the intersection of leading nose 397A and following shaft 397B. Preferably leading nose 397A comprises a smooth section 397E followed by a threaded section 397F. Drill bushing 375 is selectively mounted to tip 360 by means of drill bushing seat 390 (see below) and is used to accurately drill a crosshole in the host bone, as will hereinafter be discussed in further detail.

Lumen 380, which extend through handle 365, shaft 355 and tip 360, accommodates the removable stylus 370.

Drill bushing seat 390 (FIG. 63) comprises a threaded bore 398A and a partial counterbore 398B, with an annular shoulder 398C being formed at the intersection of bore 398A and counterbore 398B. Drill bushing seat 390 selectively accommodates drill bushing 375, with the bushing's threaded section 397F received by the seat's bore 398A and the bushing's following shaft 397B received in the seat's partial counterbore 398B, whereby drill bushing 375 may be mounted to tip 360, with the smooth section 397E of drill bushing 375 being disposed in and lining the crosshole 235 of the retainer 205 mounted to inserter 225, as will hereinafter be discussed in further detail.

Fingers 395 (FIG. 63) mate with counterpart recesses 275 (FIG. 48) of retainer 205, whereby to selectively hold retainer 205 on the distal end of inserter 225.

If desired, shaft 355 and tip 360 can be formed as a single member or as a pair of members united during manufacture.

Figure 66:
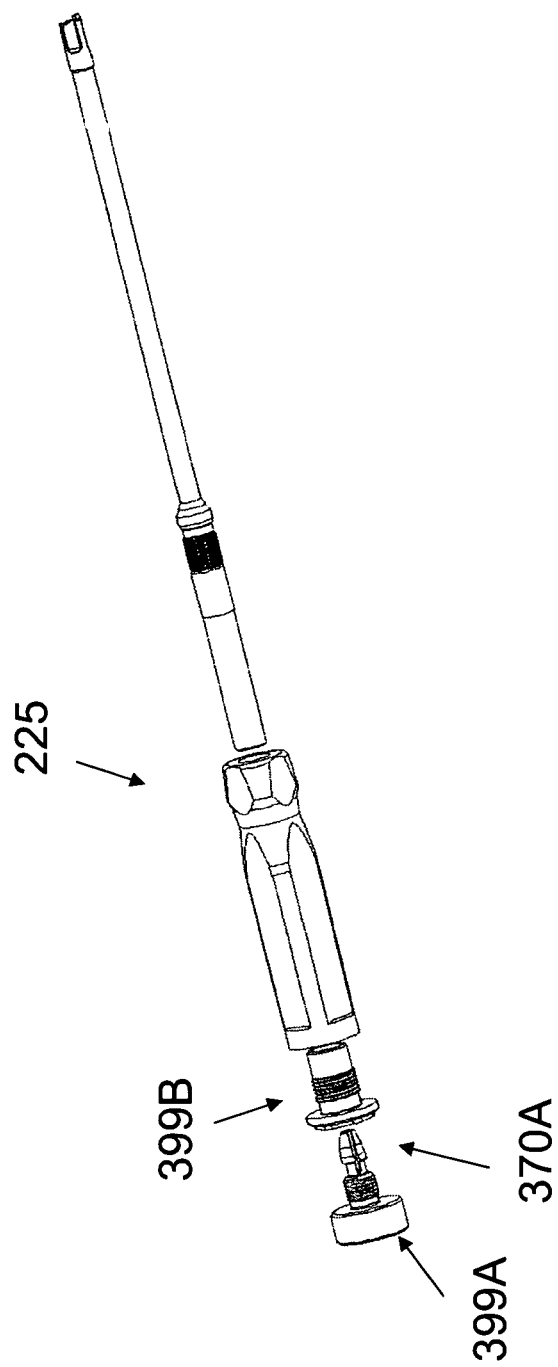
FIGS. 66 and 67 are schematic views showing an alternative form of the inserter.
Figure 67:
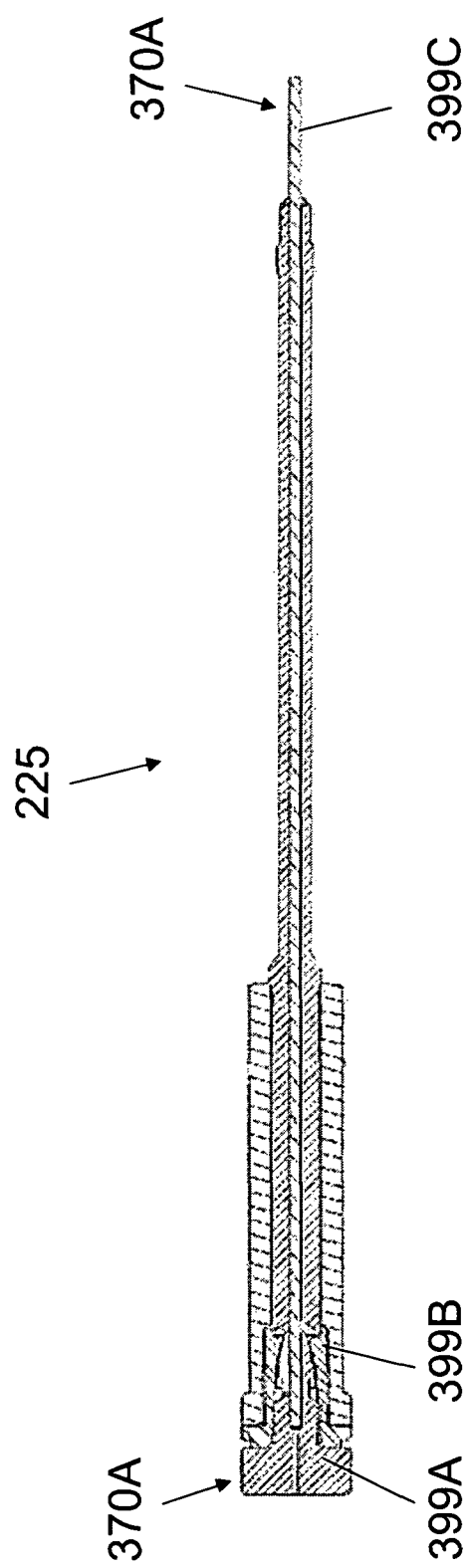

If desired, a stylus 370A (FIGS. 66 and 67) may be used in place of stylus 370. Stylus 370A comprises a collet 399A received in a body 399B for adjustably gripping of the wire 399C.

Ligament fixation system 200 is preferably used as follows.

First, tibial bone tunnel 30 and femoral bone tunnel 35 are formed in ways well known in the art; graft ligament strands 25 are advanced through tibial tunnel 30, across the knee joint, and into femoral bone tunnel 35 in ways well known in the art; and graft ligament strands 25 are made fast in femoral bone tunnel 35, with the graft ligament strands 25 extending back across the knee joint, through tibial bone tunnel 30 and out the front of tibia 10, all in ways well known in the art.

Figure 68:
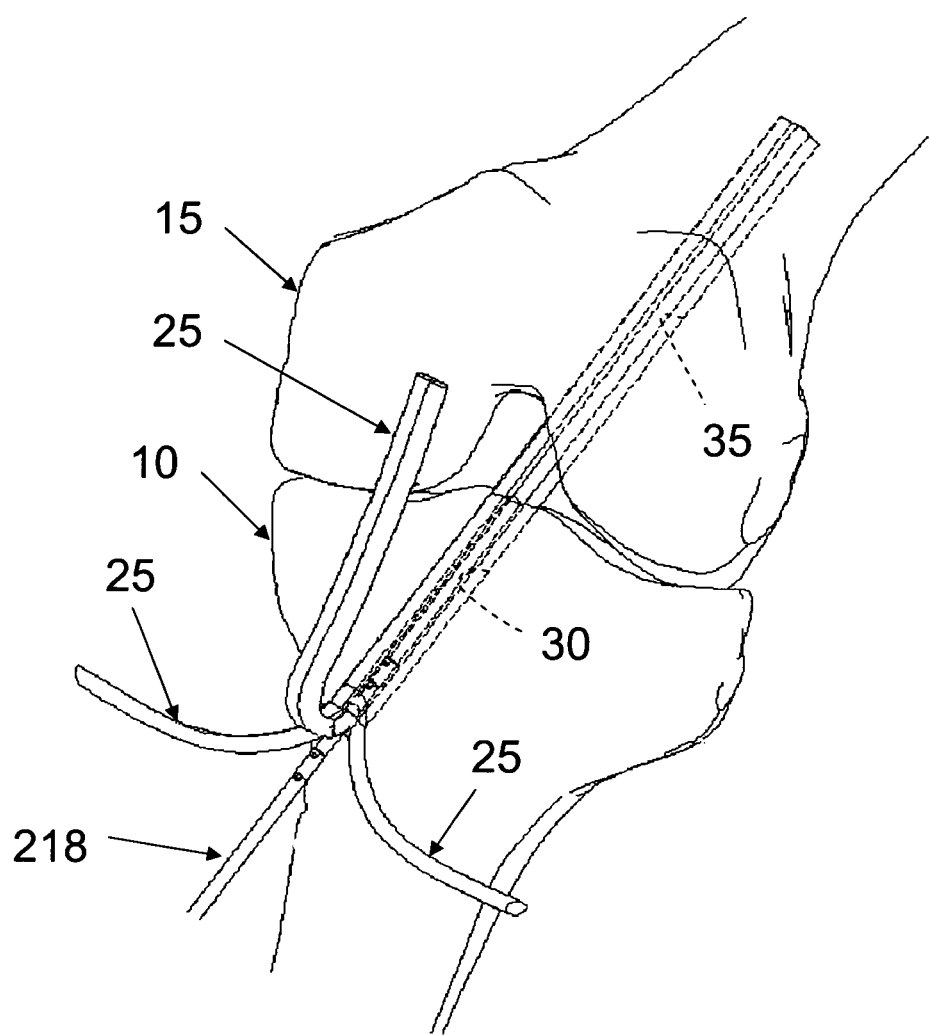
FIGS. 68-81 are a series of views showing how the ligament fixation system of FIG. 41 may be used to fix a graft ligament in a tibial tunnel.
Figure 69:
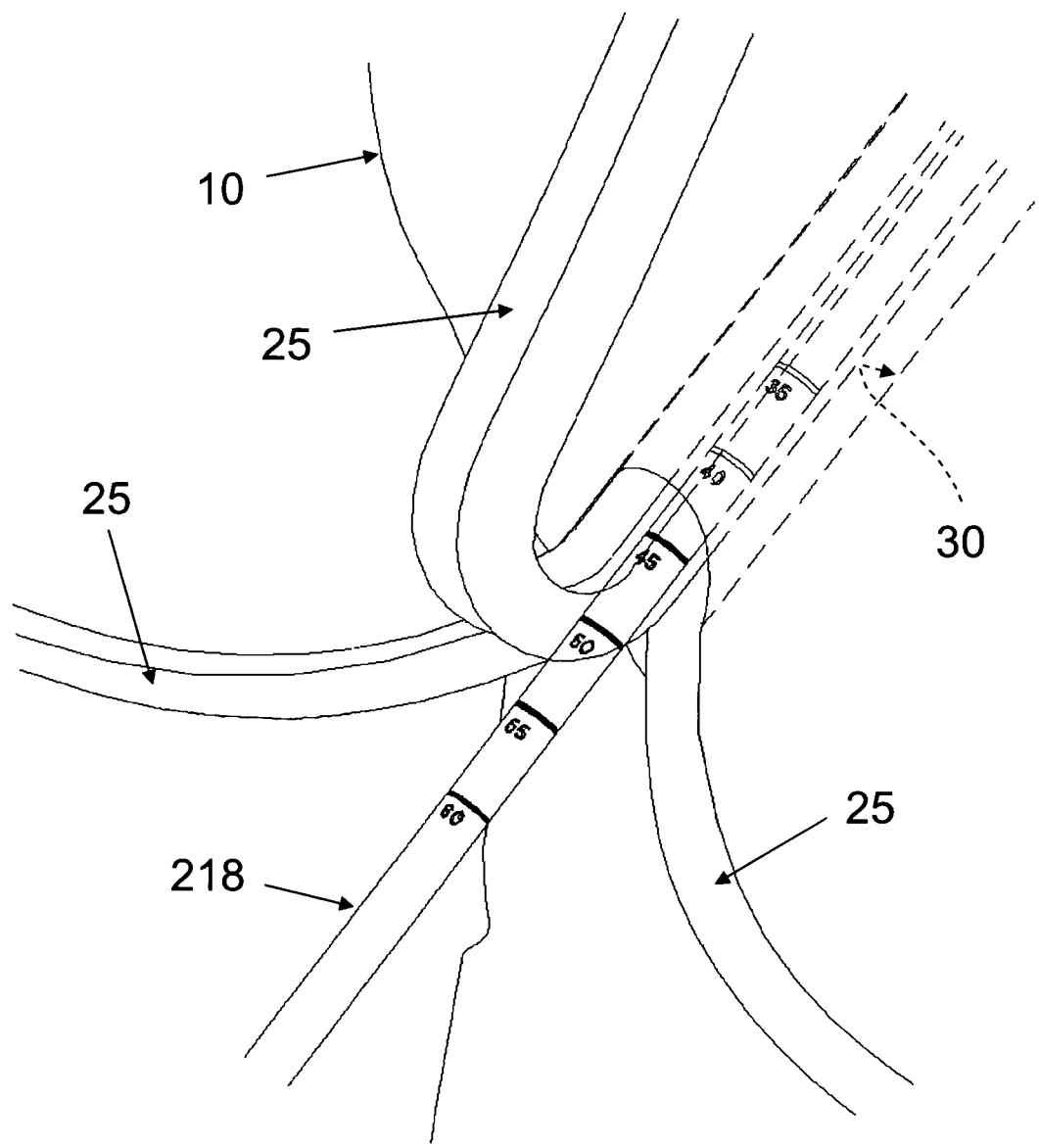

Next, and looking now at FIGS. 68 and 69, a sizing wire 218 (or other tool) is advanced into tibial bone tunnel 30 to determine the depth of tibial bone tunnel 30. This is done using the graduation markings formed on sizing wire 218. The depth of the tibial bone tunnel 30 determines the length of the retainer 205 which is used in the ligament reconstruction.

Figure 70:
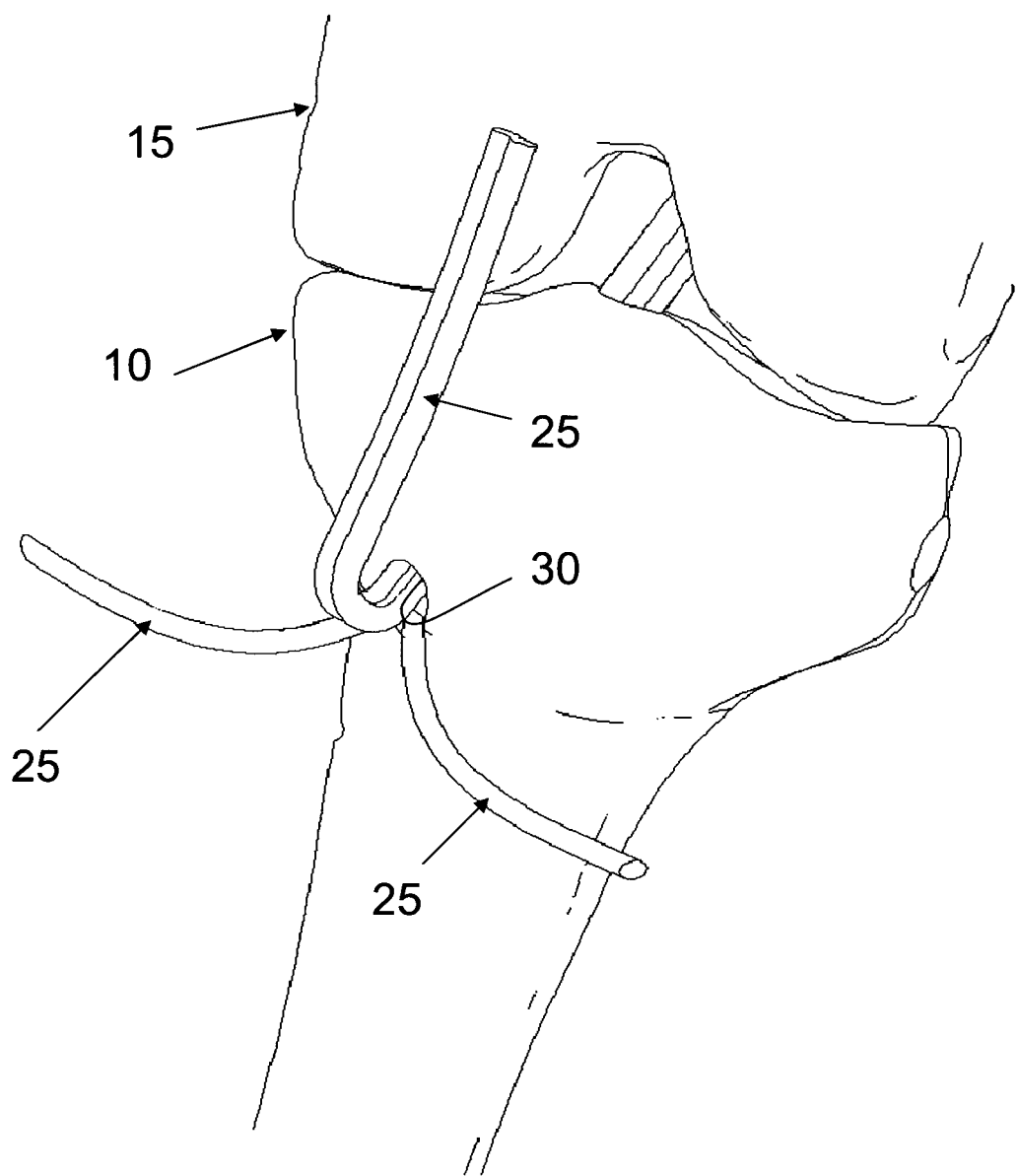
Figure 71:
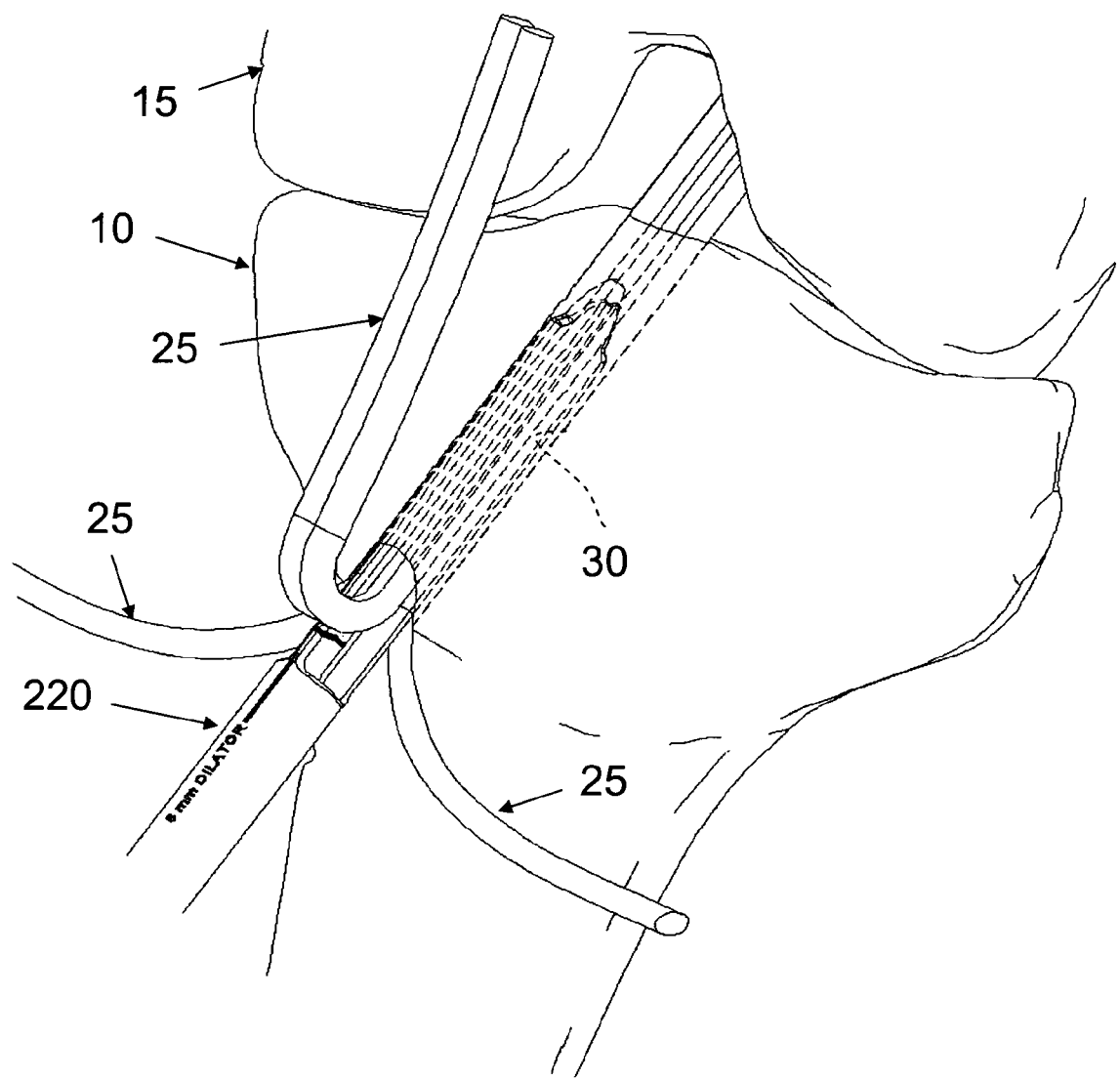
Figure 72:
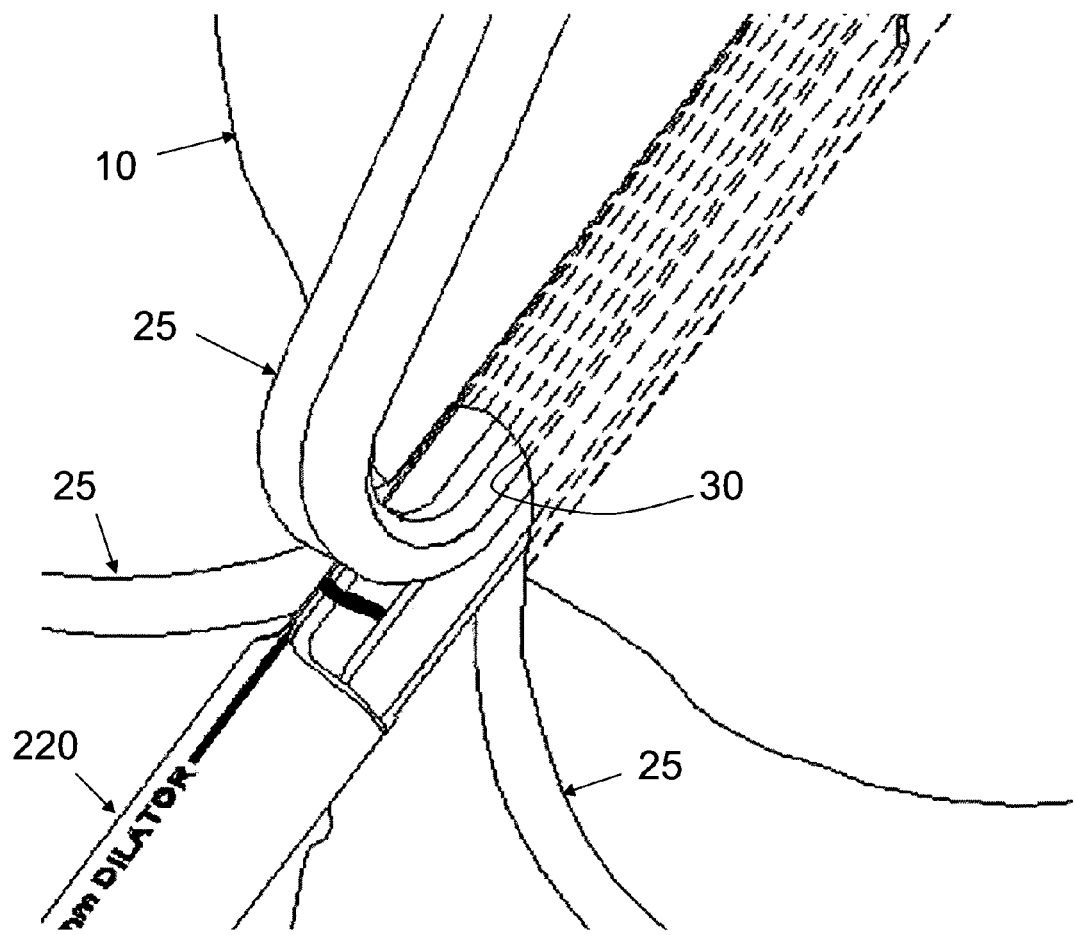
Figure 73:
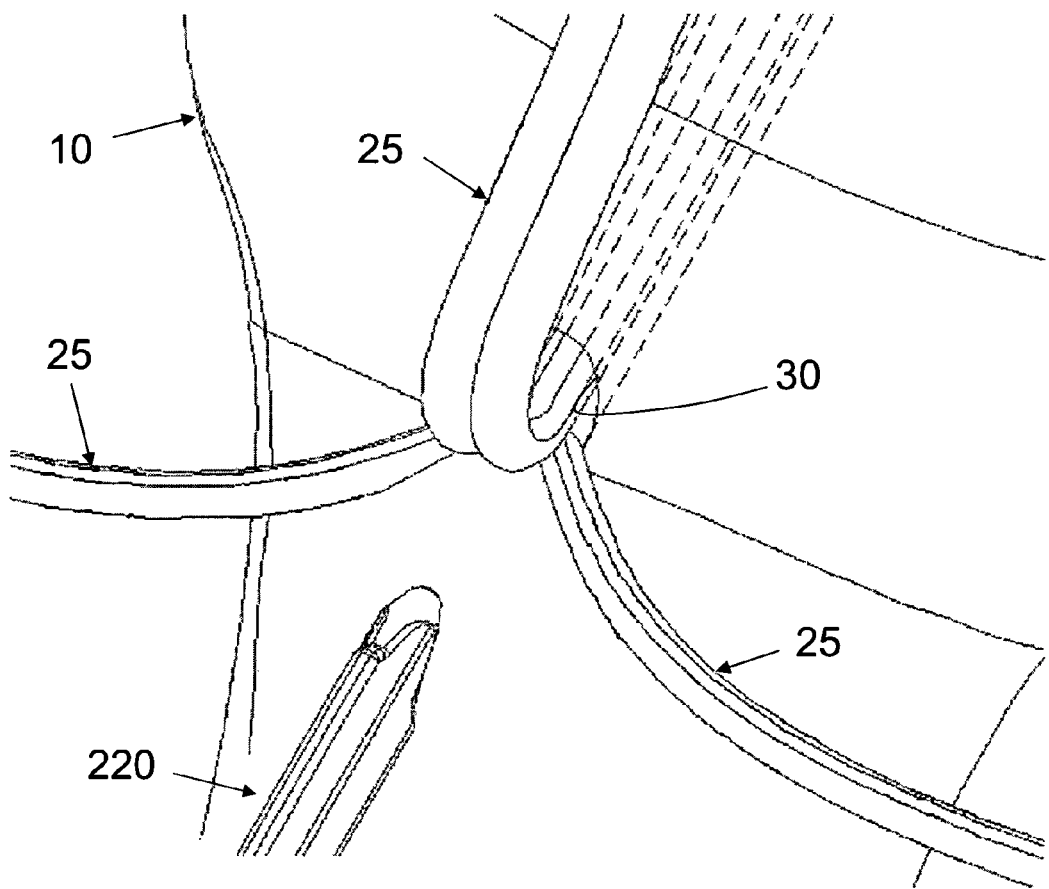

Then sizing wire 218 is removed from tibial bone tunnel 30 (FIG. 70) and, while the free ends of the graft ligament strands 25 are held under tension, the dilator 220 is advanced into tibial bone tunnel 30 (FIG. 71), with the graft ligament strands 25 being received in the dilator's longtiduinally-extending grooves 345. As dilator 220 is advanced into tibial bone tunnel 30, the dilator forces graft ligament strands 25 against the sidewall of tibial bone tunnel 30, compressing graft ligament strands 25 so as to temporarily remove fluid from the graft ligament strands 25, compressing the host bone so as to form a more integral bone wall, and mechanically integrating and contouring the graft ligament strands into the host bone. Dilator 220 is advanced to an appropriate depth, using gradation markings formed on the surface of dilator 220 (FIG. 72). Then dilator 220 is removed from tibial bone tunnel 30 (FIG. 73).

Figure 74:
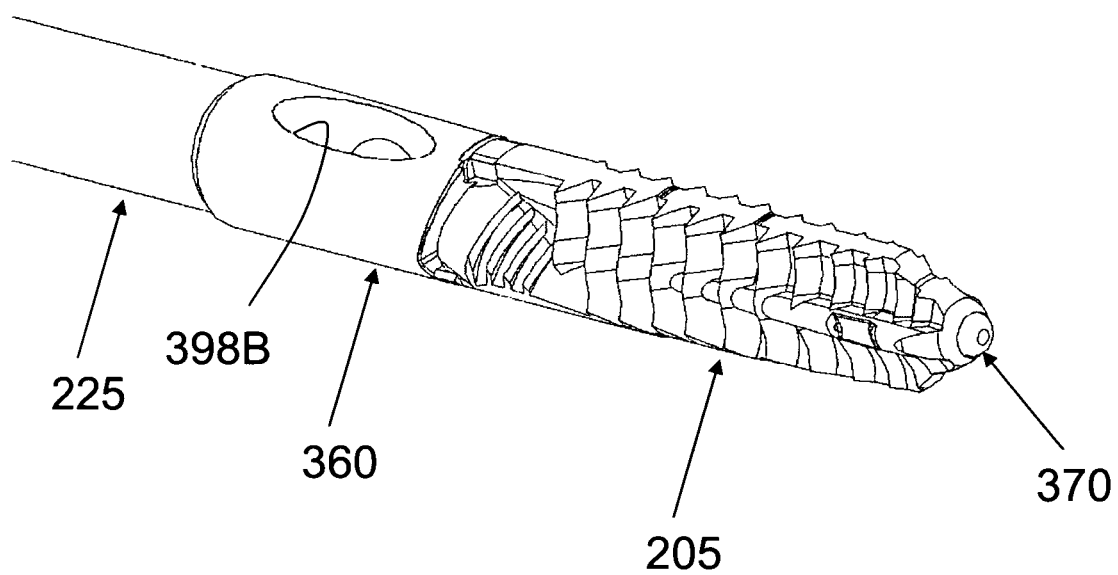
Figure 75:
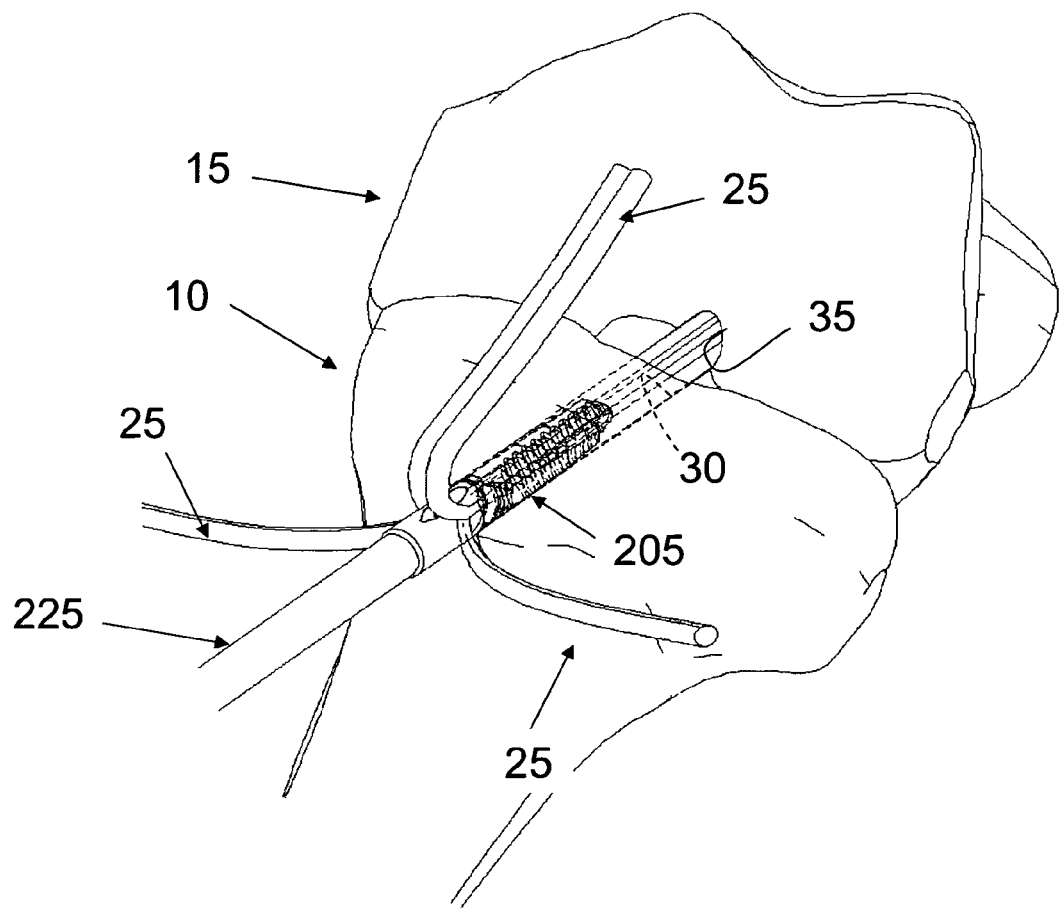
Figure 76:
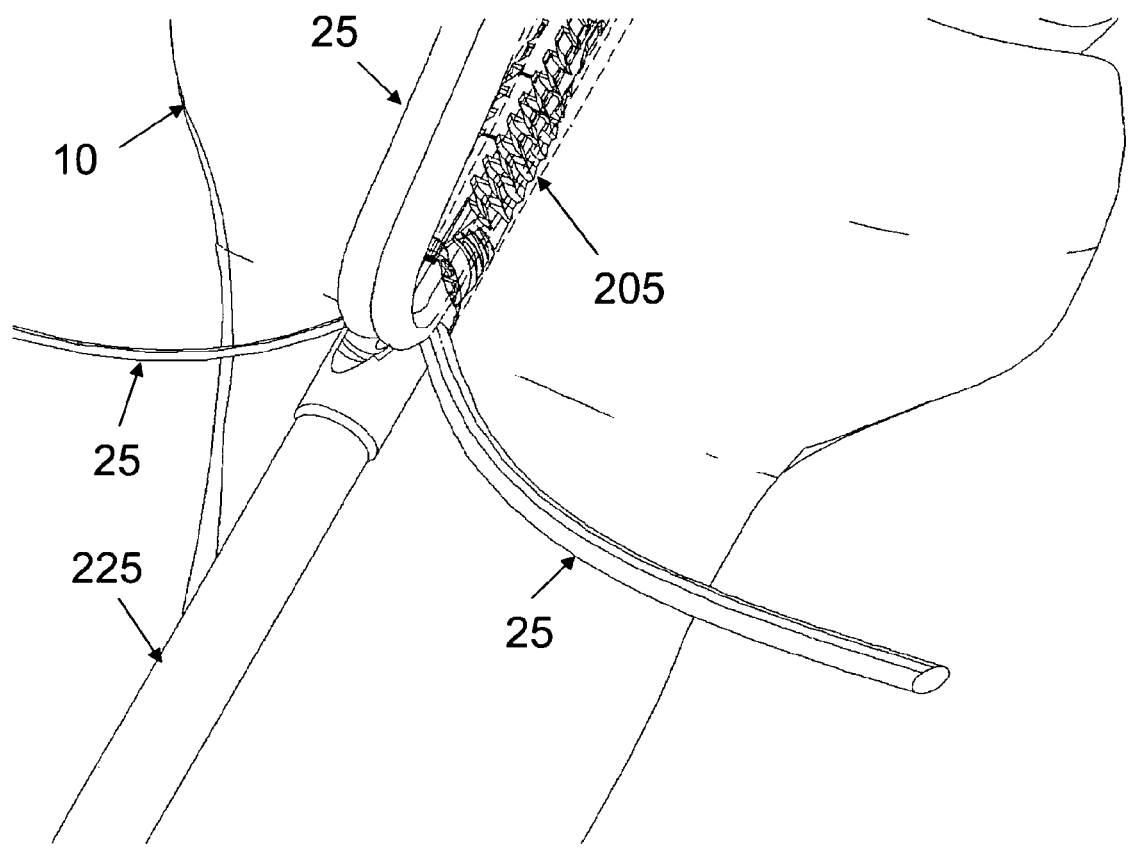
Figure 77:
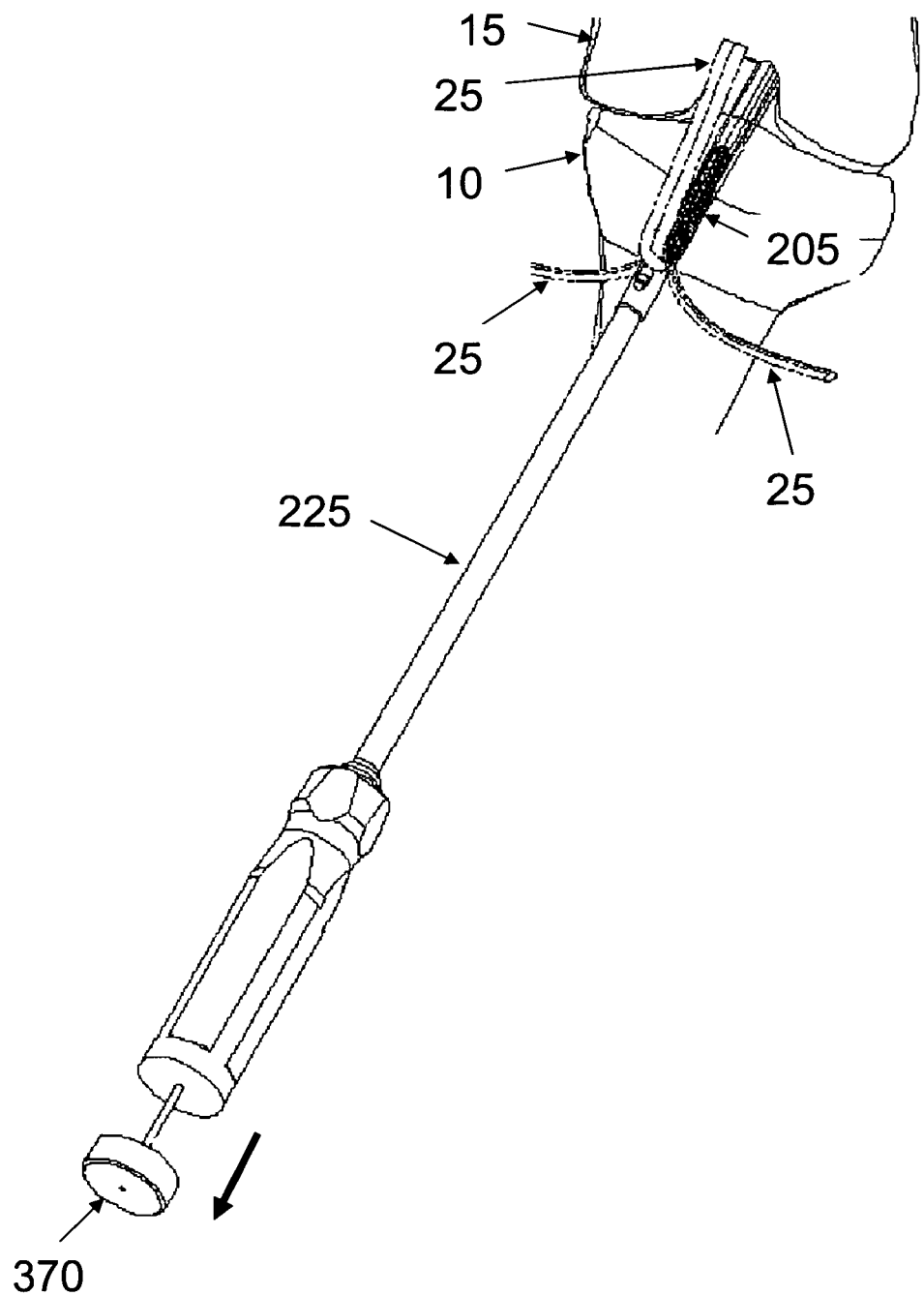

Next, retainer 205 is loaded onto inserter 225, with inserter fingers 395 engaging recesses 275 in retainer 205, and with stylus 370 passing through inserter shaft 355, inserter tip 360 and retainer 205 (FIG. 74). Then inserter 225 is used to advance retainer 205 to its proper position within bone tunnel 30 (FIGS. 75 and 76). As retainer 205 is inserted into bone tunnel 30, graft ligament strands 25 (which are held under tension by pulling on their free ends) are received in the retainer's longitudinally-extending grooves 227 so that the retainer's lofted profile 255 gently but firmly compresses the graft ligament strands against the sidewall of the bone tunnel. Retainer 205 is advanced until it is properly wedged into position. Once the proper positioning of retainer 205 has been achieved, stylus 370 is removed (FIG. 77). At this point, retainer 205 compressively holds the graft ligament strands 25 against the bone, by virtue of its being wedged into position in the bone tunnel.

Figure 78:
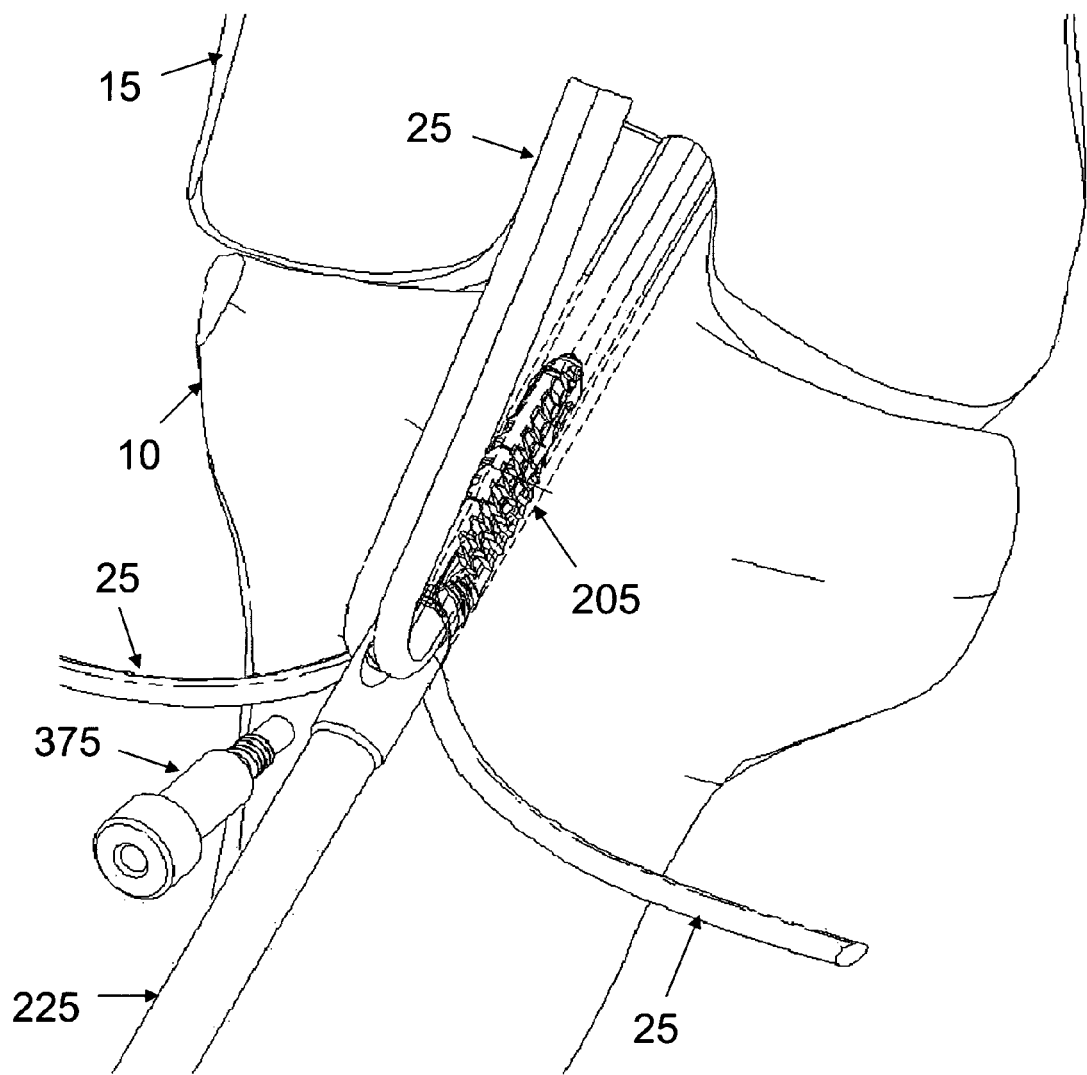
Figure 78A:
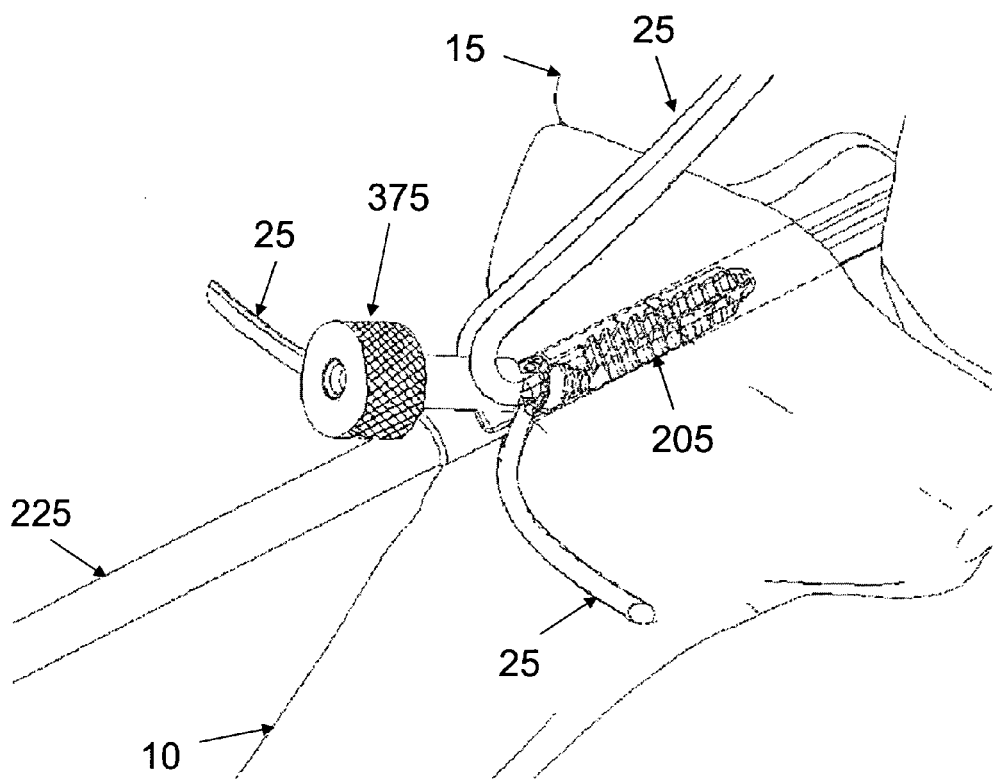
Figure 79:
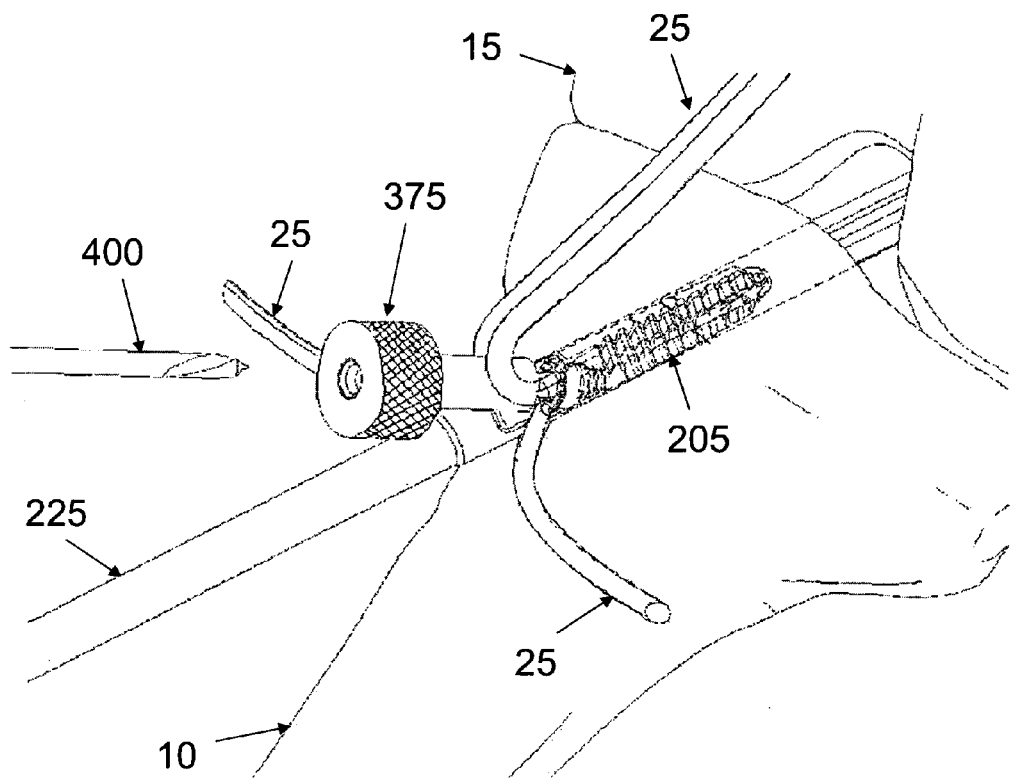
Figure 80:
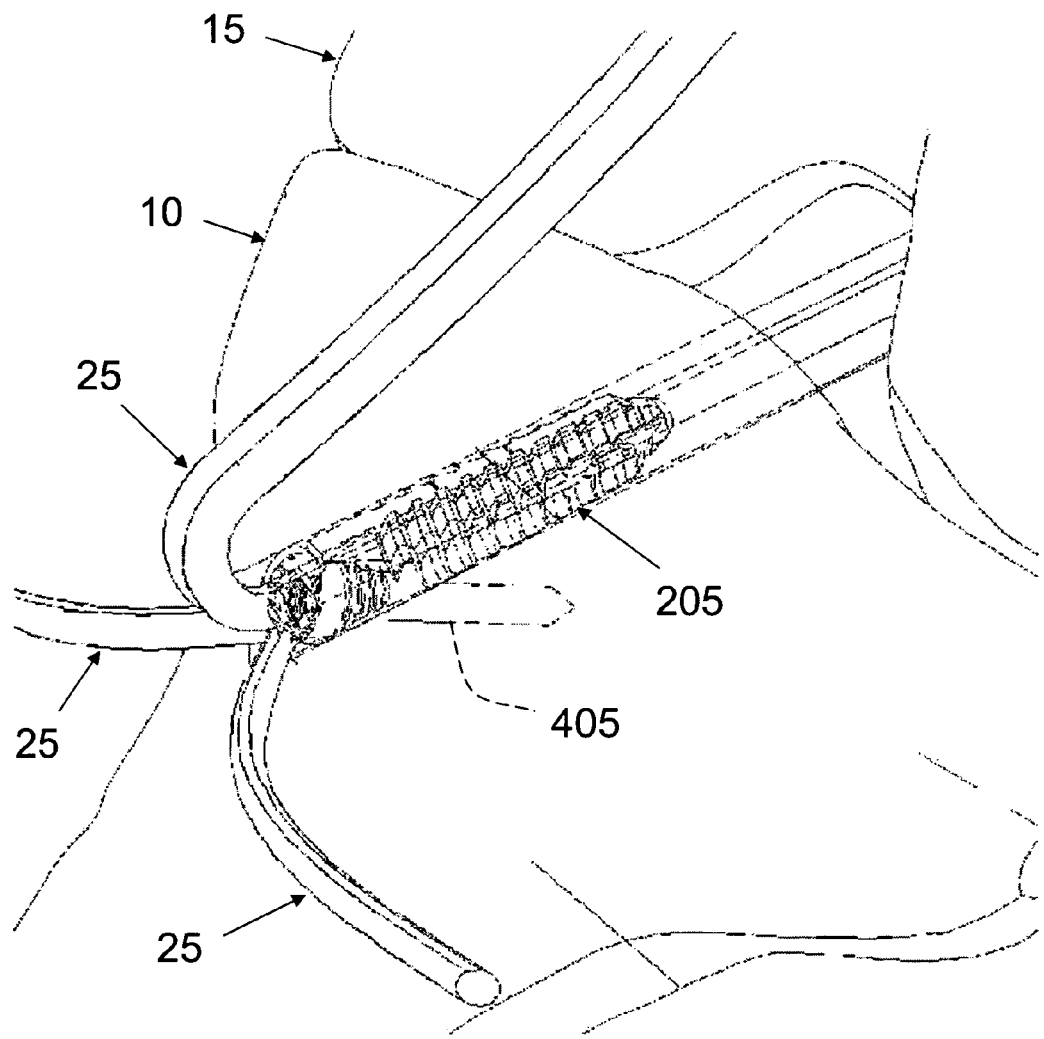

Next, drill bushing 375 is positioned on drill bushing seat 390 (FIGS. 78 and 78A, and a drill 400 is used to form a crosshole 405 into the host bone (FIGS. 79 and 80). Once the crosshole 405 has been formed, drill bushing 375 is removed and inserter 225 is removed (FIG. 80).

Figure 81:
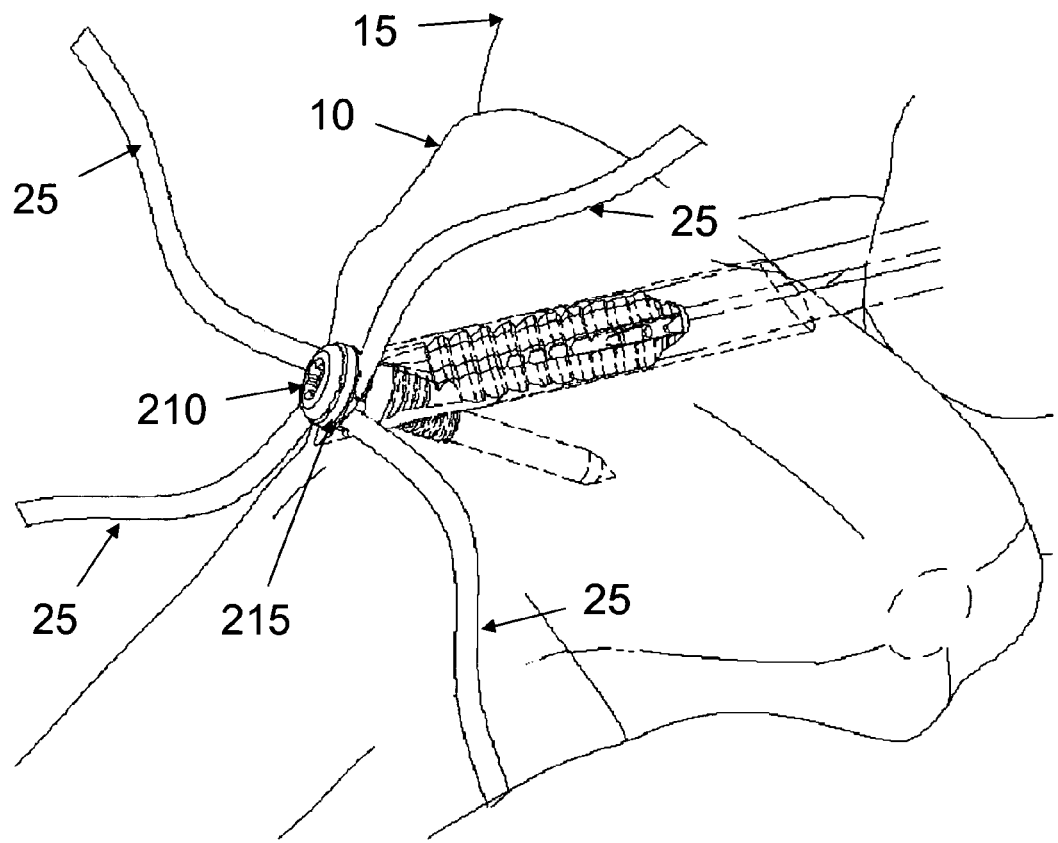

Next, locking pin 210 (with locking cap 215 carried in locking cap seat 305), is installed in retainer crosshole 235 and the crosshole 405 drilled into the host bone, with locking cap 215 capturing the graft ligament strands 25 against retainer's mounting shoulder 240, so as to simultaneously bind retainer 205 to the host bone and graft ligament strands 25 to retainer 205 (FIG. 81).

Thus, with ligament fixation system 200, graft ligament strands 25 are held to tibia 10 by virtue of the compression provided by retainer 205; in addition, the graft ligament strands 25 are secured to retainer 205 by locking cap 215, with the complete assembly being pinned to the host bone via locking pin 210.

It should also be appreciated that, inasmuch as graft ligament strands 25 tend to be slightly elastic, and inasmuch as graft ligament strands 25 are secured under tension, upon retainer deployment, graft ligament strands 25 will tend to urge retainer 205 further into the bone tunnel, thereby enhancing the wedging lock to the bone.

Thereafter, over time, graft ligament strands 25 and the host bone integrate so as to provide a biologic union.

If desired, locking pin 210 can have its threads 295 replaced by a ribbed or barbed construction, and retainer 205 can have its threads 270 replaced by a mating geometry so as to form a one-way ratchet mechanism.

Furthermore, if desired, locking pin 210 and locking cap 215 can be formed with a singular construction, i.e., with an integral construction.

Figure 81A:
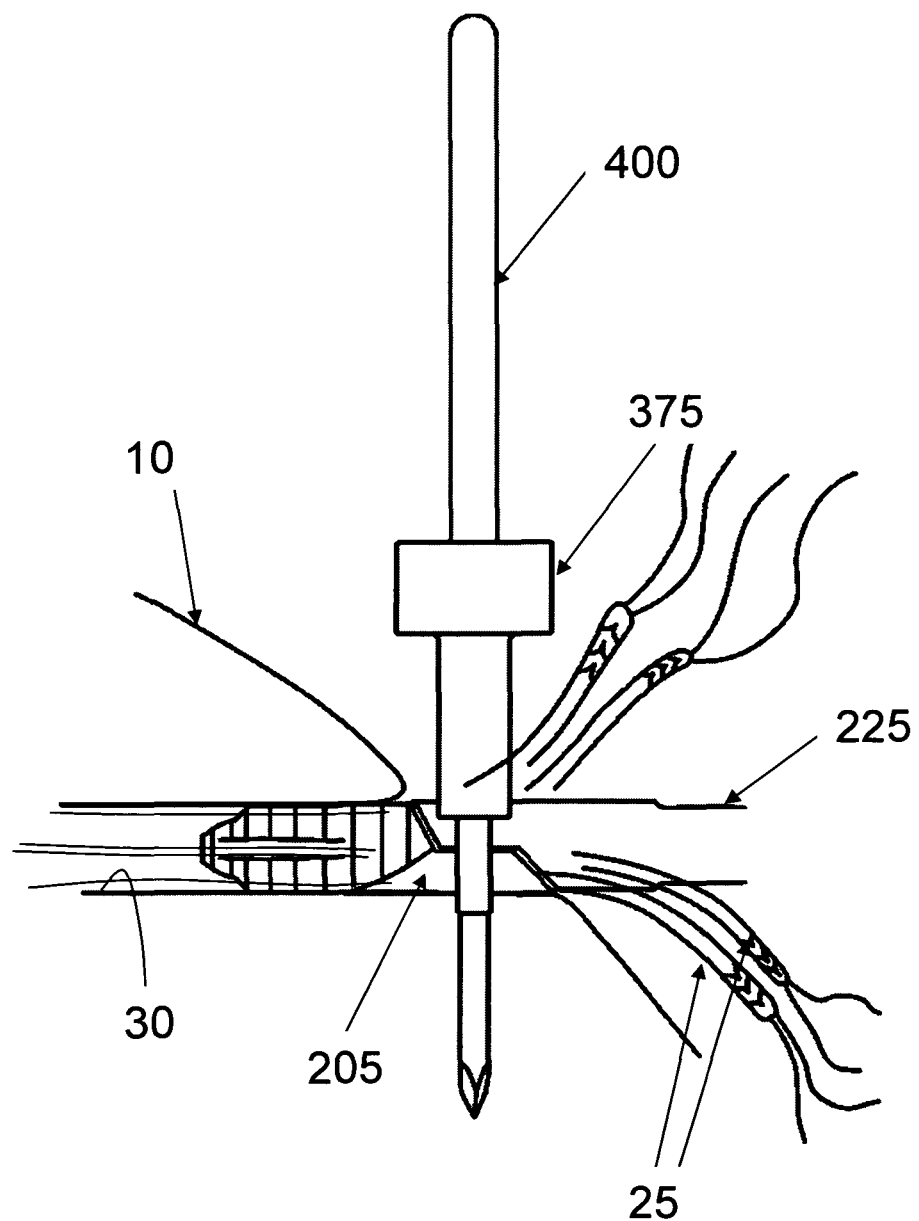
FIGS. 81A and 81B are schematic views showing an alternative form of the system formed in accordance with the present invention.
Figure 81B:
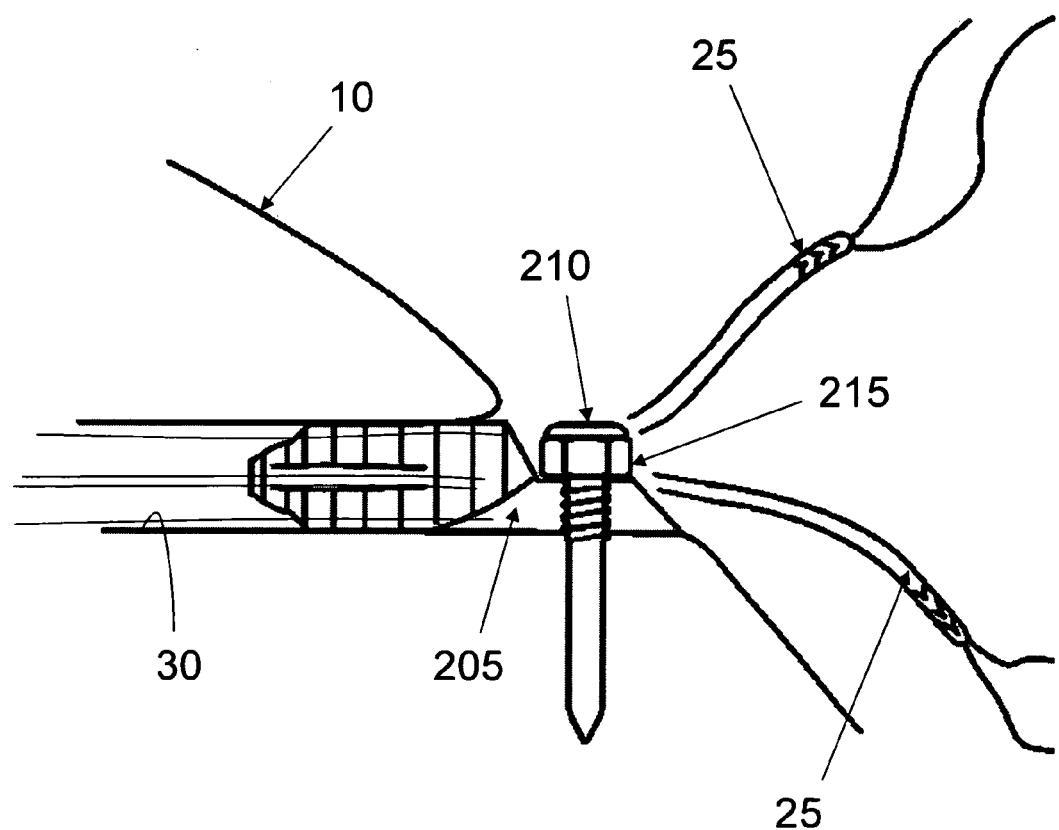

FIGS. 81A and 81B show an alternative form of the system formed in accordance with the present invention.

In one preferred form of the invention, the system is modified so that the crosshole 405 is formed in the tibia after inserter 225 has been withdrawn.

Figure 82:
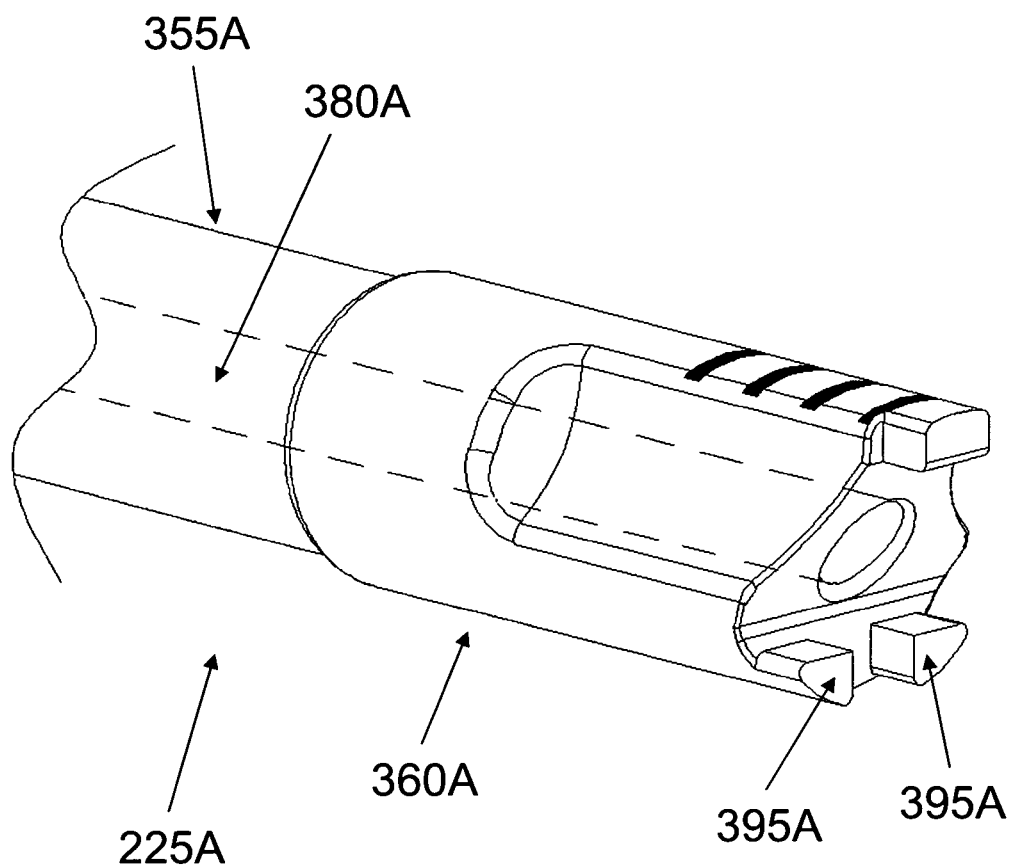
FIGS. 82-85 are schematic views showing an alternative form of a inserter.
Figure 83:
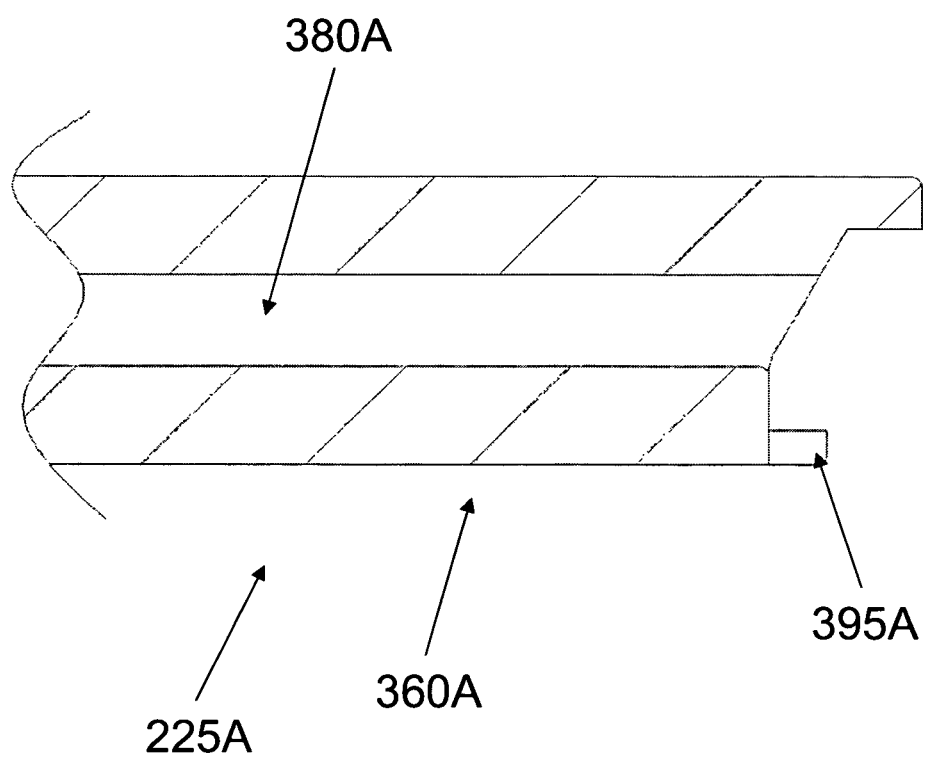
Figure 84A:
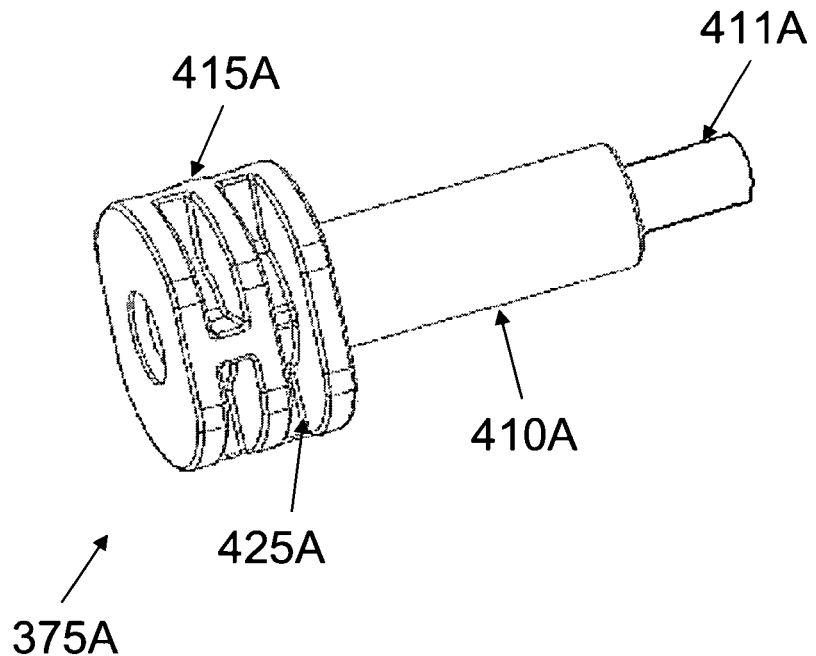
Figure 84B:
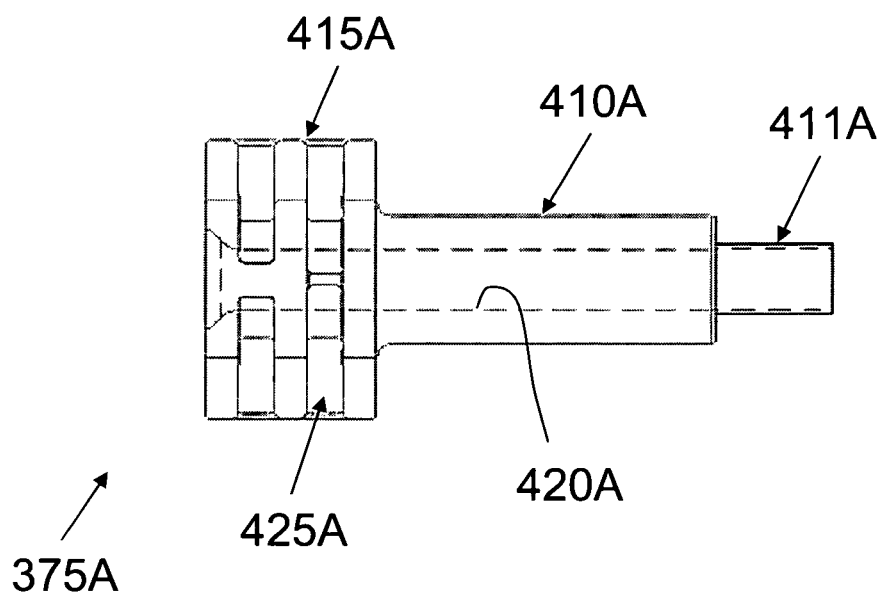
Figure 85:
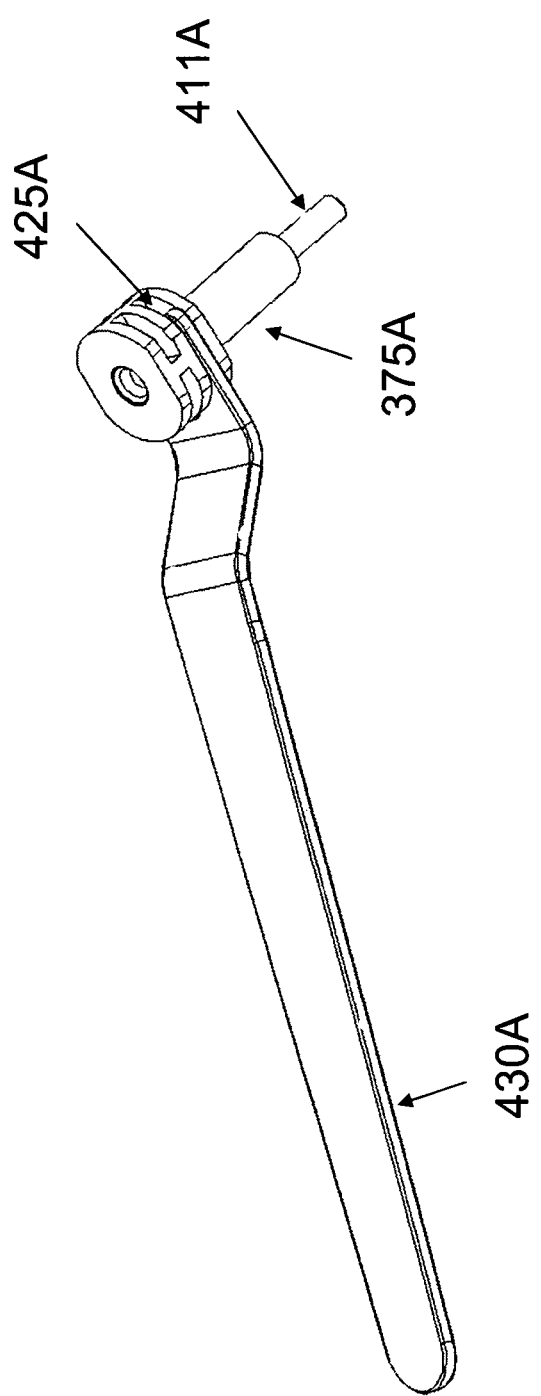

More particularly, with this form of the invention, and looking now at FIGS. 82 and 83, a modified inserter 225A is provided. Inserter 225A includes a modified distal tip 360A which is generally similar to the tip 360 previously disclosed, except that it omits the drill bushing seat 390. In addition, and looking now at FIGS. 84A, 84B and 85, a modified drill bushing 375A is provided. Drill bushing 375A comprises a smooth shaft 410A terminating on its distal end in a smaller smooth shaft 411A and terminating on its proximal end in a connector 415A, and including a central bore 420A. Connector 415A includes one or more openings 425A for engagement by a handle 430A. In this form of the invention, drill bushing 375A is mounted directly in retainer 205 when forming the bone crosshole 405, i.e., with smaller smooth shaft 411A seated in retainer crosshole 235.

More particularly, in this form of the invention, the ligament reconstruction is effected as follows.

First, tibial bone tunnel 30 and femoral bone tunnel 35 are formed in ways well known in the art; graft ligament strands 25 are advanced through tibial tunnel 30, across the knee joint, and into femoral bone tunnel 35 in ways well known in the art; and graft ligament strands 25 are made fast in femoral bone tunnel 35, with the graft ligament strands 25 extending back across the knee joint, through tibial bone tunnel 30 and out the front of tibia 10, all in ways well known in the art.

Next, the sizing wire 218 (or other tool) is advanced into tibial bone tunnel 30 to determine the depth of tibial bone tunnel 30. This is done using the graduation markings formed on sizing wire 218. The depth of the tibial bone tunnel 30 determines the length of the retainer 205 which is used in the ligament reconstruction.

Then sizing wire 218 is removed from tibial bone tunnel 30 and, while the free ends of the graft ligament strands 25 are held under tension, the dilator 220 is advanced into tibial bone tunnel 30, with the graft ligament strands 25 being received in the dilator's longtiduinally-extending grooves 345. As dilator 220 is advanced into tibial bone tunnel 30, the dilator forces graft ligament strands 25 against the sidewall of tibial bone tunnel 30, compressing graft ligament strands 25 so as to temporarily removed fluid from the graft ligament strands 25, compressing the host bone so as to form a more integral bone wall, and mechanically integrating and contouring the graft ligament strands into the host bone. Dilator 220 is advanced to an appropriate depth, using gradation markings formed on the surface of dilator 220. Then dilator 220 is removed from tibial bone tunnel 30.

Figure 86:
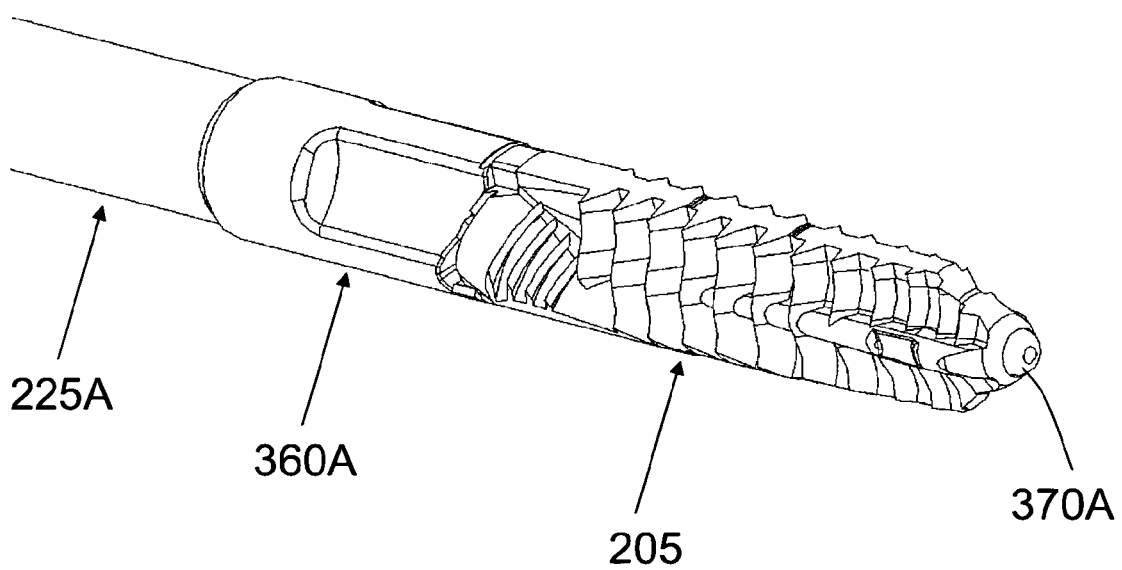
FIGS. 86-92 are a series of views showing how the ligament fixation system may be used to fix a graft ligament in a tibial tunnel.
Figure 87:
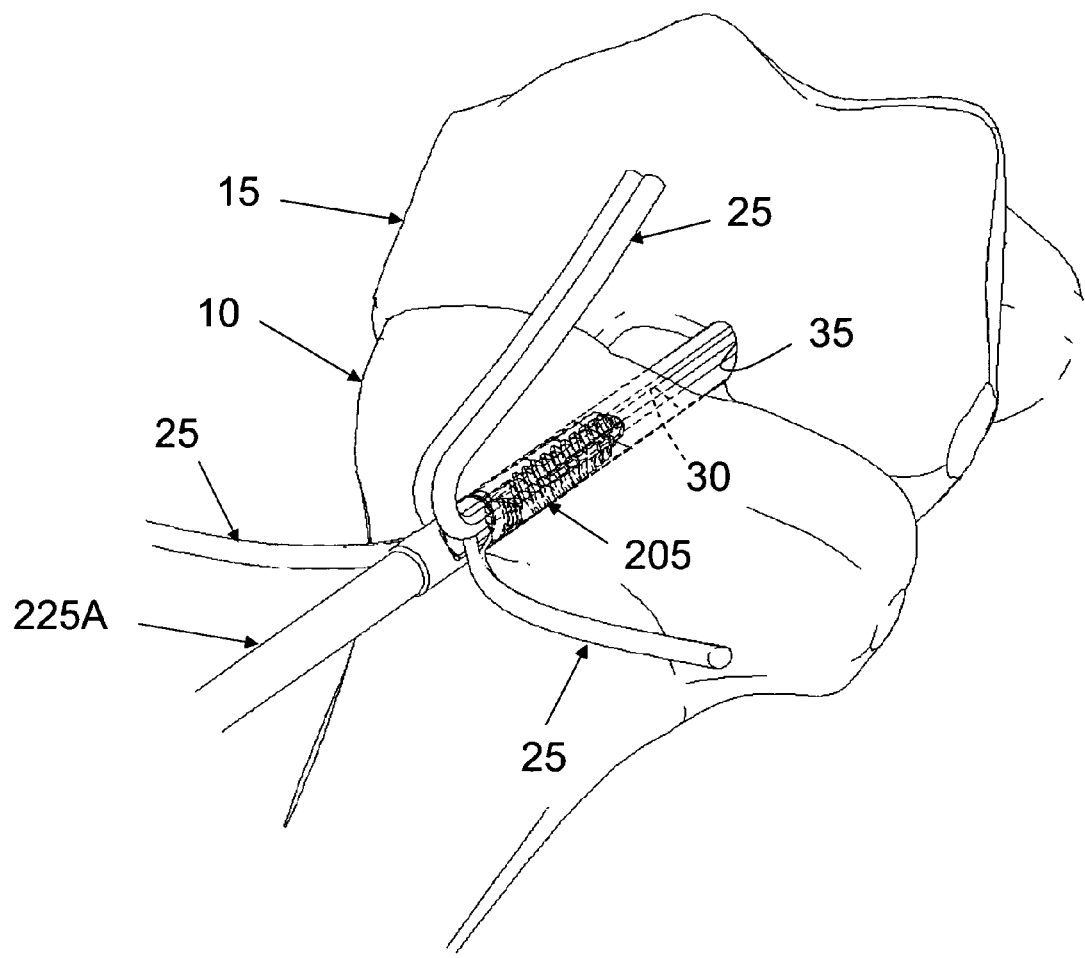
Figure 88:
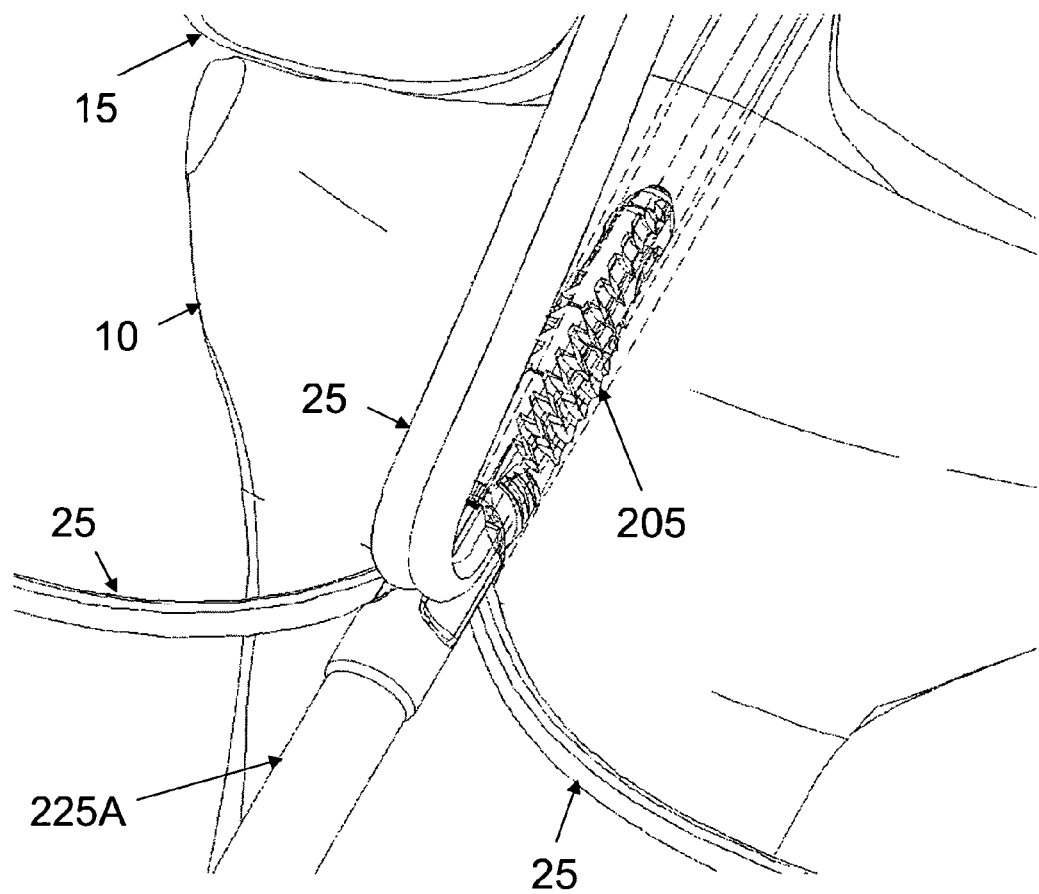
Figure 89:
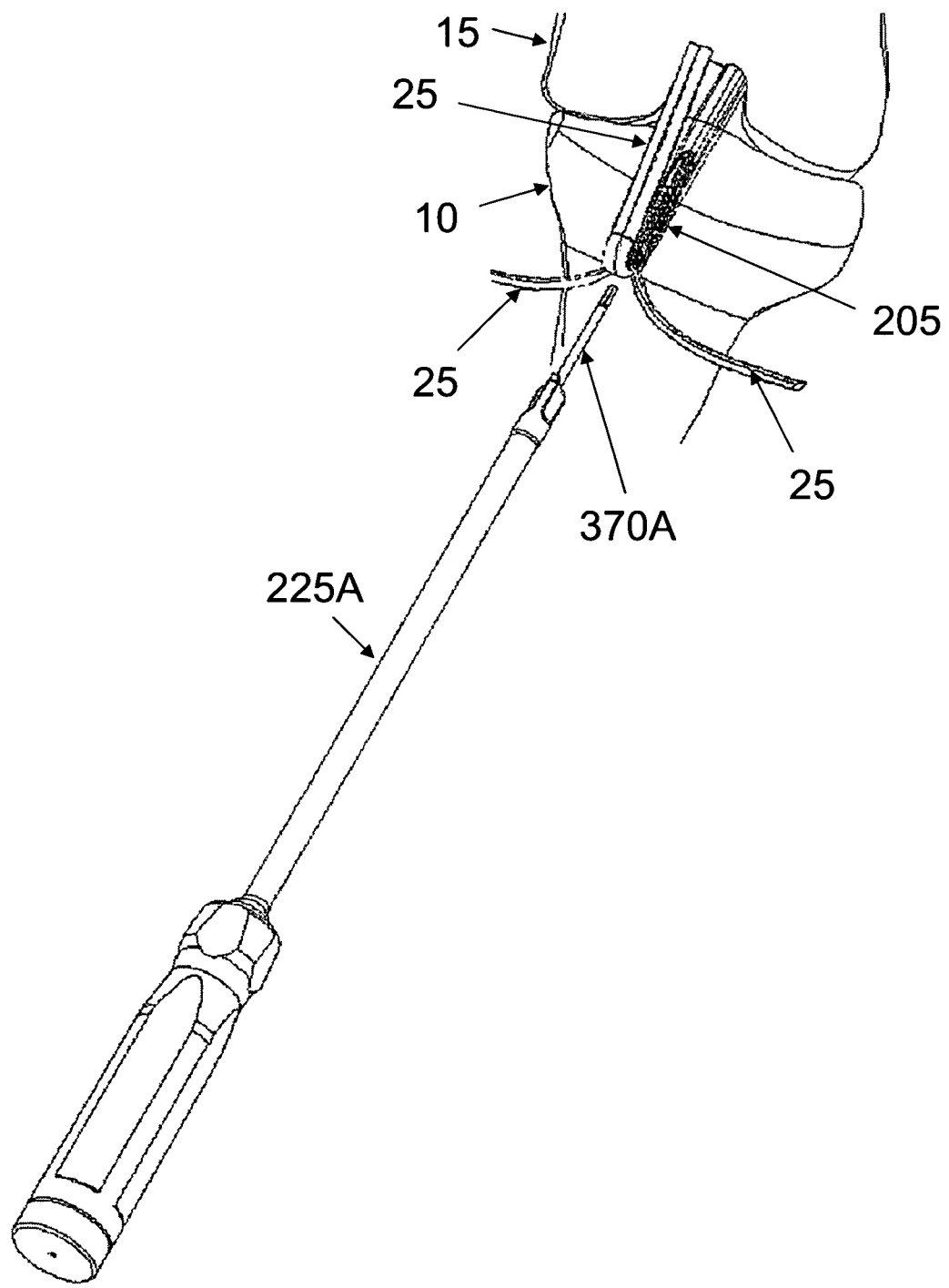
Figure 89A:
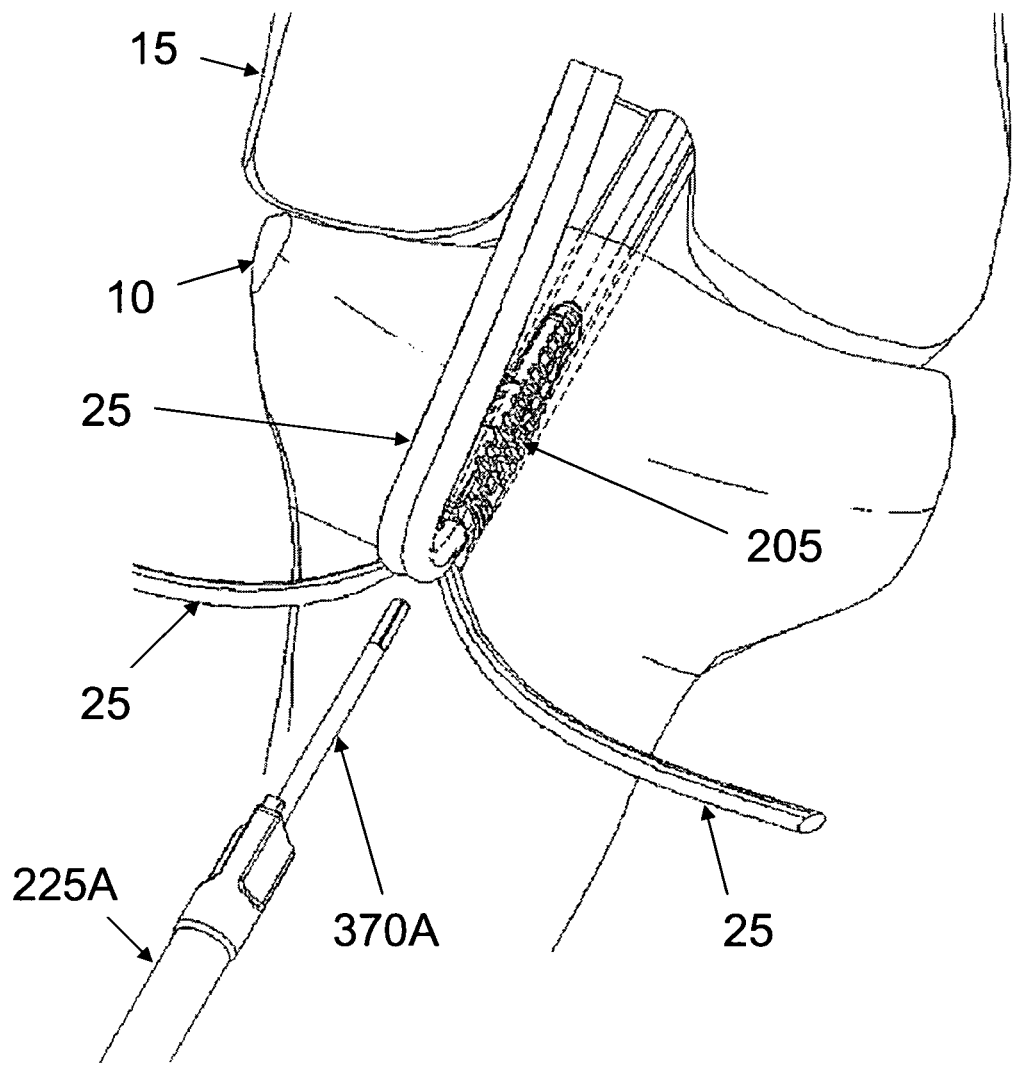

Next, retainer 205 is loaded onto inserter 225A, with inserter fingers 395A engaging recesses 275 in retainer 205, and with stylus 370A passing through the inserter shaft 355A, inserter tip 360A and retainer 205 (FIG. 86). Then inserter 225A is used to advance retainer 205 to its proper position within bone tunnel 30 (FIGS. 87 and 88). As retainer 205 is inserted into bone tunnel 30, graft ligament strands 25 (which are held under tension by pulling on their free ends) are received in the retainer's longitudinally-extending grooves 227 so that the retainer's lofted profile 255 gently but firmly compresses the graft ligament strands against the sidewall of the bone tunnel. Retainer 205 is advanced until it is properly wedged into position. Once the proper positioning of retainer 205 has been achieved, inserter 225A, including stylus 370A, is removed (FIGS. 89 and 89A). In this respect it should be appreciated that inserter 225A (including stylus 370A) can be removed without affecting the position of retainer 205 and/or ligament strands 25 inasmuch as retainer 205 has been wedged securely into position. At this point, retainer 205 compressively holds the graft ligament strands 25 against the bone, by virtue of its being wedged into position in the bone tunnel.

Figure 90:
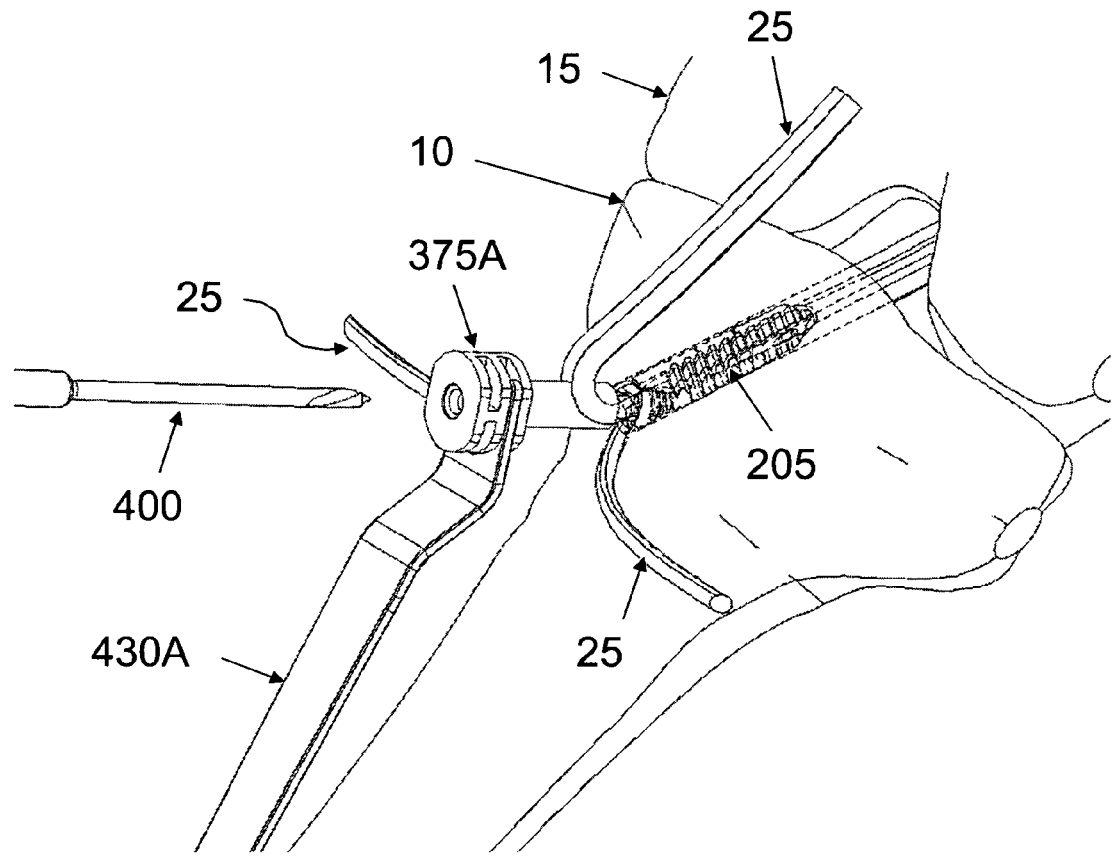
Figure 91:
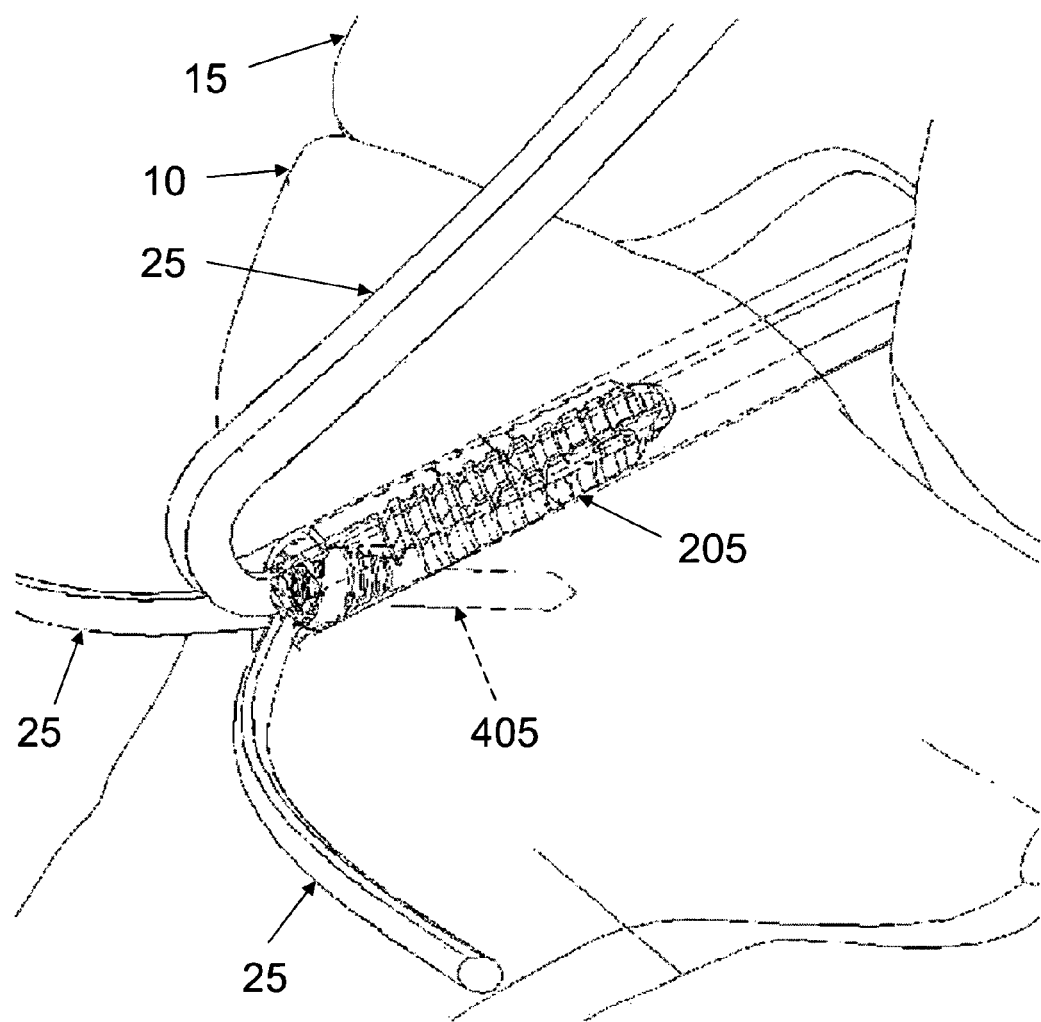

Next, drill bushing 375A is positioned in retainer crosshole 235 (FIG. 90), and a drill 400 is used to form a crosshole 405 into the host bone (FIGS. 90 and 91). Once the crosshole 405 has been formed, drill bushing 375A is removed (FIG. 91).

Figure 92:
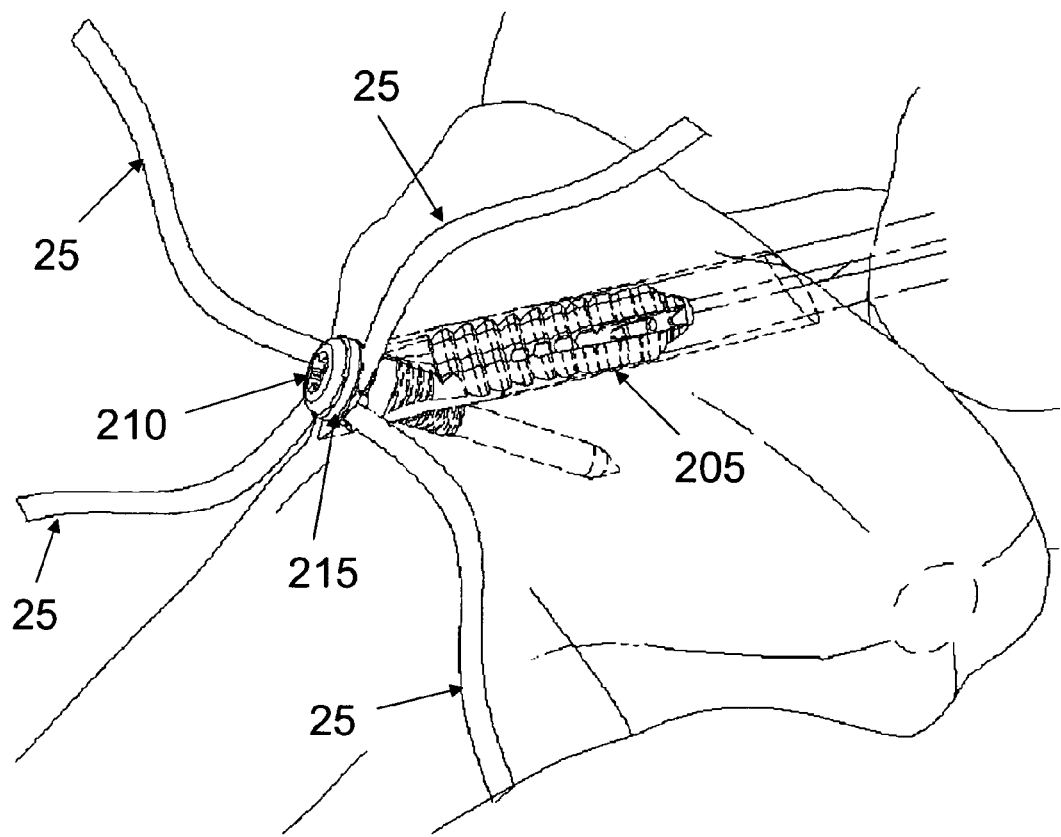

Next, locking pin 210 (with locking cap 215 carried in locking cap seat 305) is installed in retainer crosshole 235 and the crosshole 405 drilled into the host bone, with locking cap 215 capturing the graft ligament strands 25 against the retainer's mounting shoulder 240, so as to simultaneously bind retainer 205 to the host bone and graft ligament strands 25 to retainer 205 (FIG. 92). Again, with the system using the modified inserter 225A, graft ligament strands 25 are held to tibia 10 by virtue of the compression provided by retainer 205; in addition, the graft ligament strands 25 are secured to retainer 205 by locking cap 215, with the complete assembly being pinned to the host bone via locking pin 210.

It should also be appreciated that, inasmuch as graft ligament strands 25 tend to be slightly elastic, and inasmuch as graft ligament strands 25 are secured under tension, upon retainer deployment, graft ligament strands 25 will tend to urge retainer 205 further into the bone tunnel, thereby enhancing the wedging lock to the bone.

Thereafter, over time, graft ligament strands 25 and the host bone integrate so as to provide a biologic union.

Figure 93:
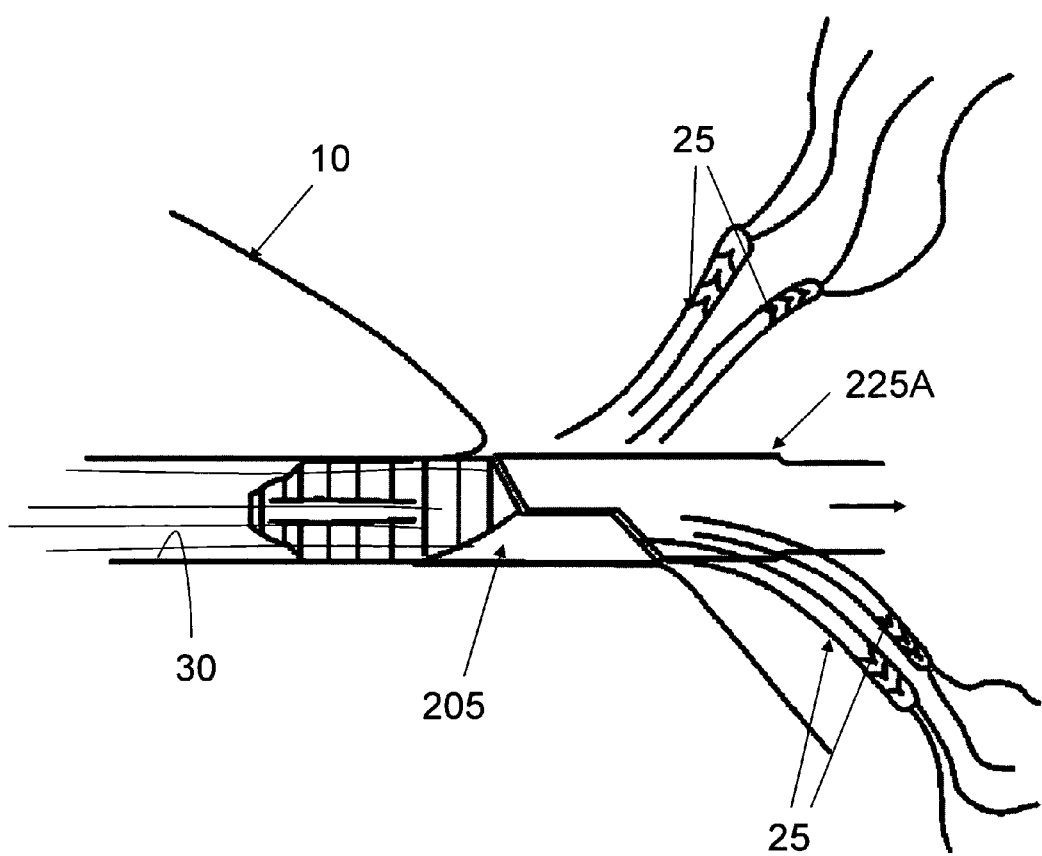
FIGS. 93 and 94 are schematic views showing another alternative form of the system formed in accordance with the present invention.
Figure 94:
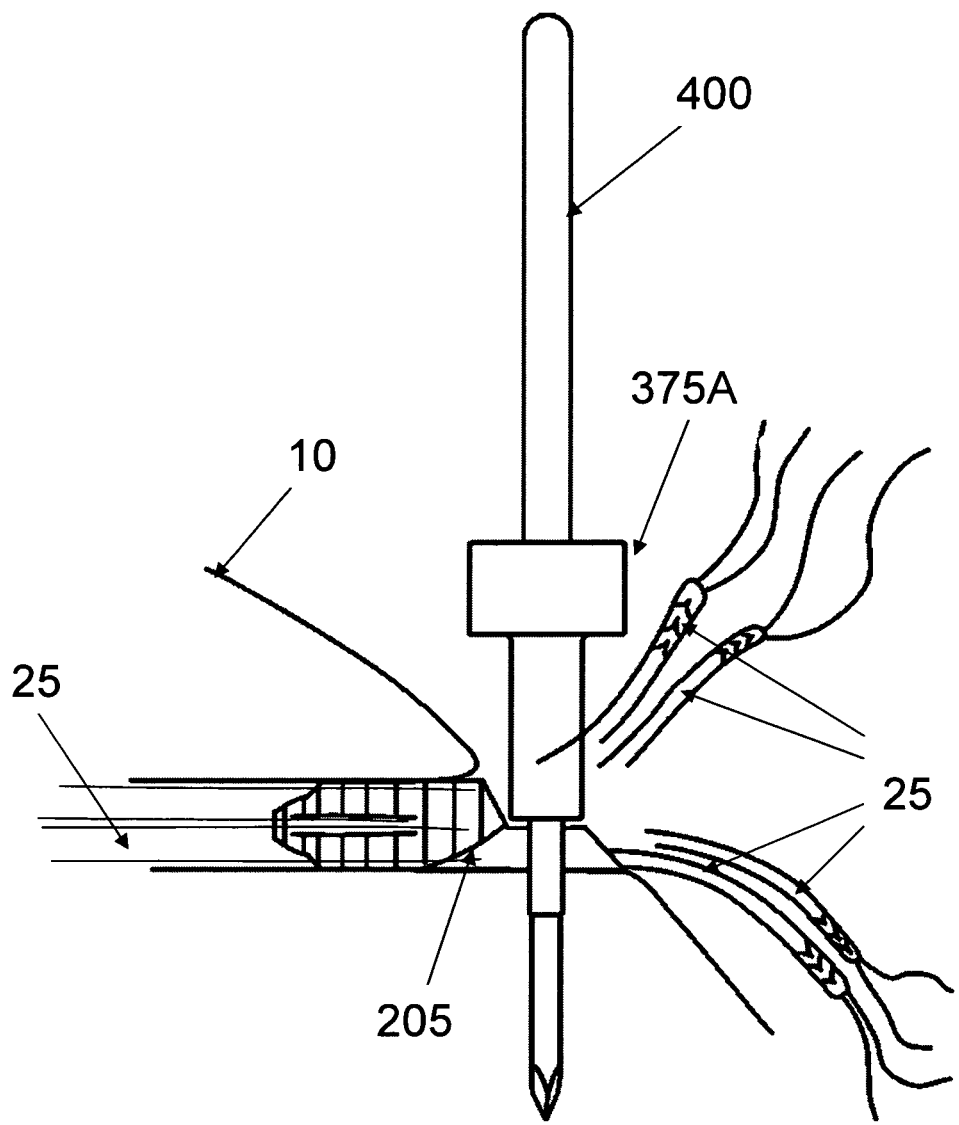

FIGS. 93 and 94 show another alternative form of the system formed in accordance with the present invention.

Modifications

It will be understood that many additional changes in the details, materials, steps and arrangements of parts, which have been herein described and illustrated in order to explain the nature of the invention, may be made by those skilled in the art while remaining within the principles and scope of the present invention.

What is claimed is:

1. A system for reconstructing a ligament by fixing at least one graft ligament strand in a tunnel, comprising:
   a retainer for disposition in the bone tunnel, wherein the retainer comprises at least one longitudinally-extending groove formed in the outside surface of the retainer, wherein the groove is configured to seat a graft ligament strand therein, and further wherein the at least one longitudinally-extending groove has a floor which is ramped radially outwardly as the floor extends distally-to-proximally, such that non-rotational advancement of the retainer into the bone tunnel will apply a compressive force to hold the graft ligament strand against the sidewall of the bone tunnel, and wherein the retainer comprises a transverse bore extending therethrough;
   a locking pin sized to pass through the transverse bore and into the sidewall of the bone tunnel so as to fix the retainer in place within the bone tunnel, the locking pin including a plurality of projections; and
   a cap including at least one locking member configured to engage the retainer to facilitate gripping of the at least one graft ligament strand between the cap and the retainer, wherein the cap defines a plurality of radial grooves configured to engage the plurality of projections formed on the locking pin to prevent backout of the locking pin.

2. A system according to claim 1 wherein the bone tunnel has a distal end and a proximal end, wherein the distal end of the bone tunnel has a smaller diameter than the proximal end, and further wherein the retainer has a diameter larger than the distal end of the bone tunnel and smaller than the proximal end of the bone tunnel, so that the retainer will be prevented from exiting the distal end of the tunnel.

3. A system according to claim 2 wherein the bone tunnel has a tapered configuration.

4. A system according to claim 2 wherein the bone tunnel has a bore-counterbore configuration.

5. A system according to claim 1 wherein the retainer is tapered along at least a portion of its length so as to have an increasing diameter as it extends distally-to-proximally.

6. A system according to claim 1 wherein the transverse bore extends at an acute angle to the longitudinal axis of the retainer.

7. A system according to claim 1 therein the transverse bore opens on a proximal end surface of the retainer.

8. A system according to claim 1 wherein the retainer has four longitudinally-extending grooves formed in the outside surface of the retainer.

9. A system according to claim 1 wherein the retainer further comprises at least one rib formed on the outside surface of the retainer, wherein the rib extends transverse to the longitudinal axis of the retainer.

10. A system according to claim 9 wherein at least a portion of the rib extends into the at least one groove.

11. A system according to claim 1 wherein the cap is removably attached to the retainer for capturing the at least one graft ligament strand to the retainer by compressing the at least one graft ligament strand between the cap and the retainer.

12. A system according to claim 11 wherein the distal end of the retainer has a stepped configuration so as to form a tortuous path for the at least one graft ligament strand.

13. A system according to claim 11 wherein the cap is attached to the proximal end of the retainer with a post and hole arrangement.

14. A system according to claim 13 wherein the cap comprises the post, and the retainer comprises the hole.

15. A system according to claim 14 wherein the post is threaded and the hole is threaded.

16. A system according to claim 14 wherein the post is ribbed.

17. A system according to claim 13 wherein the hole of the cap's post and hole arrangement is the transverse bore extending through the retainer, and the post of the cap's post and hole arrangement is the locking pin.

18. A system according to claim 17 wherein the post is threaded and the hole is threaded.

19. A system according to claim 17 wherein the cap is slidably mounted on the post.

20. A system according to claim 19 wherein the post comprises a head for holding the cap against the retainer.

21. A system according to claim 20 wherein the cap comprises a recess for seating the head of the post.

22. A system according to claim 11 wherein the at least on locking member comprises at least one longitudinally-extending projection extending distally away from the cap.

23. A system according to claim 22 wherein the retainer comprises at least one recess for receiving the at least one longitudinally-extending projection of the cap when the cap is mounted to the retainer.

24. A system according to claim 11 wherein the cap comprises at least one opening for passing the at least one graft ligament strand therethrough.

25. The system according to claim 1, wherein receipt of the plurality of protrusions of the locking pin within the radial grooves defined by the cap produces at least one of a tactile feedback and an audible feedback as proper compression is achieved on the graft ligament strand.

26. A system for reconstructing a ligament by fixing at least one graft ligament strand in a bone tunnel, comprising:
   a retainer configured for disposition in the bone tunnel, the retainer including a transverse bore for receiving a locking pin and a mounting shoulder formed about the transverse bore;
   a locking pin sized to pass through the transverse bore and into the sidewall of the bone tunnel so as to fix the retainer in place within the bone tunnel, the locking pin including a plurality of projections:, and
   a cap removably attached to the retainer for capturing the at least one graft ligament strand by compressing the at least one graft ligament strand between the cap and the retainer, wherein the cap includes at least one locking member configured to engage the mounting shoulder of the retainer to facilitate gripping of the at least one graft ligament strand between the cap and the retainer, wherein the cap defines a plurality of radial grooves configured to engage the plurality of projections formed on the locking Din to prevent backout of the locking pin.

27. A system according to claim 26 wherein the bone tunnel has a distal end and a proximal end, wherein the distal end of the bone tunnel has a smaller diameter than the proximal end, and further wherein the retainer has a diameter larger than the distal end of the bone tunnel and smaller than the proximal end of the bone tunnel, so that the retainer will be prevented from exiting the distal end of the tunnel.

28. A system according to claim 27 wherein the bone tunnel has a tapered configuration.

29. A system according to claim 27 wherein the bone tunnel has a bore-counterbore configuration.

30. A system according to claim 26 wherein the retainer is tapered along at least a portion of its length so as to have an increasing diameter as it extends distally-to-proximally.

31. A system according to claim 26 wherein the transverse bore extends at an acute angle to the longitudinal axis of the retainer.

32. A system according to claim 31 therein the transverse bore opens on a proximal end surface of the retainer.

33. A system according to claim 26 wherein the retainer further comprises at least one longitudinally-extending groove formed in the outside surface of the retainer, wherein the groove is configured to seat a graft ligament strand therein.

34. A system according to claim 33 wherein the at least one longitudinally-extending groove has a floor which is ramped relative to the longitudinal axis of the retainer.

35. A system according to claim 34 wherein the floor is ramped radially outwardly as the floor extends distally-to-proximally.

36. A system according to claim 33 wherein the retainer has four longitudinally-extending grooves formed in the outside surface of the retainer.

37. A system according to claim 26 wherein the retainer further comprises at least one rib formed on the outside surface of the retainer, wherein the rib extends transverse to the longitudinal axis of the retainer.

38. A system according to claim 26 wherein the retainer further comprises at least one longitudinally-extending groove formed in the outside surface of the retainer, wherein the groove is configured to seat a graft ligament strand therein, and wherein the retainer further comprises at least one rib formed on the outside surface of the retainer, wherein the rib extends transverse to the longitudinal axis of the retainer, and further wherein at least a portion of the rib extends into the at least one groove.

39. A system according to claim 26 wherein the distal end of the retainer has a stepped configuration so as to form a tortuous path for the at least one graft ligament strand.

40. A system according to claim 26 wherein the at least one locking member comprises at least one longitudinally-extending projection extending distally away from the cap.

41. A system according to claim 40 wherein the retainer comprises at least one recess for receiving the at least one longitudinally-extending projection of the cap when the cap is mounted to the retainer.

42. A system according to claim 26 wherein the cap comprises at least one opening for passing the at least one graft ligament strand therethrough.

43. The system according to claim 26, wherein receipt of the plurality of protrusions of the locking pin within the radial grooves defined by the cap produces at least one of a tactile feedback and an audible feedback as proper compression is achieved on the graft ligament strand.

* * * * *